United States Patent
Urban et al.

(12)

(10) Patent No.: US 6,696,061 B1
(45) Date of Patent: Feb. 24, 2004

(54) IMMUNOMODULATORY PEPTIDES

(75) Inventors: Robert Glen Urban, Lexington, MA (US); Roman M. Chicz, Belmont, MA (US); Dario A. A. Vignali, Rainham (GB); Mary Lynne Hedley, Lexington, MA (US); Lawrence J. Stern, Arlington, MA (US); Jack L. Strominger, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/077,255

(22) Filed: Jun. 15, 1993

Related U.S. Application Data

(63) Continuation-in-part of application No. 07/925,460, filed on Aug. 11, 1992, now abandoned.

(51) Int. Cl.$^7$ .................. A61K 38/17; A61K 38/08; C07K 7/00; C07K 14/00

(52) U.S. Cl. ................ 424/185.1; 424/277.1; 424/278.1; 424/810; 424/450; 424/283.1; 514/2; 514/885; 514/15; 514/14; 514/13; 514/12; 530/806; 530/328; 530/327; 530/326; 530/325; 530/324

(58) Field of Search .................. 424/152.1, 185.1, 424/198.1, 277.1, 278.1, 810, 450, 283.1; 514/2, 885, 15, 14, 13, 12; 530/328, 327, 326, 325, 324, 387.1, 806

(56) References Cited

U.S. PATENT DOCUMENTS

| | | | | |
|---|---|---|---|---|
| 4,478,823 | A | 10/1984 | Sanderson | ......... 424/88 |
| 4,681,760 | A | 7/1987 | Fathman | ......... 424/85 |
| 5,130,297 | A | 7/1992 | Sharma et al. | ......... 514/8 |
| 5,723,128 | A | * 3/1998 | Clayberger et al. | ... 424/185.1 |

FOREIGN PATENT DOCUMENTS

| | | |
|---|---|---|
| WO | WO 92/18150 | 10/1992 |
| WO | 94/21680 | 9/1994 |

OTHER PUBLICATIONS

Glimcher et al., J. Immunol., 138:1519–23, 1987.*
Rudensky et al., Nature, 353: 622–627, 1991.*
Edgington, Bio/Technology, 10:383–386, 388, 389, 1992.*
Osband et al., Imm Today, 11:193–195, 1990.*
Hurtenbach et al., J. Exp. Med., 177:1499–1504, 1993.*
Wauben et al., J. Immunol., 152:4211–4220, 1994.*
Chicz et al., J. Exp. Med., 178:27–47, 1993.*
Chicz et al., Predominant Naturally Processed Peptides Bound to HLA–DR1 are Derived from MHC–related Molecules and are Heterogeneous in Size, Nature 358:764–768, 1992.
Busch et al., "Degenerate Binding of Immunogenic Peptides to HLA–DR Proteins on B Cell Surfaces", International Immunology 2:443–451, 1990.
Ceppellini et al., "Binding of Labelled Influenza Matrix Peptide to HLA DR in Living B Lymphoid Cells", Nature 339:392–394, 1989.
O'Sullivan et al., "Truncation Analysis of Several DR Binding Epitopes", The Journal of Immunology 146:1240–1246, 1991.
O'Sullivan et al., "On the Interaction of Promiscuous Antigenic Peptides With Different DR Alleles" The Journal of Immunology 147:2663–2669, 1991.
Shrine, Immunologic's Allervax Effective Against Ragweed, Bioworld Today, The Biotechnology Newspaper, Mar. 4, 1996.
Shrine, Data on Cat Therapeutic May Not Support Filing, BioWorld Today, The Biotechnology Newspaper, Apr. 29, 1996.
Shrine et al., Pangaea Aims Naturally Processed Peptides at First Viral Target: Human Papilloma Virus, BioWorld Today, The Biotechnology Newspaper, 7:1–2, May 15, 1996.
Aharoni et al., T Suppressor Hybridomas and Interleukin–2 Dependent Lines Induced by Copolymer I or by Spinal Cord Homogenate Down Regulate Experimental Allergic Encephalomyelitis, Eur. J. Immunol. 23:17–25, 1993.
Bednarek et al., The Minimum Peptide Epitope from the Influenza Virus Matrix Protein, J. Immunology 147:4047–4053, 1991.
Bikoff et al., T Cell Recognition of Endogenous IgG$_{2a}$ Expressed in B Lymphoma Cells, Eur. J. Immunol. 18:341–348, 1988.
Briner et al., Peripheral T Cell Tolerance Induced in Naive and Primed Mice by Subcutaneous Injection of Peptides from Major Cat Allergen Fel d I, Proc. Natl. Acad. Sci. USA 90:7608–7612, 1993.
Brocke et al., Treatment of Experimental Encephalomyelitis with a Peptide Analogue of Myelin Basic Protein, Nature 379:343–346, 1996.
Brooks et al., Class II Restricted Presentation of an Endogenously Derived Immunodominant T Cell Determinant of Hen Egg Lysozyme 88:3290–3294, 1991.
Buus et al., The Relation Between Major Histocompatibility Complex (MHC) Restriction and the Capacity of Ia to Bind Immunogenic Peptides, Science 235:1353–1358, 1987.
Calin–Laurens et al., High Efficiency of Endogenous Antigen Presentation by MHC Class II Molecules, Interntl. Immunol. 4:1113–1121, 1992.
Chen et al., Cytotoxic T Cell Recognition of an Endogenous Class I HLA Peptide Presented by a Class II HLA Molecule, J. Exp. Med. 172:779–788, 1990.

(List continued on next page.)

*Primary Examiner*—Ronald B. Schwadron
(74) *Attorney, Agent, or Firm*—Fish & Richardson P.C.

(57) ABSTRACT

A purified preparation of a peptide consisting essentially of an amino acid sequence identical to that of a segment of a naturally-occurring human protein, said segment being of 10 to 30 residues in length, inclusive, wherein said peptide binds to a human major histocompatibility complex (MHC) class II allotype.

42 Claims, 3 Drawing Sheets

OTHER PUBLICATIONS

Fridkis–Hareli et al., Direct Binding of Myelin Basic Protein and Synthetic Copolymer I to Class II Major Histocompatibility Complex . . . Cell–Specificity and Promiscuity, Proc. Natl. Acad. Sci. USA 91:4872–4876, 1994.

Gammon et al., Endogenous Loading of HLA–A2 Molecules with an Analog of the Influenza Virus Matrix Protein–Derived Peptide and Its Inhibition by an Exogenous Peptide Antagonist, J. Immunology 148:7–12, 1992.

Gaur et al., Amelioration of Autoimmune Encephalomyelitis by Myelin Basic Protein Synthetic Peptide–Induced Anergy, Science 258:1491–1494.

Gould et al., A 15 Amino Acid Fragment of Influenza Nucleoprotein Synthesized in the Cytoplasm is Presented to Class I–Restricted Cytotoxic T Lymphocytes, J. Exp. Med. 170:1051–1056, 1989.

Guillet et al., Immunological Self, Nonself Discrimination, Science 235:865–870, 1987.

Hedley et al., Assembly and Peptide Binding of Major Histocompatibility Complex Class II Heterodimers in an In Vitro Translation System, Proc. Natl. Acad. Sci. USA 91;10479–10483, 1994.

Iwamoto et al., Prevention of Murine Lupus by an I–Eα Chain Transgene: Protective Role of I–Eα Chain Derived Peptides with a High Affinity I–A$^1$ Molecules, Eur. J. Immunol. 26:307–314, 1996.

Jaraquemada et al., An Endogenous Processing Pathway in Vaccinia Virus Infected Cells for Presentation of Cytoplasmic Antigens to Class II–restricted T Cells, J. Exp. Med. 172:947–954, 1990.

Johnson et al., Copolymer I Reduces Relapse Rate and Improves Disability in Relapsing–Remitting Multiple Sclerosis, Neurology 45:1268–1276, 1995.

Kourilsky et al., Working Principles in the Immune System Implied by the Peptidic "Self" Model, Proc. Natl. Acad. Sci. USA 84:3400–3404, 1987.

Lamb et al., Mapping of T Cell Epitopes Using Recombinant Antigens and Synthetic Peptides, The EMBO Journal 6:1245–1249, 1987.

Malnati et al., Processing Pathways for Cytosolic Antigen to MHC Class II Restricted T Cells, Nature 357:702–704, 1992.

Michalek et al., The Class II MHC–restricted Presentation of Endogenously Synthesized Ovalbumin Displays Clonal . . . Endosomal/Lysosomal Processing, and is Upregulated by Heat Shock, J. Immunology 148:1016–1024, 1992.

Nuchtern et al., Class II MHC Molecules Can Use the Endogenous Pathway of Antigen Presentation, Nature 343:74–76, 1990.

Sekaly et al., Antigen Presentation to HLA Class II Restricted Measles Virus Specific T Cell Clones Can Occur in the Absence of the Invariant Chain, Proc. Natl. Acad. Sci. USA 85:1209–1212, 1988.

Sinigaglia et al., A Malaria T Cell Epitope Recognized in the Association with Most Mouse and Human Class II Molecules, Nature 336:778–780, 1988.

Strassman et al., Inhibition of Immune Reactions In Vivo by Liposome Associated Transforming Growth Factor (TGF) Type Beta 1, Clin. Exp. Immunol. 86:532–536, 1991.

Strejan et al., Suppression of Experimental Allergic Encephalomyelitis in Guinea Pigs by Liposome–associated Human Myelin Basic Protein, J. Immunology 127:2064–2069, 1981.

Strejan et al., Suppression of Experimental Allergic Encephalomyelitis in Lewis Rats Treated with Myelin Basic Protein–liposome Complexes . . . Cell–Mediated Immunity Correlates, Cell Immunol. 84:171–184, 1984.

Strejan et al., Suppression of Chronic–relapsing EAE by Basic Protein–liposome Complexes, Prog. Clin. Biolo. Res. 146:429–434, 1984.

Sweetser et al., Class I MHC–Restricted Recognition of Cells Expressing a Gene Encoding a 41 Amino Acid Product of the Influenza Hemagglutinin, J. Immunology 141:3324–3328, 1988.

Teitelbaum et al., Specific Inhibition of the T Cell Response to Myelin Basic Protein by the Synthetic Copolymer Cop. I, Proc. Natl. Acad. Sci. USA 85:9724–9728, 1988.

Whitton et al., Class I MHC Can Present an Endogenous Peptide to Cytotoxic T Lymphocytes, J. Exp. Med. 170:1033–1038, 1989.

Acsadi et al., Human Dystrophin Expression in mdx Mice After Intramuscular Injection of DNA Constructs, Nature 352:815–818, 1991.

Allison et al., Liposomes as Immunological Adjuvants, Nature 252:252, 1974.

Anderson et al., Endogenously Synthesized Peptide with an Endoplasmic Reticulum Signal Sequence Sensitizes Antigen Processing Mutant Cells to Class I–restricted Cell–mediated Lysis, J. Exp. Med. 174:489–492, 1991.

Bakke and Dobberstein, MHC Class II–Associated Invariant Chain Contains a Sorting Signal for Endosomal Compartments, Cell 63:707–716, 1990.

Dal Monte and Szoka, Jr., Effect of Liposome Encapsulation on Antigen Presentation in Vitro, J. Immunology 142:1437–1443, 1989.

Donnely et al., Immunization with DNA, Journal of Immunological Methods 176:145–152, 1994.

Morein et al., Iscom, a novel structure for antigenic presentation of membrane proteins from enveloped viruses, Nature 308:457–460, 1984.

Noguchi et al., Priming for in vitro and in vivo anti–human T lymphotropic virus type 1 cellular immunity by virus–related protein reconstituted into liposome, J. Immun. 146:3599–3603, 1991.

Sweetser et al., Recognition of pre–processed endogenous antigen by class I but not class II MHC–restricted T cells, Nature 342:180–182, 1989.

van Binnendijk et al., Measles Virus Transmembrane Fusion Protein Synthesized De Novo or Presented in Immunostimulating Complexes is Endogenously Processed . . . Recognition, J. Exp. Med. 176:119–128, 1992.

Weiss and Bogen, MHC Class II–Restricted Presentation of Intracellular Antigen, Cell 64:767–776, 1991.

Wolff et al., Direct Gene Transfer into Mouse Muscle in Vivo, Science 247:1465–1468, 1990.

Claverie et al., "The Peptidic Self Model: A Reassessment of the Role of the Major Histocompatibility Complex Molecules in the Restriction of the T–Cell Response," *Ann. Inst. Pasteur/Immulol.,* 137:425–442, 1986.

Kourilsky et al., "The Peptidic Self Model: A Hypothesis on the Molecular Nature of the Immunological Self," *Ann. Inst. Pasteur/Immunol.,* 137:3–21, 1986.

Urban et al., "The Discover and Use of HLA–Associated Epitopes as Drugs," *Critical Reviews in Immunology,* 17:387–397, 1997.

Adorini et al., "Exogenous Peptides Compete for the Presentation of Endogenous Antigens to Major Histocompatibility Complex Class II–restricted T Cells" The Journal of Experimental Medicine, (Oct. 1991) 174:945–948.

Das et al., "Use of Synthetic Oligonucleotide Probes Complementary to Genes for Human HLA–DR α and β as Extension Primers for the Isolation of 5'–specific Genomic Clones," Proc. Natl. Acad. Sci. USA, 50:1531–1535 Mar., 1983.

Ramesh et al., "A Toxic Shock Syndrome Toxin–1 Peptide that shows Homology to Mycobacterial Heat Shock Protein 18 is Presented as Conventional Antigen to T Cells by Multiple HLA–DR Alleles," The Journal of Immunology, 148:1025–1030, Feb., 1992.

Urban et al., Biochemical Analysis of Naturally Processed Peptides Bound to Human Class II Molecules, J. Cell. Biochem., Keystone Symposia on Molecular & Cellular Biology, Supplement 160, 1992, p. 41:0262.

Rosen et al., "Dictionary of Immunology" published 1989 by Stockton Press (N.Y.), p. 23.

Sette et al., Random Association Between the Peptide Repertoire of A2.1 Class I and Several Different DR Class II Molecules, J. Immunology 147:3893–3900, 1991.

PCT Search Report in the corresponding PCT Patent Application No. PCT/US93/07545.

Adorini et al., Exogenous Peptides Compete for the Presentation of Endogenous Antigens to Major Histocompatibility Complex Class II–restricted T Cells, Immunology Today 11:945–948, 1991.

Adorini and Nagy, Peptide Competition for Antigen Presentation, Immunology Today 11:21–24, 1990.

Adorini et al., Competition for Antigen Presentation in Living Cells Involves Exchange of Peptides Bound by Class II MHC Molecules, Nature 342:800–803, 1989.

Adorini et al., Interaction of an Immunodominant Epitope with Ia Molecules in T–cell Activation, Proc. Natl. Acad. Sci. USA 85:5181–5185, 1988.

Adorini et al., In vivo Competition Between Self Peptides and Foreign Antigens in T–cell Activation, Nature 334:623–625, 1988.

Adorini et al., Mechanisms Influencing the Immunodominance of T Cell Determinants J. Experimental Medicine 168:2091–2104, 1988.

Babbitt et al., Antigenic Competition at the Level of Peptide–Ia Binding, Proc. Natl. Acad. Sci. USA 83:4509–4513, 1986.

Brodsky, The Invariant Dating Service, Nature 348:581–582, 1990.

Buus et al., Autologous Peptides Constitutively Occupy the Antigen Binding Site on Ia, Science 242:1045–1047, 1988.

Buus and Werdelin, Oligopeptide Antigens of the Angiotensin Lineage Compete for Presentation by Para–formaldehyde–treated Accessory Cells to T Cells, J. Immunology 136:459–465, 1986.

Collins et al., Processing of Exogenous Liposome–Encapsulated Antigens in vivo Generates Glass I MHC–Restricted T Cell Responses, J. Immunology 148:3336–3341, 1992.

De Magistris et al., Antigen Analog–Major Histocompatibility Complexes Act as Antagonists of the T Cell Receptor, Cell 68:625–634, 1992.

Demotz et al., Characterization of a Naturally Processed MHC Class II–restricted T–cell Determinant of Hen Egg Lysozyme, Nature 342:682–684, 1989.

Donermeyer and Allen, Binding to Ia Protects an Immunogenic Peptide from Proteolytic Degradation, J. Immunology 142:1063–1068, 1989.

Efraim and Liacopoulos, Inhibition of Delayed Hypersensitivity in Guinea–pigs after Competition Between Synthetic Antigens, Nature 711–713, 1967.

Falk et al., Cellular Peptide Composition Governed by Major Histocompatibility Complex Class I Molecules, Nature 348:248–251, 1990.

Falk et al., Allele–specific Motifs Revealed by Sequencing of Self–Peptides Eluted from MHC Molecules, Nature 351:290–296, 1991.

Falk et al., Identification of Naturally Processed Viral Nonepeptides Allows Their Quantification in Infected Cells and Suggests an Allele–specific T Cell Epitope Forecast, J. Exp. Med. 174:425–434, 1991.

Gorga, Structural Analysis of Class II Major Histocompatibility Complex Proteins Critical Reviews in Immunology 11:305–335, 1992.

Grey et al., Biologic Significance and Therapeutic Implications of Antigen/MHC Interactions, Clinical Immunology and Immunopathology 53:S47–S52, 1989.

Griem et al., Uneven Tissue Distribution of Minor Histocompatibility Proteins Versus Peptides is Caused by MHC Expression, Cell 65:633–640, 1991.

Guery et al., Selective Immunosuppression by Administration of Major Histocompatiblity Complex (MHC) Class II–binding Peptides. I. Evidence for In Vivo . . . T Cell Activation, J. Exp. Med. 175:1345–1352, 1992.

Guillet et al., Interaction of Peptide Antigens and Class II Major Histocompatibility Complex Antigens, Nature 324:260–262, 1986.

Guttinger et al., Human T Cells Recognize Polymorphic and Non–Polymorphic Regions of the Plasmodium falciparum Circumsporozoite Protein, EMBO Journal 7:2555–2558, 1988.

Harding et al., Liposome–Encapsulated Antigens are Processed in Lysosomes, Recycled, and Presented to T Cells, Cell 64:393–401, 1991.

Harris et al., MHC Class II Binding of Peptides Derived from HLA–DR 1, J. Immunology 148:2169–2174, 1992.

Henderson et al., HLA–A2.1—Associated Peptides from a Mutant Cell Line: A Second Pathway of Antigen Presentation, Science 255:1264–1266, 1992.

Hill et al., Conformational and Structural Characteristics of Peptides Binding to HLA–DR Molecules, J. Immunology 147:189–197, 1991.

Hunt et al., Characterization of Peptides Bound to the Class II MHC Molecule HLA–A2.1 by Mass Spectrometry, Science 255:1261–1263, 1992.

Hunt et al., Peptides Presented to the Immune System by the Murine Class II Major Histocompatibility Complex Molecule I–A, Science 256:1817–1820, 1992.

Janeway, Immunotherapy by Peptides?, Nature 341:482–483, 1989.

Jardetzky et al., Identification of Self Peptides Bound to Purified HLA–B27, Nature 353:326–328, 1991.

Jones et al., Detection of a Common Polypeptide Chain in I–A and I–E Sub–region Immunoprecipitates, Immunochemistry 16:51–60, 1978.

Kilgus et al., Vaccine T–cell Epitope Selection by a Peptide Competition Assay, Proc. Natl. Acad. Sci. USA 86:1629–1633, 1989.

Kropshofer et al., Self–Peptide Release from Class II HLA–DR1 Exhibits a Hydrophobic Two–Residue Contact Motif, J. Exp. Med. 175:1799–1803, 1992.

Lakey et al., Peptides Related to the Antigenic Determinant Block T Cell Recognition of the Native Protein as Process by Antigen–presenting Cells, Eur. J. Immunol. 16:721–727, 1986.

Lamont et al., The Use of Peptide Analogs with Improved Stability and MHC Binding Capacity to Inhibit Antigen Presentation in vitro and in vivo, J. Immunology 144:2493–2498, 1990.

Lamont et al., Inhibition of Experimental Autoimmune Encephalomyelitis Induction in SJL/J Mice by Using a Peptide with High Affinity for IA Molecules, J. Immunology 145:1687–1693, 1990.

Lanzavecchia et al., Irreversible Association of Peptides with Class II MHC Molecules in Living Cells, Nature 357:249–252, 1992.

Lehmann et al., Inhibition of T Cell Response with Peptides is Influenced by Both Peptide–binding Specificity of . . . Molecules and Susceptibility of T Cells to Blocking, Eur. J. Immunol. 19:1071–1077, 1989.

Margulies et al., Engineering Soluble Major Histocompatibility Molecules: Why and How, Immunol. Res. 6:101–116, 1987.

Maryanski et al., Competitor Analogs for Defined T Cell Antigens: Peptides Incorporating a Putative Binding Motif and Polyproline or Polyglycine Spacers, Cell 60:63–72, 1990.

Mowat and Donachie, ISCOMS—A Novel Strategy for Mucosal Immunization?, Immunology Today 12:383–385, 1991.

Muller et al., Selective in vivo Inhibition of T Cell Activation by Class II MHC–binding Peptides Administered in Soluble Form, J. Immunology 145:4006–4011, 1990.

O'Sullivan et al., Characterization of the Specificity of Peptide Binding to Four DR Haplotypes, J. Immunology 145:1799–1808, 1990.

Pala et al., Competition Between Unrelated Peptides Recognized by H–2–K Restricted T Cells, J. Immunology 141:2289–2294, 1988.

PCT Search Report in the corresponding case PCT/US92/06692.

Reddy et al., In Vivo Cytotoxic T Lymphocyte Induction with Soluble Proteins Administered in Liposomes, J. Immunology 148:1585–1589, 1992.

Roche and Cresswell, Invariant Chain Association with HLA–DR Molecules Inhibits Immunogenic Peptide Binding Nature 345:615–618, 1990.

Roche and Cresswell, High–Affinity Binding of an Influenza Hemagglutinin–Derived Peptide to Purified HLA–DR, J. Immunology 144:1849–1856, 1990.

Roche and Cresswell, Proteolysis of the Class II–associated Invariant Chain Generates a Peptide Binding Site in Intracellular HLA–DR Molecules, Proc. Natl. Acad. Sci. USA 88:3150–3154, 1991.

Rock and Benacerraf, Inhibition of Antigen–Specific T Lymphocyte Activation by Structurally Related Ir Gene–Controlled Polymers, J. Exp. Med. 157:1618–1634, 1983.

Rotzschke et al., On the Nature of Peptides Involved in T Cell Alloreactivity, J. Exp. Med. 174:1059–1071, 1991.

Rotzschke et al., Isolation and Analysis of Naturally Processed Viral Peptides as Recognized by Cytotoxic T Cells, Nature 348:252–254, 1990.

Rotzschke et al., Characterization of Naturally Occurring Minor Histocompatibility Peptides Including H–4 and H–Y, Science 249:283–287, 1990.

Rudensky et al., On the Complexity of Self, Nature 353:660–662, 1991.

Sadegh–Nasseri et al., A Role for Peptide in Determining MHC Class II Structure, Nature 353:167–170, 1991.

Sakai et al., Prevention of Experimental Encephalomyelitis with Peptides that Block Interaction of T Cells with Majoy Histocompatibility Complex Proteins, Proc. Natl. Acad. Sci. USA 86:9470–9474, 1989.

Smilek et al., A Single Amino Acid Change in a Myclin Basic Protein Peptide Confers the Capacity to Prevent Rather than Induce Experimental Autoimmune Encephalomyelitis, Proc. Natl. Acad. Sci. USA, 88:9633–9637, 1991.

Smith and Allen, Myosin–Induced Acute Myocarditis is a T Cell–Mediated Disease, J. Immunology 147:2141–2147, 1991.

Springer et al., Purification of HLA–linked B Lymphocyte Alloantigens in Immunologically Active Form by . . . Electrophoresis and Studies on Their Subunit Association, J. Biol. Chem. 17:6201–6207, 1977.

Srinivasan et al., Characterization of Naturally Processed Antigen Bound to Major Histocompatibility Complex Class II Molecules, Proc. Natl. Acad. Sci. USA 88:7928–7932, 1991.

Stern and Wiley, The Human Class II MHC Protein HLA–DR1 Assembles as Empty $\alpha\beta$ Heterodimers in the Absence of Antigenic Peptide, Cell 68:465–477, 1992.

Takahashi et al., Induction of CD8+ Cytotoxic T Cells by Immunization with Purified HIV–1 Envelope Protein in ISCOMs, Nature 344:873875, 1990.

Taussig, Studies on Antigenic Competition, Eur. J. Immunol. 2:118–122, 1972.

Taussig et al. Studies on the Mechanism of Antigenic Competition: Analysis of Competition Between Synthetic Polypeptide Antigens, Eur. J. Immunol. 2:448–452, 1972.

Thomas et al., Proteolytic Cleavage of $I_i$ to p25, J. Immunology 140:2670–2674, 1988.

Urban et al., Autoimmune T Cells: Immune Recognition of Normal and Variant Peptide Epitopes and Peptide–Based Therapy, Cell 59:257–271, 1989.

Van Bleek and Nathenson, Isolation of an Endogenously Processed Immunodominant Viral Peptide from the Class I H–2K$^b$ Molecule, Nature 348:213–215, 1990.

Wei and Cresswell, HLA–A2 Molecules in an Antigen–processing Mutant Cell Contain Signal Sequence–derived Peptides, Nature 356:443–446, 1992.

Wraith et al., Antigen Recognition in Autoimmune Encephalomyelitis and the Potential for Peptide–Mediated Immunotherapy, Cell 59:247–255, 1989.

Werdelin, Chemically Related Antigens Compete for Presentation by Accessory Cells to T Cells, J. Immunology 129:1883–1891, 1982.

* cited by examiner

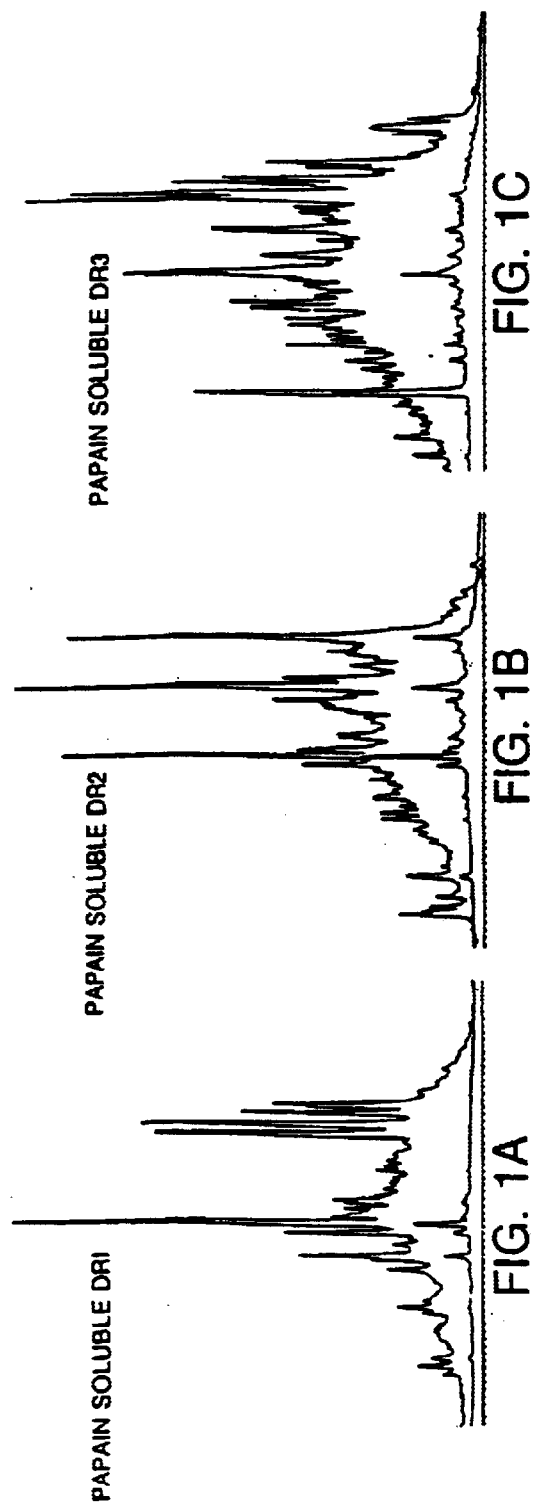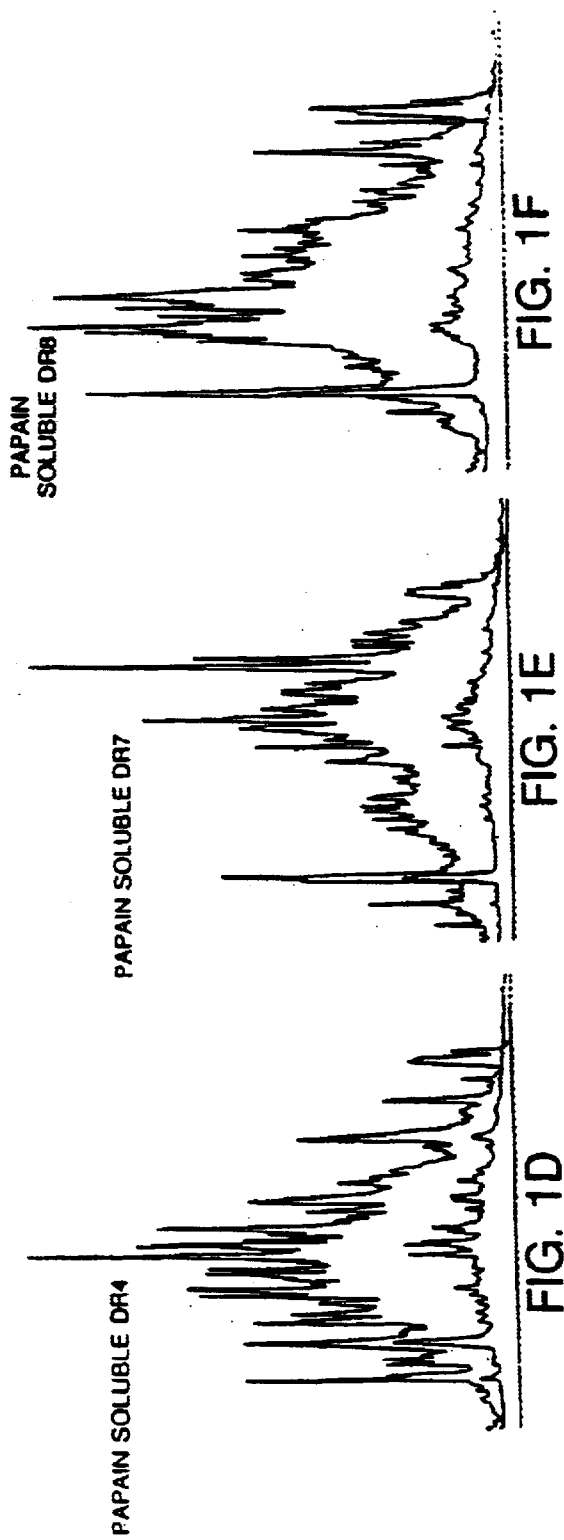

```
ATG GCC ATA AGT GGA GTC CCT GTG CTA GGA TTT TTC ATC ATA GCT
 M   A   I   S   G   V   P   V   L   G   F   F   I   I   A

GTG CTG ATG AGC GCT CAG GAA TCA TGG GCT AAG ATG CGC ATG GCC
 V   L   M   S   A   Q   E   S   W   A   K   M   R   M   A

ACC CCG CTG CTG ATG CAG GCG CTG CCC ATG TAA
 T   P   L   L   M   Q   A   L   P   M  stop
```

FIG. 3A

```
ATG GCC ATA AGT GGA GTC CCT GTG CTA GGA TTT TTC ATC ATA GCT
 M   A   I   S   G   V   P   V   L   G   F   F   I   I   A

GTG CTG ATG AGC GCT CAG GAA TCA TGG GCT CTT CCC AAG CCT CCC
 V   L   M   S   A   Q   E   S   W   A   L   P   K   P   P

AAG CCT GTG AGC AAG ATG CGC ATG GCC ACC CCG CTG CTG ATG CAG
 K   P   V   S   K   M   R   M   A   T   P   L   L   M   Q

GCG CTG CCC ATG TAA
 A   L   P   M  stop
```

IMMUNOMODULATORY PEPTIDES

This application is a continuation-in-part of U.S. Ser. No. 07/925,460, filed Aug. 11, 1992, now abandoned.

The invention was made in the course of research funded in part by the U.S. Government under NIH Grant 5R35-CA47554; the U.S. Government therefore has certain rights in the invention.

The field of the invention is major histocompatibility complex (MHC) antigens.

BACKGROUND OF THE INVENTION

Major histocompatibility complex (MHC) class II antigens are cell surface receptors that orchestrate all specific immune responses in vertebrates. Humans possess three distinct MHC class II isotypes: DR, for which approximately 70 different allotypes are known; DQ, for which 33 different allotypes are known; and DP, for which 47 different allotypes are known. Each individual bears two to four DR alleles, two DQ alleles, and two DP alleles.

MHC receptors (both class I and class II) participate in the obligate first step of immune recognition by binding small protein fragments (peptides) derived from pathogens or other non-host sources, and presenting these peptides to the regulatory cells (T cells) of the immune system. In the absence of MHC presentation, T cells are incapable of recognizing pathogenic material. Cells that express MHC class II receptors are termed antigen presenting cells (APC). APCs ingest pathogenic organisms and other foreign materials by enveloping them in endosomic vesicles, then subjecting them to enzymatic and chemical degradation. Foreign proteins which are ingested by APCs are partially degraded or "processed" to yield a mixture of peptides, some of which are bound by MHC class II molecules that are en route to the surface. Once on the cell surface, MHC-bound peptides are available for T cell recognition.

MHC class II antigens are expressed on the surface of APCs as a trimolecular complex composed of an α chain, a p chain, and a processed peptide. Like most polypeptides that are expressed on the cell surface, both α and β chains contain short signal sequences at their $NH_2$ termini which target them to the endoplasmic reticulum (ER). Within the ER the class II α/β chain complex associates with an lo additional protein termed the invariant chain (Ii). Association with Ii is proposed to block the premature acquisition of peptides (by blocking the peptide binding cleft of the MHC heterodimer), promote stable α/β interaction, and direct subsequent intracellular trafficking of the complex to endosomal vesicles. In the endosomes, Ii is removed by a process involving proteolysis; this exposes the peptide binding cleft, thus allowing peptides present in the endosome to bind to the MHC molecule. The class II/peptide complex is transported from the endosomes to the cell surface where it becomes accessible to T-cell recognition and subsequent activation of immune responses. Class II MHC molecules bind not only to peptides derived from exogenous (ingested) proteins, but also to those produced by degradation of endogenous (self) proteins. The amount of each species of peptide which binds class II is determined by its local concentration and its relative binding affinity for the given class II binding groove, with the various allotypes displaying different peptide-binding specificities.

Early during fetal development, the mammalian immune system is "tolerized", or taught not to react, to self-peptides. The stability and maintenance of this system is critical for ensuring that an animal does not generate an immune response against self. A breakdown of this system gives rise to autoimmune conditions such as diabetes, rheumatoid arthritis and multiple sclerosis. Current technologies intended to manipulate the immune system into reestablishing proper nonresponsiveness include protocols involving the intravenous delivery of synthetic, high affinity binding peptides as blocking peptides.

Vaccination can generate protective immunity against a pathogenic organism by stimulating an antibody-mediated and/or a T cell-mediated response. Most of the current vaccination strategies still use relatively crude preparations, such as attenuated or inactivated viruses. These vaccines often generate both antibody- and cell-mediated immunity, and do not allow one to modulate the type of immune response generated. Moreover, in many diseases the generation of the wrong type of response can result in an exacerbated disease state.

SUMMARY OF THE INVENTION

In the work disclosed herein, naturally processed peptides bound to six of the some 70 known human MHC class II DR allotypes (HLA-DR1, HLA-DR2, HLA-DR3, HLA-DR4, HLA-DR7, and HLA-DR8) have been characterized. These peptides were found to be predominantly derived from self proteins rather than foreign proteins. Several self peptide families have been identified with the unexpected property of degenerate binding: that is, a given self-peptide will bind to a number of HLA-DR allotypes. This observation runs counter to the widely-accepted view of MHC class II function, which dictates that each allotype binds a different set of peptides. Furthermore, many if not all of the self-peptides disclosed herein bind to the class II molecules with relatively high affinity. These three characteristics—(1) self rather than foreign, (2) degeneracy, and (3) high affinity binding—suggest a novel means for therapeutic intervention in disease conditions characterized by autoreactivity, such as Type I diabetes, rheumatoid arthritis, and multiple sclerosis. In addition, such therapy could be used to reduce transplant rejection.

In the therapeutic methods of the invention, short peptides modelled on the high-affinity immunomodulating self peptides of the invention (which preferably are nonallelically restricted) are introduced into the APCs of a patient. Tissue typing to determine the particular class II alleles expressed by the patient may be unnecessary, as the peptides of the invention are bound by multiple class II isotypes. It may be useful to employ a "cocktail" of peptides, where complete degeneracy is lacking for individual peptides, i.e., where peptides binds to fewer than all allotypes; the cocktail provides overlapping binding specificity. Once in the APC, a peptide binds to the class II molecules with high affinity, thereby blocking the binding of immunogenic peptides which are responsible for the immune reaction characteristic of the disease condition. Because the blocking peptides of the invention are self peptides with the exact carboxy and amino termini tolerized during ontogeny, they are immunologically inert and will not induce an immune response which may complicate treatment using non-self blocking peptides.

The peptides of the invention may be introduced into APCs directly, e.g., by intravenous injection of a solution containing one or more of the peptides. Alternatively, the APCs may be provided with a means of synthesizing large quantities of the blocking peptides intracellularly. Recombinant genes that encode ER and/or endosomal targeting signals fused to blocking peptide sequences are linked to appropriate expression control sequences and introduced into APCs. Once in the cell, these genes direct the expression of the hybrid peptides. Peptides targeted to the ER will bind class II α and β chains as they are translated and assembled into heterodimers. The presence of high affinity binding peptides within the ER will prevent association of the α/β complex with invariant chain, and thus interfere with intracellular trafficking. The class II molecule/blocking peptide complex may subsequently be expressed on the cell surface, but would not elicit an immune response since T cells are tolerized to this complex early in development. The use of peptides tagged with ER retention signals may also prevent the peptide-complexed class II molecules from leaving the ER. Alternatively, the recombinant peptide may be tagged with an endosomal targeting signal which directs it to the endosomal compartment after synthesis, thereby also skewing the ratio of endogenously-processed peptide to blocking peptide in the endosome and favoring binding of the high affinity blocking peptide to any class II molecules which did not bind it in the ER. It may be advantageous, for any individual patient, to employ one or more ER-directed peptides in combination with one or more endosome-directed peptide, so that α-β complexes which are not filled in the ER with peptides of the invention are then blocked in the endocytic pathway. The end result again is cell surface expression of a non-immunogenic class II/peptide complex.

The use of a class II nonrestricted high affinity binding peptide coupled to an intracellular delivery system permits the specific down-regulation of class II restricted immune responses without invoking the pleiotropic adverse reactions associated with the current pharmacological strategies. Successful application of these technologies will constitute a significant advance towards the treatment of autoimmune disease and prevention of transplant rejection.

The intracellular delivery system of the invention can also be utilized in a novel method of vaccination of an animal, e.g., a human patient or a commercially significant mammal such as a cow which is susceptible to diseases such as hoof and mouth disease. Such a system can be tailored to generate the type of immune response required in a given situation by adjustments in the following: (a) peptide specificity for class I or class II MHC; (b) peptide/protein length and/or sequence, and (c) using specific tags for organelle targeting. The system of the invention ensures that peptides are produced only within cells, and are not present outside the cells where they could stimulate antibody production by contact with B cells. This limits the immune response generated by such a vaccine to T cell-mediated immunity, thereby preventing either an inappropriate or potentially deleterious response as might be observed with standard vaccines targeting the organisms which cause, for example, HIV, malaria, leprosy, and leishmaniasis. Furthermore, this exclusively T cell-mediated immune response can be class I or class II-based, or both, depending upon the length and character of the immunogenic peptides: MHC class I molecules are known to bind preferentially to peptides 8 to 10 residues in length, while class II molecules bind with high affinity to peptides that range from 12 to 25 residues long.

Immunization and therapy according to the invention can employ a purified preparation of a peptide of the invention, i.e., a peptide which includes an amino acid sequence identical to that of a segment of a naturally-occurring human protein (i.e., a "self protein"), such segment being of 10 to 30 residues in length, wherein the peptide binds to a human MHC class II allotype, and preferably binds to at least two distinct MHC class II allotypes (e.g., any of the approximately 70 known DR allotypes, approximately 47 known DP allotypes, or approximately 33 known DQ allotypes). The portion of the peptide corresponding to the self protein segment is herein termed a "self peptide". By "purified preparation" is meant a preparation at least 50% (by weight) of the polypeptide constituents of which consists of the peptide of the invention. In preferred embodiments, the peptide of the invention constitutes at least 60% (more preferably at least 80%) of the purified preparation. The naturally-occurring human protein is preferably HLA-A2 (as broadly defined below), HLA-A29, HLA-A30, HLA-B44, HLA-B51, HLA-Bw62, HLA-C, HLA-DP β-chain, HLA-DQ α-chain, HLA-DQ β-chain, HLA-DQ3.2 β-chain, HLA-DR α-chain, HLA-DR β-chain, HLA-DR4 β-chain, invariant chain (Ii), Ig kappa chain, Ig kappa chain C region, Ig heavy chain, $Na^+/K^+$ ATPase, potassium channel protein, sodium channel protein, calcium release channel protein, complement C9, glucose-transport protein, CD35, CD45, CD75, vinculin, calgranulin B, kinase C ζ-chain, integrin β-4 gp150, hemoglobin, tubulin α-1 chain, myosin β-heavy chain, α-enolase, transferrin, transferrin receptor, fibronectin receptor α-chain, acetylcholine receptor, interleukin-8 receptor, interferon α-receptor, interferon γ-receptor, calcitonin receptor, LAM (lymphocyte activation marker) Blast-1, LAR (leukocyte antigen-related) protein, LIF (leukemia inhibitory factor) receptor, 4F2 cell-surface antigen (a cell-surface antigen involved in normal and neoplastic growth) heavy chain, cystatin SN, VLA-4 (a cell surface heterodimer in the integrin superfamily of adhesion receptors), PAI-1 (plasminogen activator inhibitor-1), IP-30 (interferon-γ induced protein), ICAM-2, carboxypeptidase E, thromboxane-A synthase, NADH-cytochrome-b5 reductase, c-myc transforming protein, K-ras transforming protein, MET kinase-related transforming protein, interferon-induced guanylate-binding protein, mannose-binding protein, apolipoprotein B-100, cathepsin C, cathepsin E, cathepsin S, Factor VIII, von Willebrand factor, metalloproteinase inhibitor 1 precursor, metalloproteinase inhibitor 2, plasminogen activator inhibitor-1, or heat shock cognate 71 kD protein; it may be an MHC class I or II antigen protein or any other human protein which occurs at the cell surface of APCs. The self peptide preferably conforms to the following motif: at a first reference position (I) at or within 12 residues of the amino terminal residue of the segment, a positively charged residue (i.e., Lys, Arg, or His) or a large hydrophobic residue (i.e., Phe, Trp, Leu, Ile, Met, Tyr, or Pro; and at position I+5, a hydrogen bond donor residue (i.e., Tyr, Asn, Gln, Cys, Asp, Glu, Arg, Ser, Trp, or Thr). In addition, the peptide may also be characterized as having, at positions I+9, I+1, and/or I−1, a hydrophobic residue (i.e., Phe, Trp, Leu, Ile, Met, Pro, Ala, Val, or Tyr) (+ denotes positions to the right, or toward the carboxy terminus, and − denotes positions to the left, or toward the amino terminus.) A typical peptide of the invention will include a sequence corresponding to residues 32–41 (i.e., TQFVRFDSDA; SEQ ID NO: 149) or residues 107–116 (i.e., DWRFLRGYHQ; SEQ ID NO: 150) of HLA-2, or residues 108–117 (i.e., RMATPLLMQA; SEQ ID NO: 151) of Ii, or a sequence essentially identical to any one of the sequences set forth in Tables 1–10 below.

The therapeutic and immunization methods of the invention can also employ a nucleic acid molecule (RNA or DNA) encoding a peptide of the invention, but encoding less than all of the entire sequence of the self protein. The nucleic acid preferably encodes no substantial portion of the self protein other than the specified self peptide which binds to a MHC class II molecule, although it may optionally include a signal peptide or other trafficking sequence which was derived from the self protein (or from another protein). A trafficking sequence is an amino acid sequence which functions to control intracellular trafficking (directed movement from organelle to organelle or to the cell surface) of a polypeptide to which it is attached. Such trafficking sequences might traffic the polypeptide to ER, a lysosome, or an endosome, and include signal peptides (the amino terminal sequences which direct proteins into the ER during translation), ER retention peptides such as KDEL (SEQ ID NO: 152); and lysosome-targeting peptides such as KFERQ (SEQ ID NO: 153), QREFK (SEQ ID NO: 154), and other pentapeptides having Q flanked on one side by four residues selected from K, R, D, E, F, I, V, and L. An example of a signal peptide that is useful in the invention is a signal peptide substantially identical to that of an MHC subunit such as class II α or β; e.g., the signal peptide of MHC class II α is contained in the sequence MAISGVPVLGFFIIAVLMSAQESWA (SEQ ID NO: 155). The signal peptide encoded by the nucleic acid of the invention may include only a portion (e.g., at least ten amino acid residues) of the specified 25 residue sequence, provided that portion is sufficient to cause trafficking of the polypeptide to the ER. In preferred embodiments, the nucleic acid of the invention encodes a second self peptide and a second trafficking sequence (which may be identical to or different than the first self peptide and first trafficking sequence), and it may encode additional self peptides and trafficking sequences as well. In still another variation on this aspect of the invention, the self peptide sequence (or a plurality of self peptide sequences arranged in tandem) is linked by a peptide bond to a substantially intact Ii polypeptide, which then carries the self peptide sequence along as it traffics the class II molecule from ER to endosome.

The nucleic acid of the invention may also contain expression control sequences (defined as transcription and translation start signals, promoters, and enhancers which permit and/or optimize expression of the coding sequence with which they are associated) and/or genomic nucleic acid of a phage or a virus, such as an attenuated or non-replicative, non-virulent form of vaccinia virus, adenovirus, Epstein-Barr virus, or a retrovirus.

The peptides and nucleic acids of the invention may be prepared for therapeutic use by suspending them directly in a pharmaceutically acceptable carrier, or by encapsulating them in liposomes, immune-stimulating complexes (ISCOMS), or the like. Such preparations are useful for inhibiting an immune response in a human patient, by contacting a plurality of the patient's APCs with the therapeutic preparation and thereby introducing the peptide or nucleic acid into the APCS.

Also within the invention is a cell (e.g., a tissue culture cell or a cell, such as a B cell or APC, within a human) containing the nucleic acid molecule of the invention. A cultured cell containing the nucleic acid of the invention may be used to manufacture the peptide of the invention, in a method which involves culturing the cell under conditions permitting expression of the peptide from the nucleic acid molecule.

Disclosed herein is a method of identifying a nonallelically restricted immunomodulating peptide, which method includes the steps of:

(a) fractionating a mixture of peptides eluted from a first MHC class II allotype;

(b) identifying a self peptide from this mixture; and (c) testing whether the self peptide binds to a second MHC class II allotype, such binding being an indication that the self peptide is a nonallelically restricted immunomodulating peptide.

In further embodiments, the invention includes a method of identifying a potential immunomodulating peptide, in a method including the steps of:

(a) providing a cell expressing MHC class II molecules on its surface;

(b) introducing into the cell a nucleic acid encoding a candidate peptide; and (c) determining whether the proportion of class II molecules which are bound to the candidate peptide is increased in the presence of the nucleic acid compared to the proportion bound in the absence of the nucleic acid, such an increase being an indication that the candidate peptide is a potential immunomodulating peptide.

Also within the invention is a method of identifying a potential immunomodulating peptide, which method includes the steps of:

(a) providing a cell expressing MHC class II molecules on its surface;

(b) introducing into the cell a nucleic acid encoding a candidate peptide; and (c) determining whether the level of MHC class II molecules on the surface of the cell is decreased in the presence of the nucleic acid compared to the level of MHC class II molecules in the absence of the nucleic acid, such a decrease being an indication that the candidate peptide is a potential immunomodulating peptide.

Also included in the invention is a method of identifying a nonallelically restricted immunostimulating peptide, which method includes the steps of:

(a) providing a cell bearing a first MHC class I or class II allotype, such cell being infected with a pathogen (e.g., an infective agent which causes human or animal disease, such as human immunodeficiency virus (HIV), hepatitis B virus, measles virus, rubella virus, influenza virus, rabies virus, *Corynebacterium diphtheriae, Bordetella pertussis*, Plasmodium spp., Schistosoma spp., Leishmania spp., Trypanasoma spp., or *Mycobacterium lepre*);

(b) eluting a mixture of peptides bound to the cell's first MHC allotype;

(c) identifying a candidate peptide from the mixture, such candidate peptide being a fragment of a protein from the pathogen; and (d) testing whether the candidate peptide binds to a second MHC allotype, such binding being an indication that the candidate peptide is a nonallelically restricted immunostimulating peptide. A nucleic acid encoding such an immunogenic fragment of a protein of a pathogen can be used in a method of inducing an immune response in a human patient, which method involves introducing the nucleic acid into an APC of the patient.

The therapeutic methods of the invention solve certain problems associated with prior art methods involving intravenous injection of synthetic peptides: (1) because of allelic specificity, a peptide capable of binding with high affinity to all, or even most, of the different class II allotypes expressed within the general population had not previously been identified; (2) the half-lives of peptides delivered intravenously are generally very low, necessitating repeated administration with the associated high level of inconvenience and cost; (3) this type of delivery approach requires that the blocking peptide displace the naturally-occurring peptide occupying the binding cleft of a class II molecule while the latter is on the cell surface, which is now believed to be a very inefficient process; and (4) if the blocking peptide utilized is itself immunogenic, it may promote deleterious immune responses in some patients.

Other features and advantages of the invention will be apparent from the following detailed description, and from the claims.

DETAILED DESCRIPTION

The drawings are first briefly described.
Drawings

FIGS. 1A–1F are chromatographic analyses of the peptide pools extracted from papain digested HLA-DR1, DR2, DR3, DR4, DR7, and DR8, respectively, illustrating the peptide repertoire of each HLA-DR as detected by UV absorbance. The UV absorbance for both 210 nm and 277 nm is shown at a full scale absorbance of 500 mAU with a retention window between 16 minutes and 90 minutes (each mark represents 2 minutes).

FIG. 2 is a representative mass spectrometric analysis of the size distribution of isolated HLA-DR1 bound peptides. The determined peptide masses in groups of 100 mass units were plotted against the number of isolated peptides identified by mass spectrometry. Peptide length was calculated by dividing the experimental mass by an average amino acid mass of 118 daltons.

FIG. 3A is a representation of a minigene of the invention (SEQ ID NO: 147), in which the HLA-DRα chain leader peptide is linked to the amino terminus of a 15-residue blocking peptide fragment of human invariant chain Ii.

FIG. 3B is a representation of a second minigene of the invention (SEQ ID NO: 148), in which the HLA-DRα chain leader peptide is linked to the amino terminus of a 24-residue blocking peptide fragment of human invariant chain Ii.

EXPERIMENTAL DATA

METHODS

I. Purification of HLA-DR Antigens

Figure 2:
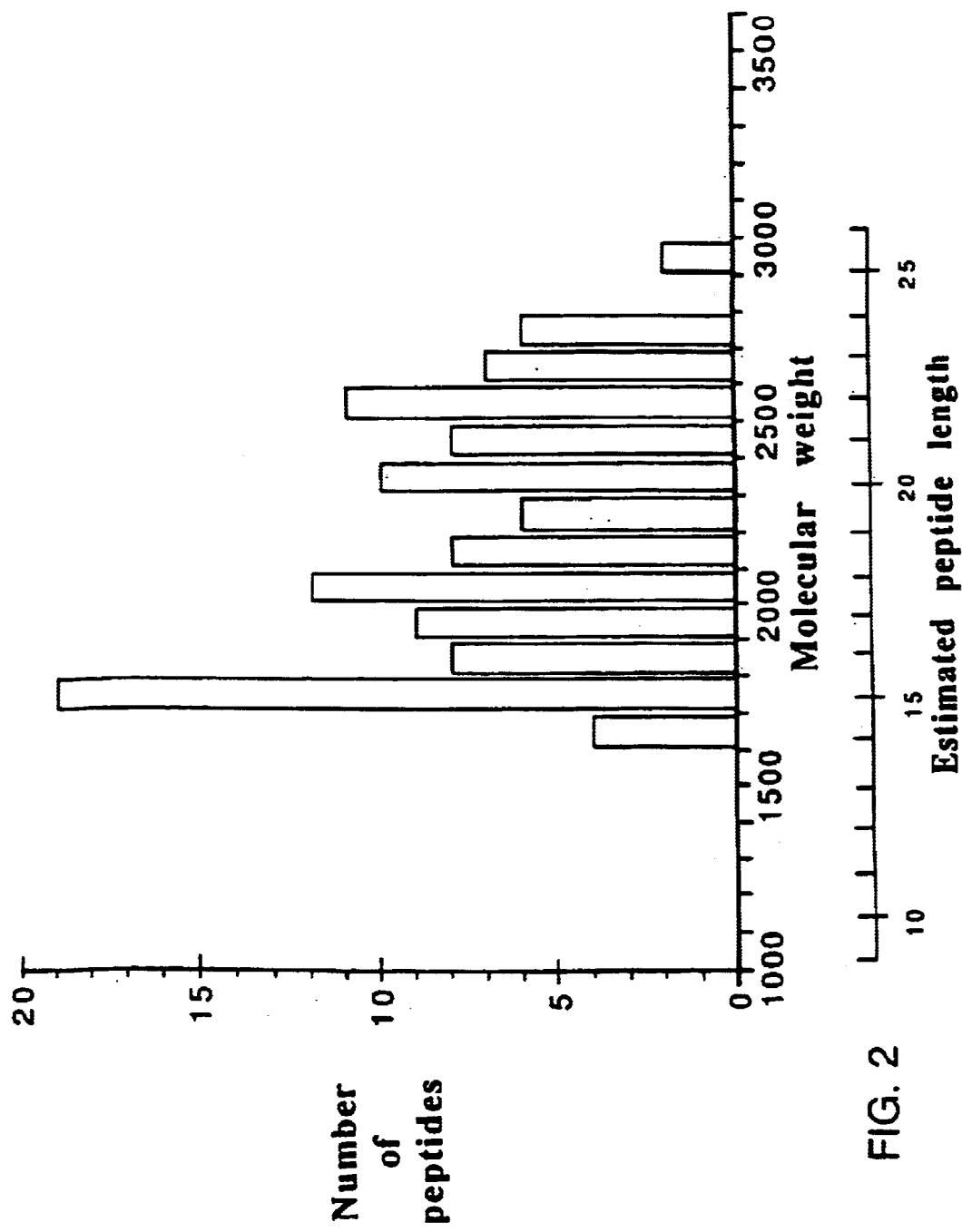

HLA-DR molecules were purified from homozygous, Epstein-Barr virus-transformed, human B lymphoblastoid lines: DR1 from LG-2 cells, DR2 from MST cells, DR3 from WT20 cells, DR4 from Priess cells, DR7 from Mann cells, and DR8 from 23.1 cells. All of these cell lines are publicly available. Cell growth, harvest conditions and protein purification were as previously described (Gorga, J. et al., 1991). Briefly, 200 grams of each cell type was resuspended in 10 mM Tris-HCl, 1 mM dithiothreitol (DTT), 0.1 mM phenylmethylsulfonylflouride (PMSF), pH 8.0, and lysed in a Thomas homogenizer. The nuclei were removed by centrifugation at 4000×g for 5 min and the pellets washed and repelleted until the supernatants were clear. All the supernatants were pooled and the membrane fraction harvested by centrifugation at 175,000×g for 40 min. The pellets were then resuspended in 10 mM Tris-HCl, 1 mM DTT, 1 mM PMSF, 4% NP-40. The unsolubilized membrane material was removed by centrifugation at 175,000×g for 2 hours, and the NP-40 soluble supernatant fraction used in immunoaffinity purification.

Detergent soluble HLA-DR was bound to a LB3.1-protein A SEPHAROSE™ agarose gel column (Pharmacia) (Gorga et al., id) and eluted with 100 mM glycine, pH 11.5. Following elution, the sample was immediately neutralized by the addition of Tris-HCl and then dialyzed against 10 mM Tris-HCl, 0.1% deoxycholic acid (DOC). The LB3.1 monoclonal antibody recognizes a conformational determinant present on the nonpolymorphic HLA-DRα chain, and thus recognizes all allotypes of HLA-DR.

The transmembrane domain of the DR molecules was removed by papain digestion, and the resulting water-soluble molecule further purified by gel filtration chromatography on an S-200 column equilibrated in 10 mM Tris-HCl, pH 8.0. The purified DR samples were concentrated by ultrafiltration, yield determined by BCA assay, and analyzed by SDS polyacrylamide gel electrophoresis.

II. Extraction and Fractionation of Bound Peptides

Water-soluble, immunoaffinity-purified class II molecules were further purified by high-performance size exclusion chromatography (SEC), in 25 mM N-morpholino ethane sulfonic acid (MES) pH 6.5 and a flowrate of 1 ml/min., to remove any residual small molecular weight contaminants. Next, CENTRICON™ ultrafiltration microconcentrators (molecular weight cutoff 10,000 daltons) (Amicon Corp.) were sequentially washed using SEC buffer and 10% acetic acid prior to spin-concentration of the protein sample (final volume between 100–200 μl). Peptide pools were extracted from chosen class II alleles by the addition of 1 ml of 10% acetic acid for 15 minutes at 70° C. These conditions are sufficient to free bound peptide from class II molecules, yet mild enough to avoid peptide degradation. The peptide pool was separated from the class II molecule after centrifugation through the CENTRICON™ ultrafiltration microconcentrator, with the flow-through containing the previously bound peptides.

The collected acid-extracted peptide pool was concentrated in a SPEED-VAC™ vacuum equipped centrifluge (Savant) prior to HPLC separation. Peptides were separated on a microbore C-18 reversed-phase chromatography (RPC) column (Vydac) utilizing the following non-linear gradient protocol at a constant flowrate of 0.15 ml/min.: 0–63 min. 5%–33% buffer B; 63–95 min. 33%–60% buffer B; 95–105 min 60%–80% buffer B, where buffer A was 0.06% trifluoroacetic acid/water and buffer B was 0.055% trifluoroacetic acid/acetonitrile. Chromatographic analysis was monitored at multiple UV wavelengths (210, 254, 277, and 292 nm) simultaneously, permitting spectrophotometric evaluation prior to mass and sequence analyses. Shown in FIG. 1 are chromatograms for each of the six DR peptide pools analyzed.

Collected fractions were subsequently analyzed by mass spectrometry and Edman sequencing.

III. Analysis of Peptides

The spectrophotometric evaluation of the peptides during RPC provides valuable information regarding amino acid composition (contribution of aromatic amino acids) and is used as a screening method for subsequent characterization. Appropriate fractions collected during the RPC separation were next analyzed using a Finnegan-MAT LASERMAT™ matrix-assisted laser-desorption mass spectrometer (MALD-MS) to determine the individual mass values for the predominant peptides. Between 1%–4% of the collected fraction was mixed with matrix (1 μl α-Cyano-4-hydroxycinnamic acid) to achieve mass determination of extracted peptides. The result of this analysis for HLA-DR1 is shown in FIG. 2. Next, chosen peptide samples were sequenced by automated Edman degradation microsequencing using an ABI 477A protein sequencer (Applied Biosystems) with carboxy-terminal verification provided by mass spectral analysis using the Finnigan-MAT TSQ 700 triple quadruple mass spectrometer equipped with an electro-spray ion source. This parallel analysis ensures complete identity of peptide composition and sequence. Peptide alignment with protein sequences stored in the SWISS-PROT database was performed using the FASTA computer database search program. Set forth in Tables 1–10 are the results of this sequence analysis for each of the DR molecules studied.

RESULTS

I. HLA-DR1

The HLA-DR1 used in this study was papain solubilized to enable the material to be used both for crystallographic and bound peptide analyses. The peptides bound to DR1 were acid extracted and fractionated using RPC. (FIG. 1). The absence of any detectable peptidic material following a second extraction/RPC separation verified quantitative peptide extraction. Amino acid analysis (ABI 420A/130A derivatizer/HPLC) of extracted peptide pools demonstrated a 70–80% yield, assuming total occupancy of purified DR1 with a molar equivalent of bound peptides corresponding to the size distribution determined by mass spectrometry (see FIG. 2). The RPC profiles obtained from DR1 extractions of multiple independent preparations were reproducible. Furthermore, profiles from either detergent-soluble or papain-solubilized DR1 were equivalent. To confirm that the peptides were in fact identical in detergent-soluble and papain-digested DR1, mass spectrometry and Edman sequencing analyses were performed and revealed identical masses and sequences for analogous fractions from the two preparations.

Matrix-assisted laser desorption mass spectrometry (MALD-MS) was used to identify 111 species of unique mass contained within the eluted peptide pool of DR1 with an average size of 18 and a mode of 15 residues (FIG. 2). Over 500 additional mass species present within the molecular weight range of 13–25 residues were detected; however, the signal was not sufficient to assign individual masses with confidence. Multiple species of varying mass were detected in fractions corresponding to single RPC peaks indicating co-elution of peptides. To characterize these peptides further, samples were analyzed in parallel on a triple quadruple mass spectrometer equipped with an electrospray ion source (ESI-MS) and by automated Edman degradation microsequencing (Lane et al., J. Prot. Chem. 10:151–160 (1991)). Combining these two techniques permits crucial verification of both the N- and C-terminal amino acids of peptides contained in single fractions. The sequence and mass data acquired for twenty peptides isolated from DR1 are listed in Table 1. All the identified peptides aligned with complete identity to regions of proteins stored in the SWISS-PROT database.

Surprisingly, sixteen of the twenty sequenced DR1-bound peptides were 100% identical to regions of the self proteins HLA-A2 and class II-associated invariant chain (Ii), representing at least 26% of the total extracted peptide mass. These isolated peptides varied in length and were truncated at both the N- and C-termini, suggesting that: 1) antigen processing occurs from both ends after binding to DR1, or 2) class II molecules bind antigen from a pool of randomly generated peptides. The yields from the peptide microsequencing indicated that HLA-A2 (FIG. 1) and Ii each represents at least 13% of the total DR1-bound peptides.

An additional surprising finding concerned a peptide which, although bound to HLA-DR and 100% homologous with HLA-A2 peptide, was derived from a cell which does not express HLA-A2 protein. Evidently this peptide is derived from a protein containing a region homologous with a region of HLA-A2 protein. Thus, for purposes of this specification, the term "HLA-A2 protein" is intended to include HLA-A2 protein itself, as well as any naturally occurring protein which contains a ten or greater amino acid long region of >80% homology with an HLA-DR-binding peptide derived from HLA-A2. An "HLA-A2 peptide" similarly refers to peptides from any HLA-A2 protein, as broadly defined herein.

The other four peptides identified in the DR1 studies were derived from two self proteins, transferrin receptor and the $Na^+/K^+$ ATPase, and one exogenous protein, bovine serum fetuin (a protein present in the serum used to fortify the medium which bathes the cells). Each of these peptides occupied only 0.3–0.6% of the total DR1 population, significantly less than either the HLA-A2 or the Ii peptides. It is known that class II molecules en route to the cell surface intersect the pathway of incoming endocytic vesicles. Both recycling membrane proteins and endocytosed exogenous protein travel this common pathway. Hence, the HLA-A2, transferrin receptor, $Na^+/K^+$ ATPase and bovine fetuin derived peptides would all encounter DR1 in a similar manner. Ii associates with nascent class II molecules in the endoplasmic reticulum (ER) (Jones et al., Mol. Immunol. 16:51–60 (1978)), preventing antigen binding until the class II/Ii complex arrives at an endocytic compartment (Roche and Cresswell, Nature 345:615–618 (1990)), where Ii undergoes proteolysis (Thomas et al., J. Immunol. 140:2670–2675 (1988); Roche and Cresswell, Proc. Natl. Acad. Sci. USA 88:3150–3154 (1991)), thus allowing peptide binding to proceed. Presumably, the Ii peptides bound to DR1 were generated at this step.

Synthetic peptides corresponding to five of the peptides reported in Table 1 were made and their relative binding affinities to DR1 determined. The influenza A hemagglutinin peptide (HA) 307–319 (SEQ ID NO: 24) has been previously described as a high affinity, HLA-DR1 restricted peptide (Roche and Cresswell, J. Immunol. 144:1849–1856 (1990); Rothbard et al., Cell 52:515–523 (1988)), and was thus chosen as the control peptide. "Empty" DR1 purified from insect cells expressing recombinant DR1 cDNA was used in the binding experiments because of its higher binding capacity and 10-fold faster association kinetics than DR1 isolated from human cells (Stern and Wiley, Cell 68:465–477 (1992)). All the synthetic peptides were found to compete well (Ki<100 nM) against the HA peptide (Table 2). At first approximation, the Ii 107–120 peptide (SEQ ID NO: 156) had the highest affinity of all the competitor peptides measured, equivalent to that determined for the control HA peptide. In addition to the Ki determinations, these peptides were found to confer resistance to SDS-induced α-β chain dissociation of "empty" DR1 when analyzed by SDS-PAGE, indicative of stable peptide binding (Sadegh-Nasseri and Germain, Nature 353:167–170 (1991); Dornmair et al., Cold Spring Harbor Symp. Quant. Biol. 54:409–415 (1989); Springer et al., J. Biol. Chem. 252:6201–6207 (1977)). Neither of the two control peptides, $β_2$m 52–64 (SEQ ID NO: 26) nor Ii 97–111 (SEQ ID NO: 25), was able to either confer resistance to SDS-induced chain dissociation of DR1 or compete with HA 307–319 (SEQ ID NO: 24) for binding to DR1; both of these peptides lack the putative binding motif reported in this study (see below).

A putative DR1 binding motif based on the sequence alignments of the core epitopes (the minimum length) of certain naturally processed peptides is shown in Table 3. The peptides listed in this table include those determined herein for HLA-DR1, as well as a number of peptides identified by others and known to bind DR1 (reference #6 in this table being O'Sullivan et al., J. Immunol. 145:1799–1808, 1990; reference #17, Roche & Cresswell, J. Immunol. 144:1849–1856, 1990; reference #25, Guttinger et al., Intern. Immunol. 3:899–906, 1991; reference #27, Guttinger et al. EMBO J. 7:2555–2558, 1988; and reference #28, Harris et al., J. Immunol. 148:2169–2174, 1992). The key residues proposed in the motif are as follows: a positively charged group is located at the first position, referred to here as the index position for orientation (I); a hydrogen bond donor is located at I+5; and a hydrophobic residue is at I+9. In addition, a hydrophobic residue is often found at I+1 and/or I−1. Every naturally processed peptide sequenced from DR1 conforms to this motif (with the exception of the HLA-A2 peptide 103–116 (SEQ ID NO: 3) that lacks residue I+9). Because the putative motif is not placed in a defined position with respect to the first amino acid and because of the irregular length of bound peptides, it is impossible to deduce a motif from sequencing of peptide pools, as was done for class I molecules (Falk et al., Nature 351:290–296 (1991)). The Ii 97–111 peptide (SEQ ID NO: 25), a negative control peptide used in binding experiments, has the I and I+5 motif residues within its sequence, but is missing eight additional amino acids found in Ii 106–119 (SEQ ID NO: 16) (Table 3C).

A sequence comparison of 35 previously described DR1-binding synthetic peptides (O'Sullivan et al., J. Immunol. 145:1799–1808 (1990); Guttinger et al., Intern. Immunol. 3:899–906 (1991); Hill et al., J. Immunol. 147:189–197 (1991); Guttinger et al., EMBO J. 7:2555–2558 (1988); Harris et al., J. Immunol. 148:2169–2174 (1992)) also supports this motif. Of the 35 synthetic peptides, 21 (60%) have the precise motif, nine (30%) contain a single shift at either I or I+9, and the remaining five (10%) have a single substitution at I (Table 3B and C). Interestingly, in the latter peptides, a positive charge at I is always replaced by a large hydrophobic residue (Table 8C); a pocket has been described in class I molecules that can accommodate this precise substitution (Latron et al., Proc. Natl. Acad. Sci. USA 88:11325–11329 (1991)). Contributions by the other eight amino acids within the motif or the length of the peptide have not been fully evaluated and may compensate for shifted/missing residues in those peptides exhibiting binding. Evaluation of the remaining 117 non-DR1 binding peptides cited in those studies (which peptides are not included in Table 3) indicates that 99 (85%) of these peptides do not contain the DR1 motif proposed herein. Of the remaining 18 peptides (15%) that do not bind to DR1 but which do contain the motif, 6 (5%) are known to bind to other DR allotypes; the remaining 12 peptides may have unfavorable interactions at other positions which interfere with binding.

In contrast to the precise N-terminal cleavages observed in the previous study of six peptides bound to the mouse class II antigen termed I-A$^b$ and five bound to mouse I-E$^b$ (Rudensky et al., Nature 3563:622–627 (1991)), the peptides bound to DR1 are heterogeneous at both the N- and C-termini. In contrast to peptides bound to class I molecules, which are predominantly nonamers (Van Bleek and Nathenson, Nature 348:213–216 (1990); Rotzschke et al., Nature 348:252–254 (1990); Jardetzky et al., Nature 353:326–329 (1991); Hunt et al., Science 255:1261–1263 (1992)), class II peptides are larger and display a high degree of heterogeneity both in length and the site of terminal truncation, implying that the mechanisms of processing for class I and class II peptides are substantially different. Furthermore, the present results suggest that class II processing is a stochastic event and that a DR allotype may bind peptides of different lengths from a complex random mixture. The heterogeneity observed may be solely due to protection of bound peptides from further degradation. Thus, class II molecules would play an active role in antigen processing (as previously proposed (Donermeyer and Allen, J. Immunol. 142:1063–1068 (1989)) by protecting the bound peptides from complete degradation. Alternatively, the predominance of 15mers bound to DR1 (as detected by both the MALD-MS and the yields of sequenced peptides) could be the result of trimming of bound peptides. In any event, the absence of detectable amounts of peptides shorter than 13 and longer than 25 residues suggests that there are length constraints intrinsic either to the mechanism of peptide binding or to antigen processing. The predominance of peptides bound to DR1 that are derived from endogenously synthesized proteins, and particularly MHC-related proteins, may result from the evolution of a mechanism for presentation of self peptides in connection with the generation of self tolerance.

II. Other HLA-DR Molecules

The sequences of naturally processed peptides eluted from each of DR2, DR3, DR4, DR7 and DR8 are shown in Tables 4–8, respectively. In addition to those peptides shown in Table 4, it has been found that DR2 binds to long fragments of HLA-DR2a β-chain and HLA-DR2b β-chain, corresponding to residues 1–126 or 127 of each of those proteins. Presumably, only a short segment of those long fragments is actually bound within the groove of DR2, with the remainder of each fragment protruding from one or both ends of the groove. Table 9 gives sequences of DR1 from another cell line which does not have wild-type Ar, but which has bound A2-like peptides. Table 10 gives sequences of peptides eluted from DR4 and DR11 molecules expressed in cells from a human spleen. These data demonstrate the great prevalence of self peptides bound, compared to exogenous peptides. The data also show that the A2 and Ii peptides occur repeatedly. In addition, certain of the Tables include peptides that appear to derive from viral proteins, such as Epstein-Barr virus major capsid protein, which are likely to be present in the cells studied.

III. Peptide Delivery

Genetic Constructions.

In order to prepare genetic constructs for in vivo administration of genes encoding immunomodulatory peptides of the invention, the following procedure is carried out.

Overlapping synthetic oligonucleotides were used to generate the leader peptide/blocking peptide mini-genes illustrated in FIG. 3 by PCR amplification from human HLA-DRα and invariant chain cDNA templates. These mini-genes encode the Ii peptide fragments KMRMATPLLMQALPM (or Ii$_{15}$; SEQ ID NO: 15) and LPKPPKPVSKMRMATPLLMQALPM (or Ii$_{24}$; SEQ ID NO: 7). The resulting constructs were cloned into pGEM-2 (Promega Corp.) to form the plasmids pGEM-2-α-Ii$_{15}$ and pGEM-2-α-Ii$_{24}$, with an upstream T7 promoter for use in the in vitro transcription/translation system described below.

For in vivo expression, each mini-gene was subsequently subcloned from the pGEM-2 derivatives into a transfection vector, pHβactin-1-neo (Gunning et al., (1987) Proc. Natl.

Acad. Sci. U.S.A. 84:4831), to form the plasmids pHβactin-α-Ii$_{15}$ and pHβactin-α-Ii$_{24}$. The inserted mini-genes are thus expressed in vivo from the constitutive/strong human β actin promoter. In addition, the mini-genes were subcloned from the pGEM-2 derivatives into the vaccinia virus recombination vector pSC11 (S. Chakrabarti et al. (1985) Mol. Cell. Biol. 5, 3403–3409) to form the plasmids pSC11-α-Ii$_{15}$ and pSC11-α-Ii$_{24}$. Following recombination into the viral genome the inserted mini-genes are expressed from the strong vaccinia P$_{7.5}$ promoter.

Intracellular Trafficking Signals Added to Peptides.

Short amino acid sequences can act as signals to target proteins to specific intracellular compartments. For example, hydrophobic signal peptides are found at the amino terminus of proteins destined for the ER, while the sequence KFERQ (SEQ ID NO: 153) (and other closely related sequences) is known to target intracellular polypeptides to lysosomes, while other sequences target polypeptides to endosomes. In addition, the peptide sequence KDEL (SEQ ID NO: 152) has been shown to act as a retention signal for the ER. Each of these signal peptides, or a combination thereof, can be used to traffic the immunomodulating peptides of the invention as desired. For example, a construct encoding a given immunomodulating peptide linked to an ER-targeting signal peptide would direct the peptide to the ER, where it would bind to the class II molecule as it is assembled, preventing the binding of intact Ii which is essential for trafficking. Alternatively, a construct can be made in which an ER retention signal on the peptide would help prevent the class II molecule from ever leaving the ER. If instead a peptide of the invention is targeted to the endosomic compartment, this would ensure that large quantities of the peptide are present when invariant chain is replaced by processed peptides, thereby increasing the likelihood that the peptide incorporated into the class II complex is the high-affinity peptides of the invention rather than naturally-occurring, potentially immunogenic peptides. The likelihood of peptides of the invention being available incorporation into class II can be increased by linking the peptides to an intact Ii polypeptide sequence. Since Ii is known to traffic class II molecules to the endosomes, the hybrid Ii would carry one or more copies of the peptide of the invention along with the class II molecule; once in the endosome, the hybrid Ii would be degraded by normal endosomal processes to yield both multiple copies of the peptide of the invention or molecules similar to it, and an open class II binding cleft. DNAs encoding immunomodulatory peptides containing targeting signals will be generated by PCR or other standard genetic engineering or synthetic techniques, and the ability of these peptides to associate with DR molecules will be analyzed in vitro and in vivo, as described below.

It is proposed that the invariant chain prevents class II molecules from binding peptides in the ER and may contribute to heterodimer formation. Any mechanism that prevents this association would increase the effectiveness of class II blockade. Therefore, a peptide corresponding to the site on Ii which binds to the class II heterodimer, or corresponding to the site on either the α or β subunit of the heterodimer which binds to Ii, could be used to prevent this association and thereby disrupt MHC class II function.

In Vitro Assembly.

Cell free extracts are used routinely for expressing eukaryotic proteins (Krieg, P. & Melton, D. (1984) Nucl. Acids Res. 12, 7057; Pelham, H. and Jackson, R. (1976) Eur. J. Biochem. 67, 247). Specific mRNAs are transcribed from DNA vectors containing viral RNA polymerase promoters (Melton, D. et al. (1984) Nucl. Acids Res. 12, 7035), and added to micrococcal nuclease-treated cell extracts. The addition of $^{35}$S methionine and amino acids initiates translation of the exogenous mRNA, resulting in labeled protein. Proteins may be subsequently analyzed by SDS-PAGE and detected by autoradiography. Processing events such as signal peptide cleavage and core glycosylation are initiated by the addition of microsomal vesicles during translation (Walter, P. and Blobel, G. (1983), Meth. Enzymol., 96, 50), and these events are monitored by the altered mobility of the proteins in SDS-PAGE gels.

The ability of peptides containing a signal peptide sequence to be accurately processed and to compete with invariant chain for class II binding in the ER are assayed in the in vitro system described above. Specifically, DR1 α- and β-chain and invariant chain peptide constructs described above are transcribed into mRNAs, which will be translated in the presence of mammalian microsomal membranes. Association of the DR heterodimer with Ii is determined by immunoprecipitation with antisera to DR and Ii. Addition of mRNA encoding the peptide of the invention to the translation reaction should result in a decreased level of coimmunoprecipitated Ii, and the concomitant appearance of coimmunoprecipitated peptide, as determined by SDS-PAGE on TRIS-Tricine gels. These experiments will provide a rapid assay system for determining the potential usefulness of a given blocking peptide as a competitor for Ii chain binding in the ER. Those peptides of the invention which prove to be capable of competing successfully with Ii in this cell-free assay can then be tested in intact cells, as described below.

In Vivo Assembly.

Human EBV-transformed B cell lines LG-2 and HOM-2 (homozygous for HLA-DR1) and the mouse B cell hybridoma LK35.2 are transfected with either 50 μg of linearized pHβactin-α-Ii$_{15}$ or pHβactin-α-Ii$_{24}$ or (as a control) pHβactin-1-neo by electroporation (150 mV, 960 μF, 0.2 cm cuvette gap). Following electroporation, the cells are cultured in G418-free medium until total recovery (approximately 4 days). Each population is then placed under G418 selection until neomycin-expressing resistant populations of transfectants are obtained (approximately 1–2 months). The resistant populations are subcloned by limiting dilution and the clonality of stable transfectants determined by PCR amplification of blocking peptide mRNA expression.

Stable transfectants of LG-2 and HOM-2 carrying blocking peptide mini-genes or negative control vectors are grown in large-scale culture conditions until 20 grams of pelleted cell mass is obtained. The HLA-DR expressed by each transfectant is purified, and the bound peptide repertoire (both from within the cell and from the cell surface) analyzed as described above. Successful demonstration of a reduction in the total bound peptide diversity will be conclusive evidence of intracellular delivery of immunomodulatory peptides.

A second cell-based assay utilizes stable transfectants of LK35.2 cells carrying blocking peptide mini-genes or negative control vectors; these cells are used as APCs in T cell proliferation assays. Each transfectant is cultured for 24 hours in the presence of different dilutions of hen egg lysozyme (HEL) and HEL-specific T cell hybridomas. The relative activation of the T cells present in each assay (as measured by lymphokine production) is determined using the publicly available lymphokine dependent cell line CTLL2 in a $^{3}H$-thymidine incorporation assay (Vignali et al. (1992) J.E.M. 175:925–932). Successful demonstration of a reduction in the ability of blocking peptide expressing transfectants to present HEL to specific T cell hybridomas will be conclusive evidence of intracellular delivery of immuno-modulatory peptides. Cells of the human TK⁻ cell line 143 (ATCC) are infected with vaccinia virus (strain WR, TK⁺) (ATCC), and two hours postinfection, pSC11-α-$Ii_{15}$ or pSC11-α-$Ii_{24}$ or pSC11 is introduced into the infected cells by calcium phosphate precipitation. TK⁻ recombinants are selected for with bromodeoxyuridine at 25 μg/ml. Recombinant plaques are screened by PCR for the presence of mini-gene DNA. Recombinant virus is cloned by three rounds of limiting dilution to generate pure clonal viral stocks.

In experiments analogous to the transfection experiments described above, recombinant vaccinia viruses encoding mini-genes or vector alone will be used to infect large-scale cultures of the human EBV transformed B cell lines LG-2 and HOM-2. Following infection, the HLA-DR is purified and the bound peptide repertoire analyzed as described above. A reduction of the complexity of the bound peptide population and a significant increase in the relative amount of Ii peptides bound are conclusive evidence that vaccinia can deliver blocking peptides to human APCs.

The same recombinant vaccinia viruses encoding mini-genes or vector will be used to infect mice experiencing experimentally-induced autoimmunity. A number of such models are known and are referred in Kronenberg, Cell 65:537–542 (1991).

Liposomal Delivery of Synthetic Peptides or Mini-gene Constructs.

Liposomes have been successfully used as drug carriers and more recently in safe and potent adjuvant strategies for malaria vaccination in humans (Fries et al. (1992), Proc. Natl. Acad. Sci. USA 89:358). Encapsulated liposomes have been shown to incorporate soluble proteins and deliver these antigens to cells for both in vitro and in vivo CD8⁺ mediated CTL response (Reddy et al., J. Immunol. 148:1585–1589, 1992; and Collins et al., J. Immunol. 148:3336–3341, 1992). Thus, liposomes may be used as a vehicle for delivering synthetic peptides into APCs.

Harding et al. (Cell (1991) 64, 393–401) have demonstrated that the targeting of liposome-delivered antigen to either of two intracellular class II-loading compartments, early endosomes and/or lysosomes, can be accomplished by varying the membrane composition of the liposome: acid-sensitive liposomes were found to target their contents to early endosomes, while acid-resistant liposomes were found to deliver their contents to lysosomes. Thus, the peptides of the invention will be incorporated into acid-sensitive liposomes where delivery to endosomes is desired, and into acid-resistant liposomes for delivery to lysosomes.

Liposomes are prepared by standard detergent dialysis or dehydration-rehydration methods. For acid-sensitive liposomes, dioleoylphosphatidylethanolamine (DOPE) and palmitoylhomocystein (PHC) are utilized, while dioleoylphospatidylcholine (DOPC) and dioleoylphosphatidylserine (DOPS) are used for the preparation of acid-resistant liposomes. $10^{-5}$ mol of total lipid (DOPC/DOPS or DOPE/PHC at 4:1 mol ratios) are dried, hydrated in 0.2 ml of HEPES buffered saline (HBS) (150 mM NaCl, 1 mM EGTA, 10 mM HEPES pH 7.4) and sonicated. The lipid suspensions are solubilized by the addition of 0.1 ml of 1 M octylglucoside in HBS. The peptides to be entrapped are added to 0.2 ml of 0.6 mM peptide in 20% HBS. The mixture is then frozen, lyophilized overnight, and rehydrated. These liposomes will be treated with chymotrypsin to digest any surface-bound peptide. Liposome delivery to EBV-transformed cell lines (as described above) will be accomplished by 12–16 hour incubation at 37° C. HLA-DR will be purified from the liposome treated cells and bound peptide analyzed as above.

Alternatively, the liposomes are formulated with the DNA mini-gene constructs of the invention, and used to deliver the constructs into APCs either in vitro or in vivo.

Human immunization will be carried out under the protocol approved by both The Johns Hopkins University Joint Committee for Clinical Investigation and the Human Subject Research Review Board of the Office of the Surgeon General of the U.S. Army (Fries et al. (1992), Proc. Natl. Acad. Sci. U.S.A. 89:358–362), using dosages described therein, or other dosages described in the literature for liposome-based delivery of therapeutic agents.

Delivery Via Immune-stimulating Complexes (ISCOMS).

ISCOMS are negatively charged cage-like structures of 30–40nm in size formed spontaneously on mixing cholesterol and Quil A (saponin). Protective immunity has been generated in a variety of experimental models of infection, including toxoplasmosis and Epstein-Barr virus-induced tumors, using ISCOMS as the delivery vehicle for antigens (Mowat and Donachie) Immunology Today 12:383–385, 1991. Doses of antigen as low as 1 μg encapsulated in ISCOMS have been found to produce class I mediated CTL responses, where either purified intact HIV-1-IIIB gp 160 envelope glycoprotein or influenza hemagglutinin is the antigen (Takahashi et al., Nature 344:873–875, 1990). Peptides are delivered into tissue culture cells using ISCOMS in a manner and dosage similar to that described above for liposomes; the class II peptide binding of delivered peptides are then determined by extraction and characterization as described above. ISCOM-delivered peptides of the invention which are effectively utilized by cultured cells are then tested in animals or humans.

In addition to delivery of the therapeutic synthetic peptides, ISCOMS could be constituted to deliver the mini-gene constructs to APCs, and thus serve as an alternative to the above-outlined vaccinia strategy.

Immunogenic Peptide Delivery (Vaccines).

In addition to using the above-described intracellular delivery systems to deliver nonimmunogenic self peptides with the specific aim of down-modulating the immune system (thus alleviating autoimmune conditions), the delivery systems of the invention may alternatively be used as a novel means of vaccination, in order to stimulate a portion of the immune system of an animal. In the latter context, the delivery system is employed to deliver, into appropriate cells, DNA constructs which express immunogenic, pathogen-derived peptides intended to stimulate an immune response against a specific pathogen. Because the antigenic peptide is produced inside the target cell itself, the vaccine method of the invention ensures that there is no circulating free antigen available to stimulate antibody formation and thereby induce potentially deleterious or inappropriate immunological reactions. The immune response stimulated by vaccines of the invention is, because the vaccines are targeted solely to APC's, limited to the T cell mediated response, in contrast to standard vaccine protocols which result in a more generalized immune response. Although some of the peptide-presenting APC's will initially be lysed by host T cells, such lysis will be limited because, inter alia, the virus-based vaccine is non-replicative, i.e., each carrier virus can infect only one cell.

The model antigen that will be used to perfect and test the system of the invention is hen egg lysozyme (HEL). It is arguably the most well characterized protein for antigen presentation studies, to which there are numerous monoclonal antibodies and class I- and class II-restricted mouse T cell clones and hybridomas. The primary epitopes that will be studied are the peptide HEL 34–45, as both monoclonal antibodies and CD4+ T cell hybridomas are available, and peptide HEL 46–61, as both class I and class II-restricted T cell clones and hybridomas have been raised and are publicly available. These two sequences are thus proven immunogenic epitopes. Initially, four constructs encoding different polypeptides are analyzed: (a) whole, secreted HEL, (B) HEL 34–45, (c) HEL 46–61, and (d) HEL 34–61. The last three include a signal sequence known to be cleaved in these cells, e.g., IA$^k$ (MPRSRALILGVLALTTMLSLCGG; SEQ ID NO:274), which would result in targeting to the ER. All constructs are then subcloned into pHβApr-1 neo. The methodology for making these constructs is similar to that outlined above. The constructs are introduced into appropriate APCs, e.g., LK35.2 cells, by means of a conventional eukaryotic transfection or one of the delivery vehicles discussed above (e.g., vaccinia, liposomes, or ISCOMS). LK35.2 cells, which possess the mouse MHC Class II restriction molecules IA$^k$ and IE$^k$, transfected with each of the constructs are tested for their ability to stimulate the appropriate class I and class II-restricted T cell hybridomas and clones using standard techniques. Whether class I stimulation is observed will depend on whether peptide trimming can occur in the ER, in order to produce an 8–10-mer suitable for binding to class I molecules. If these constructs are ineffective for class I stimulation, they can be modified in order to produce a more effective peptide for class I binding. If these constructs prove to be less effective for class II-restricted responses, they can be tagged with endosomal and/or lysosomal targeting sequences as discussed in Section V.

The effectiveness of targeting signals used to direct immunogenic peptides to particular intracellular organelles would be monitored using electron microscopic analysis of immunogold stained sections of the various transfectants. Rabbit anti-peptide antisera would be produced and affinity purified for this application. In addition, monoclonal antibody HF10, which recognizes HEL 34–45, will be used.

Once a construct is defined that can be effectively presented by transfectants in vitro, its effectiveness in vivo will be determined. This can be tested by injection of the transfectants i.p. and/or s.c. into C3H/Balb/c F1 mice, or by injection of the construct incorporated into an appropriate delivery vehicle (e.g., liposome, ISCOMS, retrovirus, vaccinia). Optimal protocols and doses for such immunizing injections can be determined by one of ordinary skill in the art, given the disclosures provided herein. Efficiency of immunization can be tested by standard methods such as (a) proliferation of class II-restricted T cells in response to HEL pulsed APCs, (b) CTL response to $^{51}$Cr-labeled targets, and (c) serum antibody titre as determined by ELISA.

Once the details of the vaccine delivery system of the invention are optimized, constructs encoding peptides with useful immunizing potential can be incorporated into the system. Such peptides can be identified by standard means now used to identify immunogenic epitopes on pathogen-derived proteins. For example, candidate peptides for immunization may be determined from antibody and T cell analysis of animals infected with a particular pathogen. In order to obtain a protective and effective anamnestic response, the peptides used for vaccination should ideally be those which are presented with the highest frequency and efficiency upon infection. This could best be determined by using the procedures outlined in the experimental section above to extract and characterize the peptides bound by MHC class II molecules from infected cells. Given allelic restriction of immunogenic peptides (in contrast to the observed degenerate binding of self peptides of invention), a mini-gene encoding several immunogenic peptides will probably be required to provide a vaccine useful for the entire population. Vaccine administration and dosage are as currently employed to smallpox vaccination.

TABLE 1

LG-2/HLA–DR1 BINDING PEPTIDES

| PROTEIN SOURCE | POSITION | SEQUENCE | SEQ ID NO. | LENGTH | FRACTION | MW | MASS SPEC | YIELD |
|---|---|---|---|---|---|---|---|---|
| Pseudo HLA–A2 | 103–120 | VGSDWRFLRGYHQYAYDG | 1 | 18 | DR1S-59 | 2190.4 | 2190.4 | 39.5 |
| | 103–117 | VGSDWRFLRGYHQYA | 2 | 15 | DR1S-58 | 1855.0 | 1854.4 | 907.5 |
| | 103–116 | VGSDWRFLRGYHQY | 3 | 14 | DR1S-58 | 1784.0 | 1783.6 | 53.3 |
| | 104–117 | GSDWRFLRGYHQYA | 4 | 14 | DR1S-56 | 1755.3 | 1755.2 | 96.5 |
| | 105–117 | SDWRFLRGYHQYA | 5 | 13 | DR1S-56 | 1698.2 | 1698.8 | 48.8 |
| Invariant Chain (Ii) | 98–122 | LPKPPKPVSKMRMATPLLMQALPMG | 6 | 25 | DR1S-88 | 2733.5 | 2734.5 | 40.5 |
| | 98–121 | LPKPPKPVSKMRMATPLLMQALPM | 7 | 24 | DR1S-88 | 2676.4 | 2675.9 | 80.8 |
| | 99–122 | PKPPKPVSKMRMATPLLMQALPMG | 8 | 24 | DR1S-86 | 2620.Z | 2619.7 | 91.5 |
| | 98–120 | LPKPPKPVSKMRMATPLLMQALP | 9 | 23 | DR1S-86 | 2545.2 | 2544.5 | 112.2 |
| | 99–121 | PKPPKPVSKMRMATPLLMQALPM | 10 | 23 | DR1S-87 | 2563.2 | 2562.3 | 145.0 |
| | 100–121 | KPPKPVSKMRMATPLLMQALPM | 11 | 22 | DR1S-87 | 2466.1 | 2465.8 | 101.5 |
| | 99–120 | PKPPKPVSKMRMATPLLMQALP | 12 | 22 | DR1S-84 | 2432.0 | 2431.7 | 72.5 |
| | 100–120 | KPPKPVSKMRMATPLLMQALP | 13 | 21 | DR1S-84 | 2334.9 | 2334.2 | 31.6 |
| | 100–120 | PPKPVSKMRMATPLLNQALP | 14 | 20 | DR1S-86 | 2206.7 | 2207.4 | 89.8 |
| | 107–121 | KMRMATPLLMQALPM | 15 | 15 | DR1S-88 | 1732.2 | 1731.9 | 178.5 |
| | 107–120 | KMRMATPLLMQALP | 16 | 14 | DR1S-86 | 1601.0 | 1600.2 | 162.0 |
| Na+/K+ ATPase | 199–216 | IPADLRIISANGCKVDNS | 17 | 18 | DR1S-56 | 1886.6 | 1885.8 | 48.8 |
| Transferrin Recpt. | 680–696 | RVEYHFLSPYVSPKESP | 18 | 17 | DR1S-58 | 2035.3 | 2036.8 | 30.3 |
| Bovine Fetuin | 56–74 | YKHTLNQIDSVKVWPRRPT | 19 | 19 | DR1S-51 | 2237.6 | 2236.5 | 69.0 |
| | 56–73 | YKHTLNQIDSVKVWPRRP | 20 | 18 | DR1S-50 | 2338.7 | 2338.5 | 32.5 |
| HLA–DR β–chain | 43–61 | DVGEYRAVTELGRPDAEYW | 21 | 19 | DR1S-51 | 2226.5 | ? | |
| Carboxypeptidase E | 101–115 | EPGEPEFKYIGNMHG | 22 | 15 | DR1S-48 | 1704.9 | 1700.4* ESI-MS | |

TABLE 2

PEPTIDE BINDING TO MLA-DR1

| PEPTIDE[a] | SEQ ID NO. | LENGTH | Ki vs HA 307–319[b] nM | SDS-Resistance[c] nM |
|---|---|---|---|---|
| HLA-A2 103–117 | 2 | 15 | 49 ± 3 | + |
| Ii 106–120 | 15 | 15 | <10 | + |
| Ii 98–121 | 7 | 24 | 33 ± 5 | + |
| Na+/K+ ATPase 199–216 | 17 | 18 | 68 ± 9 | + |
| Transf. Recept. 680–696 | 18 | 17 | <10 | + |
| Bovine Fetuin 56–72 | 23 | 19 | 66 ± 18 | + |
| HA 307–319 | 24 | 14 | <10 | + |
| Ii 97–111 | 25 | 15 | >10$^4$ | − |
| β$_2$m 52–64 | 26 | 13 | >10$^4$ | — |

[a] The first six entries correspond to peptides found associated with HLA-DR1 and the sequences are shown in Table 1. Two control peptides were also tested: β$_2$m 52–64, SDLSFSKDWSFYL (SEQ ID NO: 26), is from human β$_2$-microglobulin and Ii 97–111, LPKPPKPVSKMRMAT (SEQ ID NO: 25) is a truncated version of the longest invariant chain derived peptide isolated from HLA-DR1. Peptides were synthesized using solid-phase Fmoc chemistry, deprotected and cleaved using standrd methods, then purified by RPC. Purfied peptides were analyzed by mass spectrometry and concentrations were determined by quantitative ninhydrin analysis.
[b] Inhibition constants (Ki) were measured as the concentration of test peptide which inhibited 50% of the $^{125}$I-labeled HA 307–319 binding to "empty" HLA-DR1 produced in Sf9 insect cells (20). HA 307–319 was labeled using Na $^{125}$I and chloramine-T and isolated by gel filtration. Specific activity, determined by BCA assay (Pierce) and gamma counting, was 26,000 cpm/pmol. 10 nM labeled peptide and 10 nM purified HLA-DR1 were mixed with 10 different concentrations (10 nM to 10 μM) of synthetic cold competitor peptide in phosphate-buffered saline, pH 7.2, containing 1 mM EDTA, 1 mM PMSF, 0.1 mM iodoacetamide, and 3 mM NaN$_3$, and incubated at 37° C. for 85 hours. Free and bound peptfde were separated by native gel electrophoresis (33) and bound radioactivity was quantitated using a Fujix imaging plate analyzer (BAS 2000) after four hour exposures on the phospho-imaging plates. Percent inhibition was calculated as the ratio of background-corrected radioactivity in the sample to background-corrected radioactivity in a parallel sample containing no competitor peptide. Under these conditions, Ki measurements <10 nM could not be accurately determined.
[c] The ability of the synthetic peptides to confer resistance to SDS-induced chain dissociation of HLA-DR1 produced in insect cells was determined as described (20). Briefly, 20 μM HLA-DR1 was incubated with five-fold excess of synthetic peptide at 37° C. for 85 hours, in phosphate-buffered saline (pH 7.2) with the protease inhibitor mixture described above. After incubation, the samples were analyzed by SDS-PAGE with and without boiling prior to loading. Peptides which prevented SDS-induced chain dissociation are indicated positive (+) and those that did not negative (−).

TABLE 3

PUTATIVE HLA-DR1 PEPTIDE BINDING MOTIF

| | PROTEIN SOURCE | PEPTIDE SEQUENCE | SEQ ID NO | LENGTH | POSITION | REFERENCE |
|---|---|---|---|---|---|---|
| A | HLA-A2 | SDWRFLRGYHQYA | 5 | 13 | 105–117 | This study |
| | Invariant Chain | KMRMATPLLMQALP | 16 | 14 | 105–118 | |
| | Na+/K+ ATPase | IPADLRIISANGCKVDNS | 17 | 18 | 199–216 | |
| | Transferrin Receptor | RVEYHFLSPYVSPKESP | 18 | 17 | 680–696 | |
| | Bovine Fetuin | YKHTLNQIDSVKVWPRRP | 20 | 18 | 56–73 | |
| B | HEL | KVFGRCELAAAMKRHGLD | 27 | 18 | 1–18 | 6 |
| | | RNRCKGTDVQAWIRGCRL | 28 | 18 | 112–129 | 6 |
| | β$_2$m | HPPHIEIQMLKNGKKI | 29 | 16 | 31–46 | 6 |
| | PLA$_2$ | NELGRFKHTDACCRTH | 30 | 16 | 19–34 | 6 |
| | | SKPKVYQWFDLRKY | 31 | 14 | 115–128 | 6 |
| | NASE | ATSTKKLHKEPATLIKAIDG | 32 | 20 | 1–20 | 6 |
| | | PATLIKAIDGDTVKLMYKGQ | 33 | 20 | 11–30 | 6 |
| | | DRVKLMYKGQPMTFRLLLVD | 34 | 20 | 21–40 | 6 |
| | | VAYVYKPNNTHEQHLRKSEA | 35 | 20 | 111–130 | 6 |
| | HIV p13 | QKQEPIDKELYPLTSL | 36 | 16 | 97–112 | 6 |
| | HIV p17 | GARASVLSGGELDKWE | 37 | 16 | 1–16 | 6 |
| | Influenza HA | RTLYQNVGTYVSVGTSTLNK | 38 | 20 | 187–206 | 6 |
| | Influenza HA | PKYVKQNTLKLAT | 24 | 13 | 307–319 | 17 |
| | P. falcip. p190 | LKKLVFGYRKPLDNI | 39 | 15 | 249–263 | 25 |
| | P. falcip. CS | KHIEQYLKKIKNS | 40 | 13 | 329–341 | 27 |
| | Chicken OVA | DVFKELKVHHANENIF | 41 | 16 | 15–30 | 6 |
| | DR1 β chain | GDTRPRFLWQLKFECHFFNG | 42 | 20 | 1–20 | 28 |
| | | TERVRLLERCIYNQEESVRFDS | 43 | 22 | 21–42 | 28 |
| | | DLLEQRRAAVDTYCRHNYGVGESFT | 44 | 25 | 66–90 | 28 |
| | p Cyt c | KAERADLIAYLKQATAK | 45 | 17 | 88–104 | 6 |
| | Myelin basic prot. | GRTQDENPVVHFFKNIVTPRTPPP | 46 | 24 | 75–98 | 6 |
| C | Influenza Matrix | PLKAEIAQRLEDV | 47 | 13 | 19–31 | 6 |
| | HIV p17 | RQILGQLQPSLQTGSE | 48 | 16 | 57–72 | 6 |
| | β$_2$M | IQVYSRHPPENGKPNI | 49 | 16 | 7–22 | 6 |

TABLE 3-continued

PUTATIVE HLA-DR1 PEPTIDE BINDING MOTIF

| A PROTEIN SOURCE | PEPTIDE SEQUENCE | SEQ ID NO | LENGTH | POSITION | REFERENCE |
|---|---|---|---|---|---|
| PLA$_2$ | INTKCYKLEHPVTGCG | 50 | 16 | 85–100 | 6 |
| P. falcip p190 | YKLNFYFDLLRAKL | 51 | 14 | 211–224 | 25 |
|  | IDTLKKNENIKEL | 52 | 13 | 338–350 | 25 |
| DR1 β chain | DVGEYRAVTELGRPDAEYWN | 53 | 20 | 43–62 | 28 |
| HIV p17 | ERFAVNPGLLETSEGC | 54 | 16 | 41–56 | 6 |
| HEL | DNYRGYSLGNWVCAAKFESNFTQ | 55 | 23 | 20–42 | 6 |
| NASE | EALVRQGLAKVAYVYKPNNT | 56 | 20 | 101–120 | 6 |
| HIV p25 | PIVQNLQGQMVHQAIS | 57 | 16 | 1–16 | 6 |
|  | SALSEGATPQDLNTML | 58 | 16 | 41–56 | 6 |
| β$_2$m | SFYILAHTEFTPTETD | 59 | 16 | 61–76 | 6 |
| PLA$_2$ | KMYFNLINTKCYKLEH | 60 | 16 | 79–94 | 6 |

TABLE 4

MST/HLA-DR2 BINDING PEPTIES

| PROTEIN SOURCE | POSITION | SEQUENCE | SEQ ID NO. | LENGTH | FRACTION | MW | MASS SPEC |
|---|---|---|---|---|---|---|---|
| Pseudo HLA-A2 | 103–120 | VGSDWRFLRGYHQYAYDG | 1 | 18 | DR2-3-57 | 2190.4 | 2189.0 |
|  | 103–119 | VGSDWRFLRGYHQYAYAD | 61 | 17 | DR2-3-57 | 2133.3 | 2131.8 |
|  | 104–119 | GSDWRFLRGYHQYAYD | 62 | 16 | DR2-3-56 | 2034.3 | 2040.4 |
|  | 103–117 | VGSDWRFLRGYHQYA | 2 | 15 | DR2-3-56 | 1855.0 | 1858.5 |
|  | 103–116 | VGSDWRFLRGYHQY | 3 | 14 | DR2-3-56 | 1784.0 | 1786.3 |
|  | 104–117 | GSDWRFLRGYHQYA | 4 | 14 | DR2-3-55 | 1755.3 | 1755.0* |
|  | 105–117 | SDWRFLRGYHQYA | 5 | 13 | DR2-3-56 | 1698.2 | 1702.6 |
| Invariant Chain (Ii) | 98–121 | LPKPPKPVSKMRMATPLLMQALPM | 7 | 24 | DR2-3-70 | 2676.4 | 2675.0* |
|  | 99–121 | PKPPKPVSKMRMATPLLMQALPM | 10 | 23 | DR2-3-70 | 2563.2 | 2562.0* |
|  | 100–121 | KPPKPVSKMRMATPLLMQALPM | 11 | 22 | DR2-3-70 | 2466.1 | 2465.0* |
|  | 99–120 | PKPPKPVSKMRMATPLLMQALP | 12 | 22 | DR2-3-66 | 2432.0 | 2437.0 |
|  | 100–120 | KPPKPVSKMRMATPLLMQALP | 13 | 21 | DR2-3-66 | 2334.9 | 2340.0 |
|  | 101–120 | PPKPVSKMRMATPLLNQALP | 63 | 20 | DR2-3-70 | 2206.7 | 2207.0* |
|  | 107–125 | KMRMATPLLMQALPMGALP | 64 | 19 | DR2-3-71 | 2070.5 | 2074.3 |
|  | 107–121 | KMRMATPLLMQALPM | 15 | 15 | DR2-3-70 | 1732.2 | 1732.0* |
| HLA-DQ α-chain | 97–119 | NIVIKRSNSTAATNEVPEVTVFS | 158 | 23 | DR2-3-44 | 2476.8 | 2478.1 |
|  | 97–112 | NIVIKRSNSTAATNEV | 159 | 16 | DR2-3-41 | 1716.9 | 1717.0 |
| HLA-DQ β-chain | 42–59 | SDVGVYRAVTPQGRPDAE | 160 | 18 | DR2-3-41 | 1917.1 | 1920.5 |
|  | 43–59 | DVGVYRAVTPQGRPDAE | 161 | 17 | DR2-3-41 | 1830.0 | 1833.3 |
|  | 43–57 | DVGVYRAVTPQGRPD | 162 | 15 | DR2-3-41 | 1629.8 | 1632.9 |
| HLA-DR α-chain | 182–194 | APSPLPETTENVV | 163 | 13 | DR2-3-36 | 1353.5 | 1362.0 |
|  | 182–198 | APSPLPETTENVVCALG | 164 | 17 | DR2-3-41 | 1697.9 | 1701.0 |
| (MET) Kinase-relate trasforming protein | 59–81 | EHHIFLGATNYIYVLNEEDLQKV | 65 | 23 | DR2-3-65 | 2746.1 | 2746.6 |
| Guanylate-bind. | 434–450 | QELKNKYYQVPRKGIQA | 66 | 17 | DR2-3-71 | 2063.4 | 2074.3 |
| Mannose-bind. prot. | 174–193 | IQNLIKEEAFLGITDEKTEG | 67 | 20 | DR2-3-70 | 2248.5 | 2248.0* |
| Apolipoprotein B-100 | 1200–1220 | FPKSLHTYANILLDRRVPQTD | 165 | 21 | DR2-3-61 | 2484.8 | 2490.9 |
|  | 1200–1218 | FPKSLHTYANILLDRRVPQ | 166 | 19 | DR2-3-61 | 2268.6 | 2276.7 |
| Potassium channel prot | 173–190 | DGILYYYQSGGRLRRPVN | 167 | 18 | DR2-3-61 | 2127.4 | 2132.6 |
|  | 173–189 | DGILYYYQSGGRLRRPV | 168 | 17 | DR2-3-61 | 2013.3 | 2018.1 |
| Fibronectin receptor | 586–616 | LSPIHIALNFSLDPQAPVDSHGLRPALHYQ | 169 | 30 | DR2-3-61 | 3307.7 | 3313.1 |
| Factor VIII | 1175–1790 | LWDYGMSSSPHVLRNR | 170 | 16 | DR2-3-44 | 1918.2 | 1921.7 |
| HLA-DR2b β-chain | 94–111 | RVQPKVTVYPSKTQPLQH | 72 | 18 | DR2-3-39 | 2106.5 | 2114. |
|  | 94–108 | RVQPKVTVYPSKTQP | 73 | 15 | DR2-3-39 | 1728.3 | 1730.6 ESI.MS* MALD-MS |

TABLE 5

WT-2-/HLA-DR3 NATURALLY PROCESSED PEPTIDES

| Protein Source | Position | Sequence | SEQ ID NO. | Length | Fraction | MW | Mass Spec. |
|---|---|---|---|---|---|---|---|
| Pseudo HLA-A2 | 103–117 | VGSDWRFLRGYHQYA | 2 | 15 | DR3-2-63 | 1855.0 | 1863.9 |
| HLA-A30 | 28–? | VDDTQFVRFDSDAASQ . . . | 171 | ? | DR3-2-55 | ? | ? |
| HLA-DR α-chain | 111–129 | PPEVTVLTNSPVELREPNV | 172 | 19 | DR3-2-55 | 2090.4 | 2093.3 |
|  | 111–128 | PPEVTVLTNSPVELREPN | 173 | 18 | DR3-2-55 | 1991.2 | 1989.8 |
| HLA-DR β-chain | 1–? | GDTRPRFLEYSTSECHFF | 79 | 18 | DR3-2-73 | ? | ? |
| Acetylcholine recept. | 289–304 | VFLLLLADKVPETSLS | 174 | 16 | DR3-2-65 | 1745.1 | 1750.1 |
| Glucose-transport | 459–474 | TFDEIASGFRQGGASQ | 175 | 16 | DR3-2-55 | 1670.8 | 1672.6 |
| Sodium channel prot. | 384–397 | YGYTSYDTFSWAFL | 176 | 14 | DR3-2-41 | 1720.8 | 1720.5 |
| Invariant chain | 98–120 | LPKPPKPVSKMRMATPLLMQALP | 9 | 23 | DR3-2-73 | 2545.2 | 2554.0 |

TABLE 5-continued

WT-2-/HLA-DR3 NATURALLY PROCESSED PEPTIDES

| Protein Source | Position | Sequence | SEQ ID NO. | Length | Fraction | MW | Mass Spec. |
|---|---|---|---|---|---|---|---|
| (Ii) | 99–120 | PKPPKPVSKMRMATPLLMQALP | 12 | 22 | DR3-2-73 | 2432.0 | 2441.4 |
| | 100–120 | KPPKPVSKMRMATPLLMQALP | 13 | 21 | DR3-2-73 | 2334.9 | 2345.3 |
| | 132–150 | ATKYGNMTEDHVMHLLQNA | 177 | 19 | DR3-2-69 | 2173.4 | 2179.3 |
| CD45 | 1071–1084 | GQVKKNNHQEDKIE | 178 | 14 | DR3-2-41 | 1666.8 | 1667.0 |
| ICAM-2 | 64–76 | LNKILLDEQAQWK | 179 | 13 | DR3-2-51/52 | 1598.9 | 1602.4 |
| Interferon γ-receptor | 128–147 | GPPKLDIRKEEKQIMIDIFH | 180 | 21 | DR3-2-77 | 2505.0 | 2510.3 |
| | 128–148 | GPPKLDIRKEEKQIMIDIFHP | 181 | 20 | DR3-2-77 | 2407.8 | 2412.4 |
| IP-30 | 38–59 | SPLQALDFFGNGPPVNYKTGNL | 182 | 22 | DR3-2-77 | 2505.0 | 2510.3 |
| | 38–57 | SPLQALDFFGNGPPVNYKTG | 183 | 20 | DR3-2-77 | 2122.4 | 2124.2 |
| Cytochrome-b5 reduc. | 155–172 | GKFAIRPDKKSNPIIRTV | 184 | 18 | DR3-2-51/52 | 2040.4 | 2043.2 |
| EBV membrane antigen GP220 | 592–606 | TGHGARTSTEPTTDY | 185 | 15 | DR3-2-41 | 1593.6 | 1592.7 |
| EBV tegument protein membrane p140 | 1395–1407 | KELKRQYEKKLRQ | 186 | 13 | DR3-2-51/52 | 1747.1 | 1749.8 |
| Apolipoprotein B-100 (Human) | 1276–1295 | NFLKSDGRIKYTLNKNSLK | 74 | 20 | DR3-2-63 | 2352.9 | 2360.0 |
| | 1273–1292 | IPDNLFLKSDGRIKYTLNKN | 191 | 20 | DR3-2-65 | 2349.7 | 2354.6 |
| | 1273–1291 | IPDNLFLKSDGRIKYTLNK | 75 | 19 | DR3-2-63 | 2235.5 | 2245.1 |
| | 1273–1290 | IPDNLFLKSDGRIKYTLN | 192 | 18 | DR3-2-65 | 2107.4 | 2096.6 |
| | 1273–1289 | IPDNLFLKSDGRIKYTL | 193 | 17 | DR3-2-65 | 1993.3 | 2000.8 |
| | 1276–1291 | NLFLKSDGRIKYTLNK | 76 | 16 | DR3-2-60 | 1910.2 | 1911.4 |
| | 1276–1290 | NLFLKSDGRIKYTLN | 77 | 15 | DR3-2-60 | 1782.1 | 1785.9 |
| | 1207–1224 | YANILLDRRVPQTDMTF | 78 | 17 | DR3-2-63 | 2053.3 | 2059.1 |
| | 1794–1810 | VTTLNSDLKYNALDLTN | 194 | 17 | DR3-2-69 | 1895.1 | 1896.5 MALD-MS |

TABLE 6

PRIESS/HLA-DR4 NATURALLY PROCESSED PEPTIDES

| PROTEIN SOURCE | POSITION | SEQUENCE | SEQ ID NO. | LENGTH | FRACTION | MW | MASS SPEC |
|---|---|---|---|---|---|---|---|
| Ig Kappa Chain C region (Human | 188–208 | KHKVYACEVTHQGLSSPVTKS | 80 | 21 | DR4-2-45 | 2299.6 | 2304.0 |
| | 188–207 | KHKVYACEVTHQGLSSPVTK | 81 | 20 | DR4-2-47 | 2212.5 | 2213.0 |
| | 189–206 | HKVYACEVTHQGLSSPVT | 82 | 18 | DR4-2-43 | 1955.5 | 1952.1 |
| | 188–204 | KHKVYACEVTHQGLSSP | 83 | 17 | DR4-2-45 | 1883.1 | 1882.8 |
| | 187–203 | EKHKVYACEVTHQGLSS | 84 | 17 | DR4-2-45 | 1915.1 | 1922.5 |
| | 188–203 | KHKVYACEVTHQGLSS | 85 | 16 | DR4-2-54 | 1787.0 | 1787.0 |
| | 189–204 | HKVYACEVTHQGLSSP | 86 | 16 | DR4-2-47 | 1755.0 | 1767.8 |
| | 187–202 | EKHKVYACEVTHQGLS | 87 | 16 | DR4-2-43 | 1828.0 | 1822.8 |
| | 188–202 | KHKVYACEVTHQGLS | 88 | 15 | DR4-2-51 | 1699.9 | 1708.3 |
| | 189–203 | HKVYACEVTHQGLSS | 89 | 15 | DR4-2-45 | 1657.8 | 1667.0 |
| | 187–200 | EKHKVYACEVTHQG | 90 | 14 | DR4-2-51 | 1628.8 | 1632.6 |
| HLA-DR α-chain | 182–198 | APSPLPETTENVVCALG | 91 | 17 | DR4-2-43 | 1697.9 | 1700 |
| HLA-A2 | 28–50 | VDDTQFVRFDSDAASQRMEPRAP | 195 | 23 | DR4-2-58 | 2638.6 | 2641.6 |
| | 28–48 | VDDTQFVRFDSDAASQRMEPR | 92 | 21 | DR4-2-56 | 2470.6 | 2472.9 |
| | 28–47 | VDDTQFVRFDSDAASQRMEP | 93 | 20 | DR4-2-59 | 2314.5 | 2319.3 |
| | 28–46 | VDDTQFVRFDSDAASQRME | 94 | 19 | DR4-2-54 | 2217.2 | 2218.7 |
| | 30–48 | DTQFVRFDSDAASQRMEPR | 95 | 19 | DR4-2-55 | 2256.4 | 2263.2 |
| | 31–49 | TQFVRFDSDAASQRMEPRA | 96 | 19 | DR4-2-56 | 2212.4 | 2211.5 |
| | 28–44 | VDDTQFVRFDSDAASQR | 97 | 17 | DR4-2-55 | 1957.0 | 1963.1 |
| | 31–47 | TQFVRFDSDAASQRMEP | 98 | 17 | DR4-2-56 | 1985.1 | 1987.5 |
| | 31–45 | TQFVRFDSDAASQRM | 99 | 15 | DR4-2-54 | 1758.9 | 1761.0 |
| | 31–42 | TQFVRFDSDAAS | 100 | 12 | DR4-2-54 | 1343.4 | 1343.3 |
| HLA-C | 28–50 | VDDTQFVRFDSDAASPRGEPRAP | 101 | 23 | DR4-2-56 | 2533.7 | 2536.7 |
| | 31–52 | TQFVRFDSDAASPRGEPRAPWV | 102 | 22 | DR4-2-54 | 2489.7 | 2491.5 |
| | 28–48 | VDDTQFVRFDSDAASPRGEPR | 103 | 21 | DR4-2-54 | 2365.5 | 2368.1 |
| | 28–47 | VDDTQFVRFDSDAASPRGEP | 104 | 20 | DR4-2-56 | 2209.3 | 2211.5 |
| | 28–46 | VDDTQFVRFDSDAASPRGE | 105 | 19 | DR4-2-56 | 2112.2 | 2113.9 |
| HLA-Cw9 | 28–45 | VDDTQFVRFDSDAASPRG | 106 | 18 | DR4-2-56 | 1983.1 | 1987.5 |
| | 31–48 | TQFVRFDSDAASPRGEPR | 107 | 18 | DR4-2-52 | 2036.2 | 2041.5 |
| | 28–44 | VDDTQFVRFDSDAASPR | 108 | 17 | DR4-2-55 | 1926.1 | 1931.7 |
| | 30–46 | DTQFVRFDSDAASPRGE | 109 | 17 | DR4-2-52 | 1897.9 | 1901.6 |
| | 31–44 | TQFVRFDSDAASPR | 110 | 14 | DR4-2-52 | 1596.7 | 1603.7 |
| | 31–42 | TQFVRFDSDAAS | 111 | 12 | DR4-2-54 | 1343.4 | 1343.3 |
| HLA-C | 130–150 | LRSWTAADTAAQITQRKWEAA | 112 | 21 | DR4-2-56 | 2374.5 | 2376.4 |
| | 129–147 | DLRSWTAADTAAQITQRKW | 197 | 19 | DR4-2-58 | 2218.4 | 2220.1 |
| | 130–147 | LRSWTAADTAAQITQRKW | 198 | 18 | DR4-2-58 | 2103.3 | 2105.0 |
| | 129–145 | DLRSWTAADTAAQITQR | 113 | 17 | DR4-2-59 | 1904.5 | 1908.7 |
| | 129–144 | DLRSWTAADTAAQITQ | 114 | 16 | DR4-2-59 | 1747.9 | 1752.3 |
| | 129–143 | DLRSWTAADTAAQIT | 115 | 15 | DR4-2-59 | 1619.7 | 1622.2 |

TABLE 6-continued

PRIESS/HLA-DR4 NATURALLY PROCESSED PEPTIDES

| PROTEIN SOURCE | POSITION | SEQUENCE | SEQ ID NO. | LENGTH | FRACTION | MW | MASS SPEC |
|---|---|---|---|---|---|---|---|
| HLA-Bw62 | 129–150 | DLSSWTAADTAAQITQRKWEAA | 199 | 22 | DR4-2-65 | 2420.6 | 2422.7 |
|  | 129–145 | DLSSWTAADTAAQITQR | 116 | 17 | DR4-2-60 | 1834.9 | 1838.1 |
|  | 129–146 | DLSSWTAADTAAQITQRK | 200 | 18 | DR4-2-65 | 1963.1 | 1966.3 |
|  | 129–148 | DLSSWTAADTAAQITQRKWE | 117 | 20 | DR4-2-66 | 2278.4 | 2284.6 |
| VLA-4 | 229–248 | GSLFVYNITTNKYKAFLDKQ | 201 | 20 | DR4-2-65 | 2350.7 | 2352.6 |
|  | 229–244 | GSLFVYNITTNKYKAF | 202 | 16 | 0R4-2-65 | 1866.1 | 1868.2 |
| PAI-1 | 261–281 | AAPYEKEVPLSALTNILSAQL | 203 | 21 | DR4-2-65 | 2228.5 | 2229.5 |
|  | 261–278 | AAPYEKEVPLSALTNILS | 204 | 18 | DR4-2-65 | 1916.2 | 1917.4 |
| Cathepsin C | 151–167 | YDHNFVKAINADQKSWT | 118 | 17 | DR4-2-70 | 2037.2 | 2039.6 |
| (Rat Homologue) |  | I | 119 |  |  | 2035.3 |  |
|  | 151–166 | YDHNFVKAINADQKSW | 120 | 16 | DR4-2-70 | 1936.1 | 1937.7 |
|  |  | I | 121 |  |  | 1934.2 |  |
| Bovine Hemoglobin | 26–41 | AEALERMFLSFPTTKT | 205 | 16 | DR4-2-78 | 1842.1 | 1836.1 |
| HLA-DQ3.2 β-chain | 24–38 | SPEDFVYQFKGMCYF | 206 | 15 | DR4-2-78 | 1861.1 | 1861.7 |
| HLA-DR β-chain | 1–? | GDTRPRFLEQVKHE . . . | 122 | 14 | DR4-2-72 | 1711.9 |  |
| IG Heavy Chain | 121–? | GVYFYLQWGRSTLVSVS . . . | 123 | (?) | DR4-2-6 | ? | ? |
|  |  |  |  |  |  |  | MALD-MS |

TABLE 7

MANN/HLA-DR7 NATURALLY PROCESSED PEPTIDES

| PROTEIN SOURCE | POSITION | SEQUENCE | SEQ ID NO. | LENGTH | FRACTION | MW | MASS SPEC |
|---|---|---|---|---|---|---|---|
| Pseudo HLA-A2 | 105–124 | SDWRFLRGYHQYAYDGKDYI | 207 | 20 | DR7-2-61 | 2553.8 | 2556.5 |
|  | 103–120 | VGSDWRFLRGYHQYAYDG | 1 | 18 | DR7-2-63 | 2190.4 | 2194 |
|  | 103–117 | VGSDWRFLRGYHQYA | 2 | 15 | DR7-2-63 | 1855.0 | 1860 |
|  | 104–117 | GSDWRFLRGYHQYA | 208 | 14 | DR7-2-61 | 1755.9 | 1760.8 |
|  | 104–116 | GSDWRFLRGYHQY | 209 | 13 | DR7-2-61 | 1684.8 | 1687.6 |
|  | 105–117 | SDWRFLRGYHQYA | 210 | 13 | DR7-2-61 | 1698.9 | 1704.1 |
| HLA-A29 | 234–253 | RPAGDGTFQKWASVVVPSGQ | 124 | 20 | DR7-2-66 | 2087.3 | 2092 |
|  | 234–249 | RPAGDGTFQKWASVVV | 125 | 16 | DR7-2-63 | 1717 | 1718 |
|  | 237–258 | GDGTFQKWASVVVPSGQEQRYT | 126 | 22 | DR7-2-66 | 2436 | 2440 |
|  | 237–254 | GDGTFQKWASVVVPSGQE | 127 | 18 | DR7-2-66 | 1892.3 | 1892 |
|  | 239–252 | GTFQKWASVVVPSG | 128 | 14 | DR7-2-66 | 1462 | 1465 |
|  | 239–253 | GTFQKWASVVVPSGQ | 129 | 15 | DR7-2-66 | 1718 | 1721 |
|  | 239–261 | GTFQKWASVVVPSGQEQRYTCHV | 130 | 23 | DR7-2-66 | 2603 | 2606 |
| HLA-B44 | 83–99 | RETQISKTNTQTYRENL | 211 | 17 | DR7-2-35 | 2082.3 | 2086.1 |
|  | 83–98 | RETQISKTNTQTYREN | 212 | 16 | DR7-2-35 | 1969.1 | 1971.1 |
|  | 83–97 | RETQISKTNTQTYRE | 213 | 15 | DR7-2-35 | 1855.9 | 1857.3 |
| HLA-DR α-chain | 101–126 | RSNYTPITNPPEVTVLTNSPVELREP | 214 | 26 | DR7-2-35 | 2924.2 | 2926.9 |
|  | 58–78 | GALANIAVDKANLEIMTKRSN | 131 | 21 | DR7-2-66 | 2229.5 | 2221 |
|  | 182–200 | APSPLPETTENVVCALGLTV | 215 | 20 | DR7-2-42 | 1912.2 | 1917.7 |
| HLA-DQ α-chain | 179–? | SLQSPITVEWRAQSESAQSKMLSGIGGFVL | 216 | ? | DR7-2-35 | ? | ? |
| 4F2 Cell-surface | 318–338 | VTQYLNATGNRWCSWSLSQAR | 217 | 21 | DR7-2-71 | 2441.7 | 2445.1 |
| antigen heavy chain | 318–334 | VTQYLNATGNRWCSWSL | 218 | 17 | DR7-2-71 | 1999.2 | 2001.9 |
| LIF receptor | 854–866 | TSILCYRKREWIK | 219 | 13 | DR7-2-35 | 1696.0 | 1700.8 |
| Ig kappa chain C reg. | 188–201 | KHKVYACEVTHQGL | 220 | 14 | DR7-2-61 | 1612.9 | 1615.6 |
|  | 188–200 | KHKVYACEVTHQG | 221 | 13 | DR7-2-61 | 1498.7 | 1501.0 |
| Invariant Chain | 99–120 | PKPPKPVSKMRMATPLLMQALP | 12 | 22 | DR7-2-72 | 2432.0 | 2436.6 |
| (Ii) | 100–120 | KPPKPVSKMRMATPLLNQALP | 13 | 21 | DR7-2-72 | 2334.9 | 2339.7 |
| K channel protein | 492–516 | GDMYPKTWSGMLVGALCALAGVLTI | 222 | 25 | DR7-2-71 | 2567.1 | 2567.3 |
| Heat shock cognate | 38–54 | TPSYVAFTDTERLIGDA | 132 | 17 | DR7-2-69 | 1856.9 | 1856.6 |
| 71 KD protein |  |  |  | 17 | DR7-2-72 | 1856.0 | 1857.0 |
|  | 38–52 | TPSYVAFTDTERLIG | 133 | 15 | DR7-2-69 | 1669.8 | 1671.9 |
| Complement C9 | 465–483 | APVLISQKLSPIYNLVPVK | 223 | 19 | DR7-2-61 | 2019.5 | 2083.9 |
| Thromboxane-A | 406–420 | PAFRFTREAAQDCEV | 224 | 15 | DR7-2-71 | 1739.9 | 1743.0 |
| synthase |  |  |  |  |  |  |  |
| EBV major capsid prot | 1264–1282 | VPGLYSPCRAFFNKEELL | 225 | 18 | DR7-2-54 | 2082.4 | 2081.2 |
|  | 1264–1277 | VPGLYSPCRAFFNK | 226 | 14 | DR7-2-54 | 1597.9 | 1598.6 |
| Apolipoprotein B-100 | 1586–1608 | KVDLTFSKQHALLCSDYQADYES | 227 | 23 | DR7-2-54 | 2660.9 | 2662.5 |
|  | 1586–1600 | KVDLTFSKQHALLCS | 228 | 15 | DR7-2-54 | 1689.0 | 1687.7 |
|  | 1942–1954 | FSHDYRGSTSHRL | 229 | 13 | DR7-2-42 | 1562.7 | 1567.5 |
|  | 2077–2089 | LPKYFEKKRNTII | 230 | 13 | DR7-2-61 | 1650.0 | 1653.8 |
|  |  |  |  |  |  |  | MALD-MS |

TABLE 8

23.1/HLA-DR8 NATURALLY PROCESSED PEPTIDES

| PROTEIN SOURCE | POSITION | SEQUENCE | SEQ ID NO. | LENGTH | FRACTION | MW | MASS SPEC |
|---|---|---|---|---|---|---|---|
| HLA-DR α-chain | 158–180 | SETVFLPREDHLFRKFHYLPFLP | 231 | 23 | DR8-3-59 | 2889.3 | 2889.0 |
|  | 182–198 | APSPLPETTENVVCALG | 232 | 17 | DR8-3-41 | 1697.9 | 1704.3 |
| HLA-DR β-chain | 1–? | GDTRPRFLEYSTGECYFFNGTERV | 233 | ? | DR8-3-75 | — | — |
| HLA-DP β-chain | 80–92 | RHNYELDEAVTLQ | 234 | 13 | DR8-3-76 | 1587.7 | 1591.3 |
| LAM Blast-1 with | 88–108 | DPQSGALYISKVQKEDNSTYI | 235 | 21 | DR8-3-54 | 2543.6 | 2549.1 |
| N-acetyglucosamine | 92–108 | GALYISKVQKEDNSTYI | 236 | 17 | DR8-3-52 | 2116.1 | 2118.0 |
|  | 129–146 | DPVPKPVIKIEKIEDMDD | 237 | 18 | DR8-3-57 | 2081.4 | 2085.7 |
|  | 129–143 | DPVPKPVIKIEKIED | 238 | 15 | DR8-3-57 | 1720.0 | 1724.9 |
| Ig kappa chain | 63–80 | FTFTISRLEPEDFAVYYC | 239 | 18 | DR8-3-57 | 2201.5 | 2203.6 |
|  | 63–77 | FTFTISRLEPEDFAV | 240 | 15 | DR8-3-57 | 1772.0 | 1777.0 |
| LAR protein | 1302–1316 | DPVEMRRLNYQTPG | 241 | 14 | DR8-3-76 | 1675.9 | 1679.8 |
| LIF receptor | 709–726 | YQLLRSMIGYIEELAPIV | 242 | 18 | DR8-3-66 | 2108.5 | 2112.0 |
| IFN-α receptor | 271–287 | GNHLYKWKQIPDCENVK | 243 | 17 | DR8-3-66 | 2072.4 | 2075.1 |
| Interleukin-8 receptor | 169–188 | LPFFLFRQAYHPNNSSPVCY | 244 | 20 | DR8-3-59 | 2400.7 | 2402.5 |
| Metalloproteinase inhibitor 2 | 187–214 | QAKFFACIKRSDGSCAWYRGAAPPKQEF | 245 | 28 | DR8-2-63 | 3161.6 | 3164.9 |
|  | 187–205 | QAKFFACIKRSDGSCAWYR | 246 | 19 | DR8-3-63 | 2235.5 | 2233.6 |
| Metalloproteinase inhibitor 1 | 101–118 | NRSEEFLIAGKLQDGLLH | 134 | 18 | DR8-3-66 | 2040.3 | 2042.9 |
|  | 101–117 | SEEFLIAGKLQDGLL | 135 | 16 | DR8-3-70 | 1789.0 | 1799.9 |
|  | 103–117 | SEEFLIAGKLQDGLL | 247 | 15 | DR8-3-72 | 1632.9 | 1646.0 |
|  | 101–112 | NRSEEFLIAGKL | 248 | 12 | DR8-3-66 | 1376.6 | 1381.8 |
| Cathepsin E | 89–112 | QNFTVIFDTGSSNLWVPSVYCTSP | 249 | 24 | DR8-3-59 | 2662.9 | 2664.4 |
| Cathepsin S | 189–205 | TAFQYIIDNKGIDSDAS | 68 | 17 | DR8-3-63 | 1857.9 | 1857.1 |
| Cystatin SN | 41–58 | DEYYRRLLRVLRAREQIV | 250 | 18 | DR8-3-63 | 2448.7 | 2348.0 |
| Tubulin α-chain | 207–223 | EAIYDICRRNLDIERPT | 251 | 17 | DR8-3-63 | 2077.3 | 2078.3 |
|  | 207–219 | EAIYDICRRNLDI | 252 | 13 | DR8-3-63 | 1593.8 | 1595.1 |
| Myosin β-heavy chain | 1027–1047 | HELEKIKKQVEQEKCEIQAAL | 253 | 21 | DR8-3-59 | 2493.9 | 2494.0 |
| Ca release channel | 2614–2623 | RPSMLQHLLR | 254 | 10 | DR8-3-68 | 1250.5 | 1254.8 |
| CD35 | 359–380 | DDFMGQLLNGRVLFPVNLQLGA | 255 | 22 | DR8-3-72 | 2417.8 | 2421.3 |
| CD75 | 106–122 | IPRLQKIWKNYLSMNKY | 256 | 17 | DR8-3-66 | 2195.6 | 2202.1 |
| c-myc transfor. prot. | 371–385 | KRSFFALRDQIPDL | 257 | 14 | DR8-3-68 | 1706.0 | 1709.6 |
| K-ras trasnfor. prot. | 164–180 | RQYRLKKISKEEKTPGC | 258 | 17 | DR8-3-54 | 2064.4 | 2066.5 |
| Calcitonin receptor (Hum?) | 38–53 | EPFLYILGKSRVLEAQ | 69 | 16 | DR8-3-78 | 1863.2 | 1848.4 |
| α-ENOLASE (?) | 23–? | AEVYHDVMSEFF . . . | 259 | ? | DR8-3-54 | — | — |
| Plasminogen activator inhibitor-1 | 378–396 | DRPFLFVVRHNPTGTVLFM | 260 | 19 | DR8-3-59 | 2246.7 | 2247.1 |
|  | 133–148 | MPHFFRLFRSTVKQVD | 261 | 16 | DR8-3-70 | 2008.4 | 2116.4 |
| Apolipoprotein B-100 | 1724–1743 | KNIFHFKVNQEGLKLSNDMM | 262 | 20 | DR8-3-62 | 2393.8 | 2399.4 |
|  | 1724–1739 | KNIFHFKVNQEGLKLS | 263 | 16 | DR8-3-57 | 1902.2 | 1903.7 |
|  | 1780–1799 | YKQTVSLDIQPYSLVTTLNS | 264 | 20 | DR8-3-54 | 2271.5 | 2273.7 |
|  | 2646–2662 | STPEFTILNTLHIPSFT | 265 | 17 | DR8-3-80 | 1918.2 | 1929.4 |
|  | 2647–2664 | TPEFTILNTLHIPSFTID | 266 | 18 | DR8-3-80 | 2059.3 | 2073.5 |
|  | 2647–2662 | TPEFTILNTLHIPSFT | 267 | 16 | DR8-3-80 | 1831.1 | 1841.6 |
|  | 2885–2900 | SNTKYFHKLNIPQLDF | 268 | 16 | DR8-3-68 | 1965.2 | 1969.9 |
|  | 2072–2088 | LPFFKFLPKYFEKKRNT | 269 | 17 | DR8-3-75 | 2203.6 | 2207.0 |
|  | 2072–2086 | LPFFKFLPKYFEKKR | 270 | 15 | DR8-3-76 | 1988.4 | 1992.6 |
|  | 4022–4036 | WNFYYSPQSSPDKKL | 271 | 15 | DR8-3-59 | 1860.0 | 1863.3 |
| Bovine Transferrin | 261–281 | DVIWELLNHAQEHFGKDKSKE | 272 | 21 | DR8-3-76 | 2523.8 | 2524.9 |
|  | 261–275 | DVIWELLINHAQEHFG | 273 | 15 | DR8-3-78 | 1808.0 | 1818.1 |
|  | 261–273 | DVIWELLNHAQEH | 196 | 13 | DR8-3-73 | 1603.8 | 1608.8 |
| von Willebrand factor | 617–636 | IALLLMASQEPQRMSRNFVR | 190 | 20 | DR8-3-59 | 2360.8 | 2359.7 |
|  | 617–630 | IALLLMASQEPQRM | 189 | 14 | DR8-3-59 | 1600.9 | 1601.3 |
|  |  |  |  |  |  |  | MALD-MS |

TABLE 9

HOM2/HLA-DR1 NATURALLY PROCESSED PEPTIDES

| PROTEIN SOURCE | POSITION | SEQUENCE | SEQ ID NO. | LENGTH | FRACTION | MW | MASS SPEC |
|---|---|---|---|---|---|---|---|
| Pseudo HLA-A2 | 103–117 | VGSDWRFLRGYHQYA | 2 | 15 | H2/DR1-1-64 | 1855.0 | 1854.4 |
|  | 104–117 | GSDWRFLRGYHQYA | 4 | 14 | H2/DR1-1-63 | 1755.3 | 1755.2 |
| Invariant Chain (Ii) | 98–121 | LPKPPKPVSKMRMATPLLMQALPM | 7 | 24 | H2/DR1-1-77 | 2676.4 | 2675.9 |
|  | 99–122 | PKPPKPVSKMRMATPLLMQALPMG | 8 | 24 | H2/DR1-1-72 | 2620.2 | 2619.7 |
|  | 98–120 | LPKPPKPVSKMRMATPLLMQALP | 9 | 23 | H2/DR1-1-73 | 2545.2 | 2544.5 |
|  | 99–121 | PKPPKPVSKMRMATPLLMQALPM | 10 | 23 | H2/DR1-1-75 | 2563.2 | 2562.3 |
|  | 100–121 | KPPKPVSKMRMATPLLMQALPM | 11 | 22 | H2/DR1-1-75 | 2466.1 | 2465.8 |
|  | 99–120 | PKPPKPVSKMRMATPLLMQALP | 12 | 22 | H2/DR1-1-72 | 2432.0 | 2431.7 |
|  | 100–120 | KPPKPVSKMRMATPLLMQALP | 13 | 21 | H2/DR1-1-72 | 2334.9 | 2334.2 |
|  |  |  |  |  |  |  | ESI-MS |

TABLE 10

SUMMARY OF NATURALLY PROCESSSED PEPTIDES BOUND TO HLA-DR EXPRESSED IN NORMAL HUMAN SPLEEN

| PROTEIN SOURCE | POSITION | SEQUENCE | SEQ ID NO. | LENGTH | MW | MASS SPEC |
| --- | --- | --- | --- | --- | --- | --- |
| HLA-DR α-chain | 71/133–156 | SETVFLPREDHLFRKFHYLPFLPS | 140 | 24 | 2976 | 2982 |
| | 71/136–156 | VFLPREDHLFRKFHYLPFLPS | 141 | 21 | 2659 | 2666 |
| | 71/136–155 | VFLPREDHLFRKFHYLPFLP | 142 | 20 | 2572 | 2579 |
| | 71/136–151 | VFLPREDHLFRKFHYL | 143 | 16 | 1118 | 2126 |
| Calgranulin B | 33/25–33 | KLGHPDTLN | 144 | 9 | 994 | 999 |
| | 42/88–114 | WASHEKMHEGDEGPGHHHKPGLGEGTP | 145 | 27 | 2915 | 2927 |
| | 43/88–114 | WASHEKMHEGDEGPGHHHKPGLGEGTP | 146 | 27 | 2017 | 2926 |
| HLA-B51 | 42/104–121 | GPDGRLLRGHNQYDGK | 188 | 16 | 2017 | 2023 |
| Kinase C ξ chain (rat) | 42/341–446 | TLPPFQPQITDDYGLD | 70 | 16 | 1704 | 1705 |
| HLA-DR4 β chain | 45/129–144 | VRWFRNGQEEKTGVVS | 71 | 16 | 1892 | 1894 MALD-MS |

---

What is claimed is:

1. A purified preparation of a peptide having an amino acid sequence identical to that of a naturally processed and presented segment of a naturally-occurring human invariant chain (Ii) protein, said peptide being 10 to 30 residues in length, inclusive, wherein said peptide comprises residues 108–117 of Ii (SEQ ID NO: 151).

2. The preparation of claim 1, wherein said peptide consists of SEQ ID NO: 151.

3. A liposome containing a peptide having an amino acid sequence identical to that of a naturally processed and presented segment of a naturally-occurring human invariant chain (Ii) protein, said peptide being 10 to 30 residues in length, inclusive, wherein said peptide comprises residues 108–117 of Ii (SEQ ID NO:151).

4. The liposome of claim 3, wherein said peptide consists of SEQ ID NO: 151.

5. An immune-stimulating complex (ISCOM) comprising a peptide having an amino acid sequence identical to that of a naturally processed and presented segment of a naturally-occurring human invariant chain (Ii) protein, said peptide being 10 to 30 residues in length, inclusive, wherein said peptide comprises residues 108–117 of Ii (SEQ ID NO:151).

6. The ISCOM of claim 5, wherein said peptide consists of SEQ ID NO: 151.

7. The preparation of claim 1, wherein the peptide comprises residues 98–122 of Ii (SEQ ID NO:6).

8. The preparation of claim 1, wherein the peptide comprises residues 98–121 of Ii (SEQ ID NO:7).

9. The preparation of claim 1, wherein the peptide comprises residues 99–122 of Ii (SEQ ID NO:8).

10. The preparation of claim 1, wherein the peptide comprises residues 98–120 of Ii (SEQ ID NO:9).

11. The preparation of claim 1, wherein the peptide comprises residues 99–121 of Ii (SEQ ID NO:10).

12. The preparation of claim 1, wherein the peptide comprises residues 100–121 of Ii (SEQ ID NO:11).

13. The preparation of claim 1, wherein the peptide comprises residues 99–120 of Ii (SEQ ID NO:12).

14. The preparation of claim 1, wherein the peptide comprises residues 100–120 of Ii (SEQ ID NO:13).

15. The preparation of claim 1, wherein the peptide comprises residues 107–121 of Ii (SEQ ID NO:15).

16. The preparation of claim 1, wherein the peptide comprises residues 108–120 of Ii (SEQ ID NO:16).

17. The preparation of claim 1, wherein the peptide comprises residues 101–120 of Ii (SEQ ID NO:63).

18. The preparation of claim 1, wherein the peptide comprises residues 107–125 of Ii (SEQ ID NO:64).

19. The liposome of claim 3, wherein the peptide comprises residues 98–122 of Ii (SEQ ID NO:6).

20. The liposome of claim 3, wherein the peptide comprises residues 98–121 of Ii (SEQ ID NO:7).

21. The liposome of claim 3, wherein the peptide comprises residues 99–122 of Ii (SEQ ID NO:8).

22. The liposome of claim 3, wherein the peptide comprises residues 98–120 of Ii (SEQ ID NO:9).

23. The liposome of claim 3, wherein the peptide comprises residues 99–121 of Ii (SEQ ID NO:10).

24. The liposome of claim 3, wherein the peptide comprises residues 100–121 of Ii (SEQ ID NO:11).

25. The liposome of claim 3, wherein the peptide comprises residues 99–120 of Ii (SEQ ID NO:12).

26. The liposome of claim 3, wherein the peptide comprises residues 100–120 of Ii (SEQ ID NO:13).

27. The liposome of claim 3, wherein the peptide comprises residues 107–121 of Ii (SEQ ID NO:15).

28. The liposome of claim 3, wherein the peptide comprises residues 108–120 of Ii (SEQ ID NO:16).

29. The liposome of claim 3, wherein the peptide comprises residues 101–120 of Ii (SEQ ID NO:63).

30. The liposome of claim 3, wherein the peptide comprises residues 107–125 of Ii (SEQ ID NO:64).

31. The ISCOM of claim 5, wherein the peptide comprises residues 98–122 of Ii (SEQ ID NO:6).

32. The ISCOM of claim 5, wherein the peptide comprises residues 98–121 of Ii (SEQ ID NO:7).

33. The ISCOM of claim 5, wherein the peptide comprises residues 99–122 of Ii (SEQ ID NO:8).

34. The ISCOM of claim 5, wherein the peptide comprises residues 98–120 of Ii (SEQ ID NO:9).

35. The ISCOM of claim 5, wherein the peptide comprises residues 99–121 of Ii (SEQ ID NO:10).

36. The ISCOM of claim 5, wherein the peptide comprises residues 100–121 of Ii (SEQ ID NO:11).

37. The ISCOM of claim 5, wherein the peptide comprises residues 99–120 of Ii (SEQ ID NO:12).

38. The ISCOM of claim 5, wherein the peptide comprises residues 100–120 of Ii (SEQ ID NO:13).

39. The ISCOM of claim 5, wherein the peptide comprises residues 107–121 of Ii (SEQ ID NO:15).

40. The ISCOM of claim 5, wherein the peptide comprises residues 108–120 of Ii (SEQ ID N0:16).

41. The ISCOM of claim 5, wherein the peptide comprises residues 101–120 of Ii (SEQ ID NO:63).

42. The ISCOM of claim 5, wherein the peptide comprises residues 107–125 of Ii (SEQ ID NO:64).

* * * * *

SEQUENCE LISTING (1) GENERAL INFORMATION:

(iii) NUMBER OF SEQUENCES: 274

(2) INFORMATION FOR SEQ ID NO: 1:

(i) SEQUENCE CHARACTERISTICS:
      (A) LENGTH: 18
      (B) TYPE: amino acid
      (C) STRANDEDNESS:
      (D) TOPOLOGY: linear (xi) SEQUENCE DESCRIPTION: SEQ ID NO: 1:

Val Gly Ser Asp Trp Arg Phe Leu Arg Gly Tyr His Gln Tyr Ala Tyr
1               5                   10                  15

Asp Gly (2) INFORMATION FOR SEQ ID NO: 2:

(i) SEQUENCE CHARACTERISTICS:
      (A) LENGTH: 15
      (B) TYPE: amino acid
      (C) STRANDEDNESS:
      (D) TOPOLOGY: linear (xi) SEQUENCE DESCRIPTION: SEQ ID NO: 2:

Val Gly Ser Asp Trp Arg Phe Leu Arg Gly Tyr His Gln Tyr Ala
1               5                   10                  15

(2) INFORMATION FOR SEQ ID NO: 3:

(i) SEQUENCE CHARACTERISTICS:
      (A) LENGTH: 14
      (B) TYPE: amino acid
      (C) STRANDEDNESS:
      (D) TOPOLOGY: linear (xi) SEQUENCE DESCRIPTION: SEQ ID NO: 3:

Val Gly Ser Asp Trp Arg Phe Leu Arg Gly Tyr His Gln Tyr
1               5                   10

(2) INFORMATION FOR SEQ ID NO: 4:

(i) SEQUENCE CHARACTERISTICS:
      (A) LENGTH: 14
      (B) TYPE: amino acid
      (C) STRANDEDNESS:
      (D) TOPOLOGY: linear (xi) SEQUENCE DESCRIPTION: SEQ ID NO: 4:

Gly Ser Asp Trp Arg Phe Leu Arg Gly Tyr His Gln Tyr Ala
 1               5                  10

(2) INFORMATION FOR SEQ ID NO:   5:

(i) SEQUENCE CHARACTERISTICS:
            (A) LENGTH:            13
            (B) TYPE:              amino acid
            (C) STRANDEDNESS:
            (D) TOPOLOGY:          linear (xi) SEQUENCE DESCRIPTION: SEQ ID NO: 5:

Ser Asp Trp Arg Phe Leu Arg Gly Tyr His Gln Tyr Ala
 1               5                  10

(2) INFORMATION FOR SEQ ID NO:   6:

(i) SEQUENCE CHARACTERISTICS:
            (A) LENGTH:            25
            (B) TYPE:              amino acid
            (C) STRANDEDNESS:
            (D) TOPOLOGY:          linear (xi) SEQUENCE DESCRIPTION: SEQ ID NO: 6:

Leu Pro Lys Pro Pro Lys Pro Val Ser Lys Met Arg Met Ala Thr Pro
 1               5                  10                  15

Leu Leu Met Gln Ala Leu Pro Met Gly
                20                  25

(2) INFORMATION FOR SEQ ID NO:   7:

(i) SEQUENCE CHARACTERISTICS:
            (A) LENGTH:            24
            (B) TYPE:              amino acid
            (C) STRANDEDNESS:
            (D) TOPOLOGY:          linear (xi) SEQUENCE DESCRIPTION: SEQ ID NO: 7:

Leu Pro Lys Pro Pro Lys Pro Val Ser Lys Met Arg Met Ala Thr Pro
 1               5                  10                  15

Leu Leu Met Gln Ala Leu Pro Met
                20

(2) INFORMATION FOR SEQ ID NO:   8:

(i) SEQUENCE CHARACTERISTICS:
            (A) LENGTH:            24
            (B) TYPE:              amino acid
            (C) STRANDEDNESS:
            (D) TOPOLOGY:          linear (xi) SEQUENCE DESCRIPTION: SEQ ID NO: 8:

Pro Lys Pro Pro Lys Pro Val Ser Lys Met Arg Met Ala Thr Pro Leu
 1               5                  10                  15

Leu Met Gln Ala Leu Pro Met Gly
                20

(2) INFORMATION FOR SEQ ID NO:   9:

(i) SEQUENCE CHARACTERISTICS:
            (A) LENGTH:            23
            (B) TYPE:              amino acid
            (C) STRANDEDNESS:
            (D) TOPOLOGY:          linear (xi) SEQUENCE DESCRIPTION: SEQ ID NO: 9:

Leu Pro Lys Pro Pro Lys Pro Val Ser Lys Met Arg Met Ala Thr Pro
  1               5                  10                  15

Leu Leu Met Gln Ala Leu Pro
            20

(2) INFORMATION FOR SEQ ID NO:   10:

(i) SEQUENCE CHARACTERISTICS:
        (A) LENGTH:              23
        (B) TYPE:                amino acid
        (C) STRANDEDNESS:
        (D) TOPOLOGY:            linear (xi) SEQUENCE DESCRIPTION: SEQ ID NO: 10:

Pro Lys Pro Pro Lys Pro Val Ser Lys Met Arg Met Ala Thr Pro Leu
  1               5                  10                  15

Leu Met Gln Ala Leu Pro Met
            20

(2) INFORMATION FOR SEQ ID NO:   11:

(i) SEQUENCE CHARACTERISTICS:
        (A) LENGTH:              22
        (B) TYPE:                amino acid
        (C) STRANDEDNESS:
        (D) TOPOLOGY:            linear (xi) SEQUENCE DESCRIPTION: SEQ ID NO: 11:

Lys Pro Pro Lys Pro Val Ser Lys Met Arg Met Ala Thr Pro Leu Leu
  1               5                  10                  15

Met Gln Ala Leu Pro Met
            20

(2) INFORMATION FOR SEQ ID NO:   12:

(i) SEQUENCE CHARACTERISTICS:
        (A) LENGTH:              22
        (B) TYPE:                amino acid
        (C) STRANDEDNESS:
        (D) TOPOLOGY:            linear (xi) SEQUENCE DESCRIPTION: SEQ ID NO: 12:

Pro Lys Pro Pro Lys Pro Val Ser Lys Met Arg Met Ala Thr Pro Leu
  1               5                  10                  15

Leu Met Gln Ala Leu Pro
            20

(2) INFORMATION FOR SEQ ID NO:   13:

(i) SEQUENCE CHARACTERISTICS:
        (A) LENGTH:              21
        (B) TYPE:                amino acid
        (C) STRANDEDNESS:
        (D) TOPOLOGY:            linear (xi) SEQUENCE DESCRIPTION: SEQ ID NO: 13:

Lys Pro Pro Lys Pro Val Ser Lys Met Arg Met Ala Thr Pro Leu Leu
  1               5                  10                  15

Met Gln Ala Leu Pro
            20

(2) INFORMATION FOR SEQ ID NO:   14:

```
        (i) SEQUENCE CHARACTERISTICS:
             (A) LENGTH:           20
             (B) TYPE:             amino acid
             (C) STRANDEDNESS:
             (D) TOPOLOGY:         linear (xi) SEQUENCE DESCRIPTION: SEQ ID NO: 14:

Pro Pro Lys Pro Val Ser Lys Met Arg Met Ala Thr Pro Leu Leu Met
1               5                   10                  15

Gln Ala Leu Pro
            20

(2) INFORMATION FOR SEQ ID NO:    15:

(i) SEQUENCE CHARACTERISTICS:
             (A) LENGTH:           15
             (B) TYPE:             amino acid
             (C) STRANDEDNESS:
             (D) TOPOLOGY:         linear (xi) SEQUENCE DESCRIPTION: SEQ ID NO: 15:

Lys Met Arg Met Ala Thr Pro Leu Leu Met Gln Ala Leu Pro Met
1               5                   10                  15

(2) INFORMATION FOR SEQ ID NO:    16:

(i) SEQUENCE CHARACTERISTICS:
             (A) LENGTH:           14
             (B) TYPE:             amino acid
             (C) STRANDEDNESS:
             (D) TOPOLOGY:         linear (xi) SEQUENCE DESCRIPTION: SEQ ID NO: 16:

Lys Met Arg Met Ala Thr Pro Leu Leu Met Gln Ala Leu Pro
1               5                   10

(2) INFORMATION FOR SEQ ID NO:    17:

(i) SEQUENCE CHARACTERISTICS:
             (A) LENGTH:           18
             (B) TYPE:             amino acid
             (C) STRANDEDNESS:
             (D) TOPOLOGY:         linear (xi) SEQUENCE DESCRIPTION: SEQ ID NO: 17:

Ile Pro Ala Asp Leu Arg Ile Ile Ser Ala Asn Gly Cys Lys Val Asp
1               5                   10                  15

Asn Ser (2) INFORMATION FOR SEQ ID NO:    18:

(i) SEQUENCE CHARACTERISTICS:
             (A) LENGTH:           17
             (B) TYPE:             amino acid
             (C) STRANDEDNESS:
             (D) TOPOLOGY:         linear (xi) SEQUENCE DESCRIPTION: SEQ ID NO: 18:

Arg Val Glu Tyr His Phe Leu Ser Pro Tyr Val Ser Pro Lys Glu Ser
1               5                   10                  15

Pro (2) INFORMATION FOR SEQ ID NO:    19:

(i) SEQUENCE CHARACTERISTICS:
             (A) LENGTH:           19
```

```
            (B) TYPE:              amino acid
            (C) STRANDEDNESS:
            (D) TOPOLOGY:          linear (xi) SEQUENCE DESCRIPTION: SEQ ID NO: 19:

Tyr Lys His Thr Leu Asn Gln Ile Asp Ser Val Lys Val Trp Pro Arg
 1               5                  10                  15

Arg Pro Thr (2) INFORMATION FOR SEQ ID NO:    20:

(i) SEQUENCE CHARACTERISTICS:
            (A) LENGTH:            18
            (B) TYPE:              amino acid
            (C) STRANDEDNESS:
            (D) TOPOLOGY:          linear (xi) SEQUENCE DESCRIPTION: SEQ ID NO: 20:

Tyr Lys His Thr Leu Asn Gln Ile Asp Ser Val Lys Val Trp Pro Arg
 1               5                  10                  15

Arg Pro (2) INFORMATION FOR SEQ ID NO:    21:

(i) SEQUENCE CHARACTERISTICS:
            (A) LENGTH:            19
            (B) TYPE:              amino acid
            (C) STRANDEDNESS:
            (D) TOPOLOGY:          linear (xi) SEQUENCE DESCRIPTION: SEQ ID NO: 21:

Asp Val Gly Glu Tyr Arg Ala Val Thr Glu Leu Gly Arg Pro Asp Ala
 1               5                  10                  15

Glu Tyr Trp (2) INFORMATION FOR SEQ ID NO:    22:

(i) SEQUENCE CHARACTERISTICS:
            (A) LENGTH:            15
            (B) TYPE:              amino acid
            (C) STRANDEDNESS:
            (D) TOPOLOGY:          linear (xi) SEQUENCE DESCRIPTION: SEQ ID NO: 22:

Glu Pro Gly Glu Pro Glu Phe Lys Tyr Ile Gly Asn Met His Gly
 1               5                  10                  15

(2) INFORMATION FOR SEQ ID NO:    23:

(i) SEQUENCE CHARACTERISTICS:
            (A) LENGTH:            17
            (B) TYPE:              amino acid
            (C) STRANDEDNESS:
            (D) TOPOLOGY:          linear (xi) SEQUENCE DESCRIPTION: SEQ ID NO: 23:

Tyr Lys His Thr Leu Asn Gln Ile Asp Ser Val Lys Val Trp Pro Arg
 1               5                  10                  15

Arg (2) INFORMATION FOR SEQ ID NO:    24:

(i) SEQUENCE CHARACTERISTICS:
            (A) LENGTH:            13
            (B) TYPE:              amino acid
```

(C) STRANDEDNESS:
         (D) TOPOLOGY:            linear (xi) SEQUENCE DESCRIPTION: SEQ ID NO: 24:

Pro Lys Tyr Val Lys Gln Asn Thr Leu Lys Leu Ala Thr
 1               5                  10

(2) INFORMATION FOR SEQ ID NO:   25:

(i) SEQUENCE CHARACTERISTICS:
         (A) LENGTH:              15
         (B) TYPE:                amino acid
         (C) STRANDEDNESS:
         (D) TOPOLOGY:            linear (xi) SEQUENCE DESCRIPTION: SEQ ID NO: 25:

Leu Pro Lys Pro Pro Lys Pro Val Ser Lys Met Arg Met Ala Thr
 1               5                  10                  15

(2) INFORMATION FOR SEQ ID NO:   26:

(i) SEQUENCE CHARACTERISTICS:
         (A) LENGTH:              13
         (B) TYPE:                amino acid
         (C) STRANDEDNESS:
         (D) TOPOLOGY:            linear (xi) SEQUENCE DESCRIPTION: SEQ ID NO: 26:

Ser Asp Leu Ser Phe Ser Lys Asp Trp Ser Phe Tyr Leu
 1               5                  10

(2) INFORMATION FOR SEQ ID NO:   27:

(i) SEQUENCE CHARACTERISTICS:
         (A) LENGTH:              18
         (B) TYPE:                amino acid
         (C) STRANDEDNESS:
         (D) TOPOLOGY:            linear (xi) SEQUENCE DESCRIPTION: SEQ ID NO: 27:

Lys Val Phe Gly Arg Cys Glu Leu Ala Ala Ala Met Lys Arg His Gly
 1               5                  10                  15

Leu Asp (2) INFORMATION FOR SEQ ID NO:   28:

(i) SEQUENCE CHARACTERISTICS:
         (A) LENGTH:              18
         (B) TYPE:                amino acid
         (C) STRANDEDNESS:
         (D) TOPOLOGY:            linear (xi) SEQUENCE DESCRIPTION: SEQ ID NO: 28:

Arg Asn Arg Cys Lys Gly Thr Asp Val Gln Ala Trp Ile Arg Gly Cys
 1               5                  10                  15

Arg Leu (2) INFORMATION FOR SEQ ID NO:   29:

(i) SEQUENCE CHARACTERISTICS:
         (A) LENGTH:              16
         (B) TYPE:                amino acid
         (C) STRANDEDNESS:
         (D) TOPOLOGY:            linear (xi) SEQUENCE DESCRIPTION: SEQ ID NO: 29:

His Pro Pro His Ile Glu Ile Gln Met Leu Lys Asn Gly Lys Lys Ile
 1               5                  10                  15

(2) INFORMATION FOR SEQ ID NO:      30:

(i) SEQUENCE CHARACTERISTICS:
        (A) LENGTH:              16
        (B) TYPE:                amino acid
        (C) STRANDEDNESS:
        (D) TOPOLOGY:            linear (xi) SEQUENCE DESCRIPTION: SEQ ID NO: 30:

Asn Glu Leu Gly Arg Phe Lys His Thr Asp Ala Cys Cys Arg Thr His
 1               5                  10                  15

(2) INFORMATION FOR SEQ ID NO:      31:

(i) SEQUENCE CHARACTERISTICS:
        (A) LENGTH:              14
        (B) TYPE:                amino acid
        (C) STRANDEDNESS:
        (D) TOPOLOGY:            linear (xi) SEQUENCE DESCRIPTION: SEQ ID NO: 31:

Ser Lys Pro Lys Val Tyr Gln Trp Phe Asp Leu Arg Lys Tyr
 1               5                  10

(2) INFORMATION FOR SEQ ID NO:      32:

(i) SEQUENCE CHARACTERISTICS:
        (A) LENGTH:              20
        (B) TYPE:                amino acid
        (C) STRANDEDNESS:
        (D) TOPOLOGY:            linear (xi) SEQUENCE DESCRIPTION: SEQ ID NO: 32:

Ala Thr Ser Thr Lys Lys Leu His Lys Glu Pro Ala Thr Leu Ile Lys
 1               5                  10                  15

Ala Ile Asp Gly
            20

(2) INFORMATION FOR SEQ ID NO:      33:

(i) SEQUENCE CHARACTERISTICS:
        (A) LENGTH:              20
        (B) TYPE:                amino acid
        (C) STRANDEDNESS:
        (D) TOPOLOGY:            linear (xi) SEQUENCE DESCRIPTION: SEQ ID NO: 33:

Pro Ala Thr Leu Ile Lys Ala Ile Asp Gly Asp Thr Val Lys Leu Met
 1               5                  10                  15

Tyr Lys Gly Gln
            20

(2) INFORMATION FOR SEQ ID NO:      34:

(i) SEQUENCE CHARACTERISTICS:
        (A) LENGTH:              20
        (B) TYPE:                amino acid
        (C) STRANDEDNESS:
        (D) TOPOLOGY:            linear (xi) SEQUENCE DESCRIPTION: SEQ ID NO: 34:

Asp Arg Val Lys Leu Met Tyr Lys Gly Gln Pro Met Thr Phe Arg Leu
 1               5                  10                  15

```
Leu Leu Val Asp
            20

(2) INFORMATION FOR SEQ ID NO:    35:

(i) SEQUENCE CHARACTERISTICS:
        (A) LENGTH:           20
        (B) TYPE:             amino acid
        (C) STRANDEDNESS:
        (D) TOPOLOGY:         linear (xi) SEQUENCE DESCRIPTION: SEQ ID NO: 35:

Val Ala Tyr Val Tyr Lys Pro Asn Asn Thr His Glu Gln His Leu Arg
  1               5                  10                  15

Lys Ser Glu Ala
            20

(2) INFORMATION FOR SEQ ID NO:    36:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 36:

Gln Lys Gln Glu Pro Ile Asp Lys Glu Leu Tyr Pro Leu Thr Ser Leu
  1               5                  10                  15

(2) INFORMATION FOR SEQ ID NO:    37:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 37:

Gly Ala Arg Ala Ser Val Leu Ser Gly Gly Glu Leu Asp Lys Trp Glu
  1               5                  10                  15

(2) INFORMATION FOR SEQ ID NO:    38:

(i) SEQUENCE CHARACTERISTICS:
        (A) LENGTH:           20
        (B) TYPE:             amino acid
        (C) STRANDEDNESS:
        (D) TOPOLOGY:         linear (xi) SEQUENCE DESCRIPTION: SEQ ID NO: 38:

Arg Thr Leu Tyr Gln Asn Val Gly Thr Tyr Val Ser Val Gly Thr Ser
  1               5                  10                  15

Thr Leu Asn Lys
            20

(2) INFORMATION FOR SEQ ID NO:    39:

(i) SEQUENCE CHARACTERISTICS:
        (A) LENGTH:           15
        (B) TYPE:             amino acid
        (C) STRANDEDNESS:
        (D) TOPOLOGY:         linear (xi) SEQUENCE DESCRIPTION: SEQ ID NO: 39:

Leu Lys Lys Leu Val Phe Gly Tyr Arg Lys Pro Leu Asp Asn Ile
  1               5                  10                  15
```

(2) INFORMATION FOR SEQ ID NO: 40:

(i) SEQUENCE CHARACTERISTICS:
        (A) LENGTH: 13
        (B) TYPE: amino acid
        (C) STRANDEDNESS:
        (D) TOPOLOGY: linear (xi) SEQUENCE DESCRIPTION: SEQ ID NO: 40:

```
Lys His Ile Glu Gln Tyr Leu Lys Lys Ile Lys Asn Ser
 1               5                  10
```

(2) INFORMATION FOR SEQ ID NO: 41:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQ ID NO: 41:

```
Asp Val Phe Lys Glu Leu Lys Val His His Ala Asn Glu Asn Ile Phe
 1               5                  10                  15
```

(2) INFORMATION FOR SEQ ID NO: 42:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQ ID NO: 42:

```
Gly Asp Thr Arg Pro Arg Phe Leu Trp Gln Leu Lys Phe Glu Cys His
 1               5                  10                  15
Phe Phe Asn Gly
         20
```

(2) INFORMATION FOR SEQ ID NO: 43:

(i) SEQUENCE CHARACTERISTICS:
        (A) LENGTH: 22
        (B) TYPE: amino acid
        (C) STRANDEDNESS:
        (D) TOPOLOGY: linear (xi) SEQUENCE DESCRIPTION: SEQ ID NO: 43:

```
Thr Glu Arg Val Arg Leu Leu Glu Arg Cys Ile Tyr Asn Gln Glu Glu
 1               5                  10                  15
Ser Val Arg Phe Asp Ser
         20
```

(2) INFORMATION FOR SEQ ID NO: 44:

(i) SEQUENCE CHARACTERISTICS:
        (A) LENGTH: 25
        (B) TYPE: amino acid
        (C) STRANDEDNESS:
        (D) TOPOLOGY: linear (xi) SEQUENCE DESCRIPTION: SEQ ID NO: 44:

```
Asp Leu Leu Glu Gln Arg Arg Ala Ala Val Asp Thr Tyr Cys Arg His
 1               5                  10                  15
Asn Tyr Gly Val Gly Glu Ser Phe Thr
         20                  25
```

(2) INFORMATION FOR SEQ ID NO:   45:

(i) SEQUENCE CHARACTERISTICS:
        (A) LENGTH:          17
        (B) TYPE:            amino acid
        (C) STRANDEDNESS:
        (D) TOPOLOGY:        linear (xi) SEQUENCE DESCRIPTION: SEQ ID NO: 45:

Lys Ala Glu Arg Ala Asp Leu Ile Ala Tyr Leu Lys Gln Ala Thr Ala
 1               5                  10                  15
Lys (2) INFORMATION FOR SEQ ID NO:   46:

(i) SEQUENCE CHARACTERISTICS:
        (A) LENGTH:          24
        (B) TYPE:            amino acid
        (C) STRANDEDNESS:
        (D) TOPOLOGY:        linear (xi) SEQUENCE DESCRIPTION: SEQ ID NO: 46:

Gly Arg Thr Gln Asp Glu Asn Pro Val Val His Phe Phe Lys Asn Ile
 1               5                  10                  15
Val Thr Pro Arg Thr Pro Pro Pro
                20

(2) INFORMATION FOR SEQ ID NO:   47:

(i) SEQUENCE CHARACTERISTICS:
        (A) LENGTH:          13
        (B) TYPE:            amino acid
        (C) STRANDEDNESS:
        (D) TOPOLOGY:        linear (xi) SEQUENCE DESCRIPTION: SEQ ID NO: 47:

Pro Leu Lys Ala Glu Ile Ala Gln Arg Leu Glu Asp Val
 1               5                  10

(2) INFORMATION FOR SEQ ID NO:   48:

(i) SEQUENCE CHARACTERISTICS:
        (A) LENGTH:          16
        (B) TYPE:            amino acid
        (C) STRANDEDNESS:
        (D) TOPOLOGY:        linear (xi) SEQUENCE DESCRIPTION: SEQ ID NO: 48:

Arg Gln Ile Leu Gly Gln Leu Gln Pro Ser Leu Gln Thr Gly Ser Glu
 1               5                  10                  15

(2) INFORMATION FOR SEQ ID NO:   49:

(i) SEQUENCE CHARACTERISTICS:
        (A) LENGTH:          16
        (B) TYPE:            amino acid
        (C) STRANDEDNESS:
        (D) TOPOLOGY:        linear (xi) SEQUENCE DESCRIPTION: SEQ ID NO: 49:

Ile Gln Val Tyr Ser Arg His Pro Pro Glu Asn Gly Lys Pro Asn Ile
 1               5                  10                  15

(2) INFORMATION FOR SEQ ID NO:   50:

(i) SEQUENCE CHARACTERISTICS:

(A) LENGTH:             16
        (B) TYPE:               amino acid
        (C) STRANDEDNESS:
        (D) TOPOLOGY:           linear (xi) SEQUENCE DESCRIPTION: SEQ ID NO: 50:

Ile Asn Thr Lys Cys Tyr Lys Leu Glu His Pro Val Thr Gly Cys Gly
 1               5                  10                  15

(2) INFORMATION FOR SEQ ID NO:   51:

(i) SEQUENCE CHARACTERISTICS:
        (A) LENGTH:             14
        (B) TYPE:               amino acid
        (C) STRANDEDNESS:
        (D) TOPOLOGY:           linear (xi) SEQUENCE DESCRIPTION: SEQ ID NO: 51:

Tyr Lys Leu Asn Phe Tyr Phe Asp Leu Leu Arg Ala Lys Leu
 1               5                  10

(2) INFORMATION FOR SEQ ID NO:   52:

(i) SEQUENCE CHARACTERISTICS:
        (A) LENGTH:             13
        (B) TYPE:               amino acid
        (C) STRANDEDNESS:
        (D) TOPOLOGY:           linear (xi) SEQUENCE DESCRIPTION: SEQ ID NO: 52:

Ile Asp Thr Leu Lys Lys Asn Glu Asn Ile Lys Glu Leu
 1               5                  10

(2) INFORMATION FOR SEQ ID NO:   53:

(i) SEQUENCE CHARACTERISTICS:
        (A) LENGTH:             20
        (B) TYPE:               amino acid
        (C) STRANDEDNESS:
        (D) TOPOLOGY:           linear (xi) SEQUENCE DESCRIPTION: SEQ ID NO: 53:

Asp Val Gly Glu Tyr Arg Ala Val Thr Glu Leu Gly Arg Pro Asp Ala
 1               5                  10                  15

Glu Tyr Trp Asn
            20

(2) INFORMATION FOR SEQ ID NO:   54:

(i) SEQUENCE CHARACTERISTICS:
        (A) LENGTH:             16
        (B) TYPE:               amino acid
        (C) STRANDEDNESS:
        (D) TOPOLOGY:           linear (xi) SEQUENCE DESCRIPTION: SEQ ID NO: 54:

Glu Arg Phe Ala Val Asn Pro Gly Leu Leu Glu Thr Ser Glu Gly Cys
 1               5                  10                  15

(2) INFORMATION FOR SEQ ID NO:   55:

(i) SEQUENCE CHARACTERISTICS:
        (A) LENGTH:             23
        (B) TYPE:               amino acid
        (C) STRANDEDNESS:
        (D) TOPOLOGY:           linear (xi) SEQUENCE DESCRIPTION: SEQ ID NO: 55:

```
Asp Asn Tyr Arg Gly Tyr Ser Leu Gly Asn Trp Val Cys Ala Ala Lys
  1               5                  10                  15

Phe Glu Ser Asn Phe Thr Gln
             20
```

(2) INFORMATION FOR SEQ ID NO: 56:

(i) SEQUENCE CHARACTERISTICS:
        (A) LENGTH:         20
        (B) TYPE:           amino acid
        (C) STRANDEDNESS:
        (D) TOPOLOGY:      linear (xi) SEQUENCE DESCRIPTION: SEQ ID NO: 56:

```
Glu Ala Leu Val Arg Gln Gly Leu Ala Lys Val Ala Tyr Val Tyr Lys
  1               5                  10                  15

Pro Asn Asn Thr
             20
```

(2) INFORMATION FOR SEQ ID NO: 57:

(i) SEQUENCE CHARACTERISTICS:
        (A) LENGTH:         16
        (B) TYPE:           amino acid
        (C) STRANDEDNESS:
        (D) TOPOLOGY:      linear (xi) SEQUENCE DESCRIPTION: SEQ ID NO: 57:

```
Pro Ile Val Gln Asn Leu Gln Gly Gln Met Val His Gln Ala Ile Ser
  1               5                  10                  15
```

(2) INFORMATION FOR SEQ ID NO: 58:

(i) SEQUENCE CHARACTERISTICS:
        (A) LENGTH:         16
        (B) TYPE:           amino acid
        (C) STRANDEDNESS:
        (D) TOPOLOGY:      linear (xi) SEQUENCE DESCRIPTION: SEQ ID NO: 58:

```
Ser Ala Leu Ser Glu Gly Ala Thr Pro Gln Asp Leu Asn Thr Met Leu
  1               5                  10                  15
```

(2) INFORMATION FOR SEQ ID NO: 59:

(i) SEQUENCE CHARACTERISTICS:
        (A) LENGTH:         16
        (B) TYPE:           amino acid
        (C) STRANDEDNESS:
        (D) TOPOLOGY:      linear (xi) SEQUENCE DESCRIPTION: SEQ ID NO: 59:

```
Ser Phe Tyr Ile Leu Ala His Thr Glu Phe Thr Pro Thr Glu Thr Asp
  1               5                  10                  15
```

(2) INFORMATION FOR SEQ ID NO: 60:

(i) SEQUENCE CHARACTERISTICS:
        (A) LENGTH:         16
        (B) TYPE:           amino acid
        (C) STRANDEDNESS:
        (D) TOPOLOGY:      linear (xi) SEQUENCE DESCRIPTION: SEQ ID NO: 60:

```
Lys Met Tyr Phe Asn Leu Ile Asn Thr Lys Cys Tyr Lys Leu Glu His
  1               5                  10                  15
```

(2) INFORMATION FOR SEQ ID NO:    61:

(i) SEQUENCE CHARACTERISTICS:
        (A) LENGTH:              18
        (B) TYPE:                amino acid
        (C) STRANDEDNESS:
        (D) TOPOLOGY:            linear (xi) SEQUENCE DESCRIPTION: SEQ ID NO: 61:

```
Val Gly Ser Asp Trp Arg Phe Leu Arg Gly Tyr His Gln Tyr Ala Tyr
 1               5                  10                  15
Ala Asp
```

(2) INFORMATION FOR SEQ ID NO:    62:

(i) SEQUENCE CHARACTERISTICS:
        (A) LENGTH:              17
        (B) TYPE:                amino acid
        (C) STRANDEDNESS:
        (D) TOPOLOGY:            linear (xi) SEQUENCE DESCRIPTION: SEQ ID NO: 62:

```
Gly Ser Asp Trp Arg Phe Leu Arg Gly Tyr His Gln Tyr Ala Tyr Asp
 1               5                  10                  15
Gly
```

(2) INFORMATION FOR SEQ ID NO:    63:

(i) SEQUENCE CHARACTERISTICS:
        (A) LENGTH:              20
        (B) TYPE:                amino acid
        (C) STRANDEDNESS:
        (D) TOPOLOGY:            linear (xi) SEQUENCE DESCRIPTION: SEQ ID NO: 63:

```
Pro Pro Lys Pro Val Ser Lys Met Arg Met Ala Thr Pro Leu Leu Met
 1               5                  10                  15
Gln Ala Leu Pro
                20
```

(2) INFORMATION FOR SEQ ID NO:    64:

(i) SEQUENCE CHARACTERISTICS:
        (A) LENGTH:              19
        (B) TYPE:                amino acid
        (C) STRANDEDNESS:
        (D) TOPOLOGY:            linear (xi) SEQUENCE DESCRIPTION: SEQ ID NO: 64:

```
Lys Met Arg Met Ala Thr Pro Leu Leu Met Gln Ala Leu Pro Met Gly
 1               5                  10                  15
Ala Leu Pro
```

(2) INFORMATION FOR SEQ ID NO:    65:

(i) SEQUENCE CHARACTERISTICS:
        (A) LENGTH:              23
        (B) TYPE:                amino acid
        (C) STRANDEDNESS:
        (D) TOPOLOGY:            linear (xi) SEQUENCE DESCRIPTION: SEQ ID NO: 65:

```
Glu His His Ile Phe Leu Gly Ala Thr Asn Tyr Ile Tyr Val Leu Asn
 1               5                  10                  15
```

Glu Glu Asp Leu Gln Lys Val
            20

(2) INFORMATION FOR SEQ ID NO:    66:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 66:

Gln Glu Leu Lys Asn Lys Tyr Tyr Gln Val Pro Arg Lys Gly Ile Gln
1               5                   10                  15
Ala (2) INFORMATION FOR SEQ ID NO:    67:

(i) SEQUENCE CHARACTERISTICS:
        (A) LENGTH:            20
        (B) TYPE:              amino acid
        (C) STRANDEDNESS:
        (D) TOPOLOGY:          linear (xi) SEQUENCE DESCRIPTION: SEQ ID NO: 67:

Ile Gln Asn Leu Ile Lys Glu Glu Ala Phe Leu Gly Ile Thr Asp Glu
1               5                   10                  15
Lys Thr Glu Gly
            20

(2) INFORMATION FOR SEQ ID NO:    68:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 68:

Thr Ala Phe Gln Tyr Ile Ile Asp Asn Lys Gly Ile Asp Ser Asp Ala
1               5                   10                  15
Ser (2) INFORMATION FOR SEQ ID NO:    69:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 69:

Glu Pro Phe Leu Tyr Ile Leu Gly Lys Ser Arg Val Leu Glu Ala Gln
1               5                   10                  15

(2) INFORMATION FOR SEQ ID NO:    70:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 70:

Thr Leu Pro Pro Phe Gln Pro Gln Ile Thr Asp Asp Tyr Gly Leu Asp

-continued

```
    1               5              10              15
```

(2) INFORMATION FOR SEQ ID NO:   71:

(i) SEQUENCE CHARACTERISTICS:
        (A) LENGTH:              16
        (B) TYPE:                amino acid
        (C) STRANDEDNESS:
        (D) TOPOLOGY:            linear (xi) SEQUENCE DESCRIPTION: SEQ ID NO: 71:

```
Val Arg Trp Phe Arg Asn Gly Gln Glu Glu Lys Thr Gly Val Val Ser
 1               5                  10                  15
```

(2) INFORMATION FOR SEQ ID NO:   72:

(i) SEQUENCE CHARACTERISTICS:
        (A) LENGTH:              18
        (B) TYPE:                amino acid
        (C) STRANDEDNESS:
        (D) TOPOLOGY:            linear (xi) SEQUENCE DESCRIPTION: SEQ ID NO: 72:

```
Arg Val Gln Pro Lys Val Thr Val Tyr Pro Ser Lys Thr Gln Pro Leu
 1               5                  10                  15
Gln His
```

(2) INFORMATION FOR SEQ ID NO:   73:

(i) SEQUENCE CHARACTERISTICS:
        (A) LENGTH:              15
        (B) TYPE:                amino acid
        (C) STRANDEDNESS:
        (D) TOPOLOGY:            linear (xi) SEQUENCE DESCRIPTION: SEQ ID NO: 73:

```
Arg Val Gln Pro Lys Val Thr Val Tyr Pro Ser Lys Thr Gln Pro
 1               5                  10                  15
```

(2) INFORMATION FOR SEQ ID NO:   74:

(i) SEQUENCE CHARACTERISTICS:
        (A) LENGTH:              19
        (B) TYPE:                amino acid
        (C) STRANDEDNESS:
        (D) TOPOLOGY:            linear (xi) SEQUENCE DESCRIPTION: SEQ ID NO: 74:

```
Asn Phe Leu Lys Ser Asp Gly Arg Ile Lys Tyr Thr Leu Asn Lys Asn
 1               5                  10                  15
Ser Leu Lys
```

(2) INFORMATION FOR SEQ ID NO:   75:

(i) SEQUENCE CHARACTERISTICS:
        (A) LENGTH:              19
        (B) TYPE:                amino acid
        (C) STRANDEDNESS:
        (D) TOPOLOGY:            linear (xi) SEQUENCE DESCRIPTION: SEQ ID NO: 75:

```
Ile Pro Asp Asn Leu Phe Leu Lys Ser Asp Gly Arg Ile Lys Tyr Thr
 1               5                  10                  15
Leu Asn Lys
```

(2) INFORMATION FOR SEQ ID NO: 76:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQ ID NO: 76:

```
Asn Leu Phe Leu Lys Ser Asp Gly Arg Ile Lys Tyr Thr Leu Asn Lys
 1               5                  10                  15
```

(2) INFORMATION FOR SEQ ID NO: 77:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 77:

```
Asn Leu Phe Leu Lys Ser Asp Gly Arg Ile Lys Tyr Thr Leu Asn
 1               5                  10                  15
```

(2) INFORMATION FOR SEQ ID NO: 78:

(i) SEQUENCE CHARACTERISTICS:
        (A) LENGTH: 17
        (B) TYPE: amino acid
        (C) STRANDEDNESS:
        (D) TOPOLOGY: linear (xi) SEQUENCE DESCRIPTION: SEQ ID NO: 78:

```
Tyr Ala Asn Ile Leu Leu Asp Arg Arg Val Pro Gln Thr Asp Met Thr
 1               5                  10                  15
Phe
```

(2) INFORMATION FOR SEQ ID NO: 79:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 79:

```
Gly Asp Thr Arg Pro Arg Phe Leu Glu Tyr Ser Thr Ser Glu Cys His
 1               5                  10                  15
Phe Phe
```

(2) INFORMATION FOR SEQ ID NO: 80:

(i) SEQUENCE CHARACTERISTICS:
        (A) LENGTH: 21
        (B) TYPE: amino acid
        (C) STRANDEDNESS:
        (D) TOPOLOGY: linear (xi) SEQUENCE DESCRIPTION: SEQ ID NO: 80:

```
Lys His Lys Val Tyr Ala Cys Glu Val Thr His Gln Gly Leu Ser Ser
 1               5                  10                  15
Pro Val Thr Lys Ser
            20
```

(2) INFORMATION FOR SEQ ID NO: 81:

```
    (i) SEQUENCE CHARACTERISTICS:
        (A) LENGTH:            20
        (B) TYPE:              amino acid
        (C) STRANDEDNESS:
        (D) TOPOLOGY:          linear (xi) SEQUENCE DESCRIPTION: SEQ ID NO: 81:

Lys His Lys Val Tyr Ala Cys Glu Val Thr His Gln Gly Leu Ser Ser
1               5                   10                  15

Pro Val Thr Lys
            20

(2) INFORMATION FOR SEQ ID NO:    82:

(i) SEQUENCE CHARACTERISTICS:
        (A) LENGTH:            18
        (B) TYPE:              amino acid
        (C) STRANDEDNESS:
        (D) TOPOLOGY:          linear (xi) SEQUENCE DESCRIPTION: SEQ ID NO: 82:

His Lys Val Tyr Ala Cys Glu Val Thr His Gln Gly Leu Ser Ser Pro
1               5                   10                  15

Val Thr (2) INFORMATION FOR SEQ ID NO:    83:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 83:

Lys His Lys Val Tyr Ala Cys Glu Val Thr His Gln Gly Leu Ser Ser
1               5                   10                  15

Pro (2) INFORMATION FOR SEQ ID NO:    84:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 84:

Glu Lys His Lys Val Tyr Ala Cys Glu Val Thr His Gln Gly Leu Ser
1               5                   10                  15

Ser (2) INFORMATION FOR SEQ ID NO:    85:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 85:

Lys His Lys Val Tyr Ala Cys Glu Val Thr His Gln Gly Leu Ser Ser
1               5                   10                  15

(2) INFORMATION FOR SEQ ID NO:    86:
```

(i) SEQUENCE CHARACTERISTICS:
        (A) LENGTH:         16
        (B) TYPE:           amino acid
        (C) STRANDEDNESS:
        (D) TOPOLOGY:       linear (xi) SEQUENCE DESCRIPTION: SEQ ID NO: 86:

His Lys Val Tyr Ala Cys Glu Val Thr His Gln Gly Leu Ser Ser Pro
 1               5                  10                  15

(2) INFORMATION FOR SEQ ID NO:    87:

(i) SEQUENCE CHARACTERISTICS:
        (A) LENGTH:         16
        (B) TYPE:           amino acid
        (C) STRANDEDNESS:
        (D) TOPOLOGY:       linear (xi) SEQUENCE DESCRIPTION: SEQ ID NO: 87:

Glu Lys His Lys Val Tyr Ala Cys Glu Val Thr His Gln Gly Leu Ser
 1               5                  10                  15

(2) INFORMATION FOR SEQ ID NO:    88:

(i) SEQUENCE CHARACTERISTICS:
        (A) LENGTH:         15
        (B) TYPE:           amino acid
        (C) STRANDEDNESS:
        (D) TOPOLOGY:       linear (xi) SEQUENCE DESCRIPTION: SEQ ID NO: 88:

Lys His Lys Val Tyr Ala Cys Glu Val Thr His Gln Gly Leu Ser
 1               5                  10                  15

(2) INFORMATION FOR SEQ ID NO:    89:

(i) SEQUENCE CHARACTERISTICS:
        (A) LENGTH:         15
        (B) TYPE:           amino acid
        (C) STRANDEDNESS:
        (D) TOPOLOGY:       linear (xi) SEQUENCE DESCRIPTION: SEQ ID NO: 89:

His Lys Val Tyr Ala Cys Glu Val Thr His Gln Gly Leu Ser Ser
 1               5                  10                  15

(2) INFORMATION FOR SEQ ID NO:    90:

(i) SEQUENCE CHARACTERISTICS:
        (A) LENGTH:         14
        (B) TYPE:           amino acid
        (C) STRANDEDNESS:
        (D) TOPOLOGY:       linear (xi) SEQUENCE DESCRIPTION: SEQ ID NO: 90:

Glu Lys His Lys Val Tyr Ala Cys Glu Val Thr His Gln Gly
 1               5                  10

(2) INFORMATION FOR SEQ ID NO:    91:

(i) SEQUENCE CHARACTERISTICS:
        (A) LENGTH:         17
        (B) TYPE:           amino acid
        (C) STRANDEDNESS:
        (D) TOPOLOGY:       linear (xi) SEQUENCE DESCRIPTION: SEQ ID NO: 91:

Ala Pro Ser Pro Leu Pro Glu Thr Thr Glu Asn Val Val Cys Ala Leu

```
                   1               5              10              15
Gly (2) INFORMATION FOR SEQ ID NO:    92:

(i) SEQUENCE CHARACTERISTICS:
         (A) LENGTH:              21
         (B) TYPE:                amino acid
         (C) STRANDEDNESS:
         (D) TOPOLOGY:            linear (xi) SEQUENCE DESCRIPTION: SEQ ID NO: 92:

Val Asp Asp Thr Gln Phe Val Arg Phe Asp Ser Asp Ala Ala Ser Gln
 1               5                  10                  15

Arg Met Glu Pro Arg
            20

(2) INFORMATION FOR SEQ ID NO:    93:

(i) SEQUENCE CHARACTERISTICS:
         (A) LENGTH:              20
         (B) TYPE:                amino acid
         (C) STRANDEDNESS:
         (D) TOPOLOGY:            linear (xi) SEQUENCE DESCRIPTION: SEQ ID NO: 93:

Val Asp Asp Thr Gln Phe Val Arg Phe Asp Ser Asp Ala Ala Ser Gln
 1               5                  10                  15

Arg Met Glu Pro
            20

(2) INFORMATION FOR SEQ ID NO:    94:

(i) SEQUENCE CHARACTERISTICS:
         (A) LENGTH:              19
         (B) TYPE:                amino acid
         (C) STRANDEDNESS:
         (D) TOPOLOGY:            linear (xi) SEQUENCE DESCRIPTION: SEQ ID NO: 94:

Val Asp Asp Thr Gln Phe Val Arg Phe Asp Ser Asp Ala Ala Ser Gln
 1               5                  10                  15

Arg Met Glu (2) INFORMATION FOR SEQ ID NO:    95:

(i) SEQUENCE CHARACTERISTICS:
         (A) LENGTH:              19
         (B) TYPE:                amino acid
         (C) STRANDEDNESS:
         (D) TOPOLOGY:            linear (xi) SEQUENCE DESCRIPTION: SEQ ID NO: 95:

Asp Thr Gln Phe Val Arg Phe Asp Ser Asp Ala Ala Ser Gln Arg Met
 1               5                  10                  15

Glu Pro Arg (2) INFORMATION FOR SEQ ID NO:    96:

(i) SEQUENCE CHARACTERISTICS:
         (A) LENGTH:              19
         (B) TYPE:                amino acid
         (C) STRANDEDNESS:
         (D) TOPOLOGY:            linear
```

(xi) SEQUENCE DESCRIPTION: SEQ ID NO: 96:

Thr Gln Phe Val Arg Phe Asp Ser Asp Ala Ala Ser Gln Arg Met Glu
  1               5                  10                  15
Pro Arg Ala (2) INFORMATION FOR SEQ ID NO:    97:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 97:

Val Asp Asp Thr Gln Phe Val Arg Phe Asp Ser Asp Ala Ala Ser Gln
  1               5                  10                  15
Arg (2) INFORMATION FOR SEQ ID NO:    98:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 98:

Thr Gln Phe Val Arg Phe Asp Ser Asp Ala Ala Ser Gln Arg Met Glu
  1               5                  10                  15
Pro (2) INFORMATION FOR SEQ ID NO:    99:

(i) SEQUENCE CHARACTERISTICS:
        (A) LENGTH:           15
        (B) TYPE:             amino acid
        (C) STRANDEDNESS:
        (D) TOPOLOGY:         linear (xi) SEQUENCE DESCRIPTION: SEQ ID NO: 99:

Thr Gln Phe Val Arg Phe Asp Ser Asp Ala Ala Ser Gln Arg Met
  1               5                  10                  15

(2) INFORMATION FOR SEQ ID NO:    100:

(i) SEQUENCE CHARACTERISTICS:
        (A) LENGTH:           12
        (B) TYPE:             amino acid
        (C) STRANDEDNESS:
        (D) TOPOLOGY:         linear (xi) SEQUENCE DESCRIPTION: SEQ ID NO: 100:

Thr Gln Phe Val Arg Phe Asp Ser Asp Ala Ala Ser
  1               5                  10

(2) INFORMATION FOR SEQ ID NO:    101:

(i) SEQUENCE CHARACTERISTICS:
        (A) LENGTH:           23
        (B) TYPE:             amino acid
        (C) STRANDEDNESS:
        (D) TOPOLOGY:         linear (xi) SEQUENCE DESCRIPTION: SEQ ID NO: 101:

Val Asp Asp Thr Gln Phe Val Arg Phe Asp Ser Asp Ala Ala Ser Pro

```
              1               5              10              15

Arg Gly Glu Pro Arg Ala Pro
                20

(2) INFORMATION FOR SEQ ID NO:    102:

(i) SEQUENCE CHARACTERISTICS:
          (A) LENGTH:           22
          (B) TYPE:             amino acid
          (C) STRANDEDNESS:
          (D) TOPOLOGY:         linear (xi) SEQUENCE DESCRIPTION: SEQ ID NO: 102:

Thr Gln Phe Val Arg Phe Asp Ser Asp Ala Ala Ser Pro Arg Gly Glu
 1               5                  10                  15
Pro Arg Ala Pro Trp Val
                20

(2) INFORMATION FOR SEQ ID NO:    103:

(i) SEQUENCE CHARACTERISTICS:
          (A) LENGTH:           21
          (B) TYPE:             amino acid
          (C) STRANDEDNESS:
          (D) TOPOLOGY:         linear (xi) SEQUENCE DESCRIPTION: SEQ ID NO: 103:

Val Asp Asp Thr Gln Phe Val Arg Phe Asp Ser Asp Ala Ala Ser Pro
 1               5                  10                  15
Arg Gly Glu Pro Arg
                20

(2) INFORMATION FOR SEQ ID NO:    104:

(i) SEQUENCE CHARACTERISTICS:
          (A) LENGTH:           20
          (B) TYPE:             amino acid
          (C) STRANDEDNESS:
          (D) TOPOLOGY:         linear (xi) SEQUENCE DESCRIPTION: SEQ ID NO: 104:

Val Asp Asp Thr Gln Phe Val Arg Phe Asp Ser Asp Ala Ala Ser Pro
 1               5                  10                  15
Arg Gly Glu Pro
                20

(2) INFORMATION FOR SEQ ID NO:    105:

(i) SEQUENCE CHARACTERISTICS:
          (A) LENGTH:           19
          (B) TYPE:             amino acid
          (C) STRANDEDNESS:
          (D) TOPOLOGY:         linear (xi) SEQUENCE DESCRIPTION: SEQ ID NO: 105:

Val Asp Asp Thr Gln Phe Val Arg Phe Asp Ser Asp Ala Ala Ser Pro
 1               5                  10                  15
Arg Gly Glu (2) INFORMATION FOR SEQ ID NO:    106:

(i) SEQUENCE CHARACTERISTICS:
          (A) LENGTH:           18
          (B) TYPE:             amino acid
          (C) STRANDEDNESS:
```

(D) TOPOLOGY:          linear (xi) SEQUENCE DESCRIPTION: SEQ ID NO: 106:

Val Asp Asp Thr Gln Phe Val Arg Phe Asp Ser Asp Ala Ala Ser Pro
 1               5                  10                  15

Arg Gly (2) INFORMATION FOR SEQ ID NO:   107:

(i) SEQUENCE CHARACTERISTICS:
        (A) LENGTH:            18
        (B) TYPE:              amino acid
        (C) STRANDEDNESS:
        (D) TOPOLOGY:          linear (xi) SEQUENCE DESCRIPTION: SEQ ID NO: 107:

Thr Gln Phe Val Arg Phe Asp Ser Asp Ala Ala Ser Pro Arg Gly Glu
 1               5                  10                  15

Pro Arg (2) INFORMATION FOR SEQ ID NO:   108:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 108:

Val Asp Asp Thr Gln Phe Val Arg Phe Asp Ser Asp Ala Ala Ser Pro
 1               5                  10                  15

Arg (2) INFORMATION FOR SEQ ID NO:   109:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 109:

Asp Thr Gln Phe Val Arg Phe Asp Ser Asp Ala Ala Ser Pro Arg Gly
 1               5                  10                  15

Glu (2) INFORMATION FOR SEQ ID NO:   110:

(i) SEQUENCE CHARACTERISTICS:
        (A) LENGTH:            14
        (B) TYPE:              amino acid
        (C) STRANDEDNESS:
        (D) TOPOLOGY:          linear (xi) SEQUENCE DESCRIPTION: SEQ ID NO: 110:

Thr Gln Phe Val Arg Phe Asp Ser Asp Ala Ala Ser Pro Arg
 1               5                  10

(2) INFORMATION FOR SEQ ID NO:   111:

(i) SEQUENCE CHARACTERISTICS:
        (A) LENGTH:            12
        (B) TYPE:              amino acid
        (C) STRANDEDNESS:
        (D) TOPOLOGY:          linear (xi) SEQUENCE DESCRIPTION: SEQ ID NO: 111:

Thr Gln Phe Val Arg Phe Asp Ser Asp Ala Ala Ser
1               5                   10

(2) INFORMATION FOR SEQ ID NO:    112:

(i) SEQUENCE CHARACTERISTICS:
        (A) LENGTH:              21
        (B) TYPE:                amino acid
        (C) STRANDEDNESS:
        (D) TOPOLOGY:            linear (xi) SEQUENCE DESCRIPTION: SEQ ID NO: 112:

Leu Arg Ser Trp Thr Ala Ala Asp Thr Ala Ala Gln Ile Thr Gln Arg
1               5                   10                  15

Lys Trp Glu Ala Ala
            20

(2) INFORMATION FOR SEQ ID NO:    113:

(i) SEQUENCE CHARACTERISTICS:
        (A) LENGTH:              17
        (B) TYPE:                amino acid
        (C) STRANDEDNESS:
        (D) TOPOLOGY:            linear (xi) SEQUENCE DESCRIPTION: SEQ ID NO: 113:

Asp Leu Arg Ser Trp Thr Ala Ala Asp Thr Ala Ala Gln Ile Thr Gln
1               5                   10                  15

Arg (2) INFORMATION FOR SEQ ID NO:    114:

(i) SEQUENCE CHARACTERISTICS:
        (A) LENGTH:              16
        (B) TYPE:                amino acid
        (C) STRANDEDNESS:
        (D) TOPOLOGY:            linear (xi) SEQUENCE DESCRIPTION: SEQ ID NO: 114:

Asp Leu Arg Ser Trp Thr Ala Ala Asp Thr Ala Ala Gln Ile Thr Gln
1               5                   10                  15

(2) INFORMATION FOR SEQ ID NO:    115:

(i) SEQUENCE CHARACTERISTICS:
        (A) LENGTH:              15
        (B) TYPE:                amino acid
        (C) STRANDEDNESS:
        (D) TOPOLOGY:            linear (xi) SEQUENCE DESCRIPTION: SEQ ID NO: 115:

Asp Leu Arg Ser Trp Thr Ala Ala Asp Thr Ala Ala Gln Ile Thr
1               5                   10                  15

(2) INFORMATION FOR SEQ ID NO:    116:

(i) SEQUENCE CHARACTERISTICS:
        (A) LENGTH:              17
        (B) TYPE:                amino acid
        (C) STRANDEDNESS:
        (D) TOPOLOGY:            linear (xi) SEQUENCE DESCRIPTION: SEQ ID NO: 116:

Asp Leu Ser Ser Trp Thr Ala Ala Asp Thr Ala Ala Gln Ile Thr Gln

```
               1               5              10              15
Arg (2) INFORMATION FOR SEQ ID NO:    117:

(i) SEQUENCE CHARACTERISTICS:
        (A) LENGTH:           20
        (B) TYPE:             amino acid
        (C) STRANDEDNESS:
        (D) TOPOLOGY:         linear (xi) SEQUENCE DESCRIPTION: SEQ ID NO: 117:

Asp Leu Ser Ser Trp Thr Ala Ala Asp Thr Ala Ala Gln Ile Thr Gln
 1               5              10              15
Arg Lys Trp Glu
            20

(2) INFORMATION FOR SEQ ID NO:    118:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 118:

Tyr Asp His Asn Phe Val Lys Ala Ile Asn Ala Asp Gln Lys Ser Trp
 1               5              10              15
Thr (2) INFORMATION FOR SEQ ID NO:    119:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 119:

Tyr Asp His Asn Phe Val Lys Ala Ile Asn Ala Asp Ile Lys Ser Trp
 1               5              10              15
Thr (2) INFORMATION FOR SEQ ID NO:    120:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 120:

Tyr Asp His Asn Phe Val Lys Ala Ile Asn Ala Asp Gln Lys Ser Trp
 1               5              10              15

(2) INFORMATION FOR SEQ ID NO:    121:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 121:

Tyr Asp His Asn Phe Val Lys Ala Ile Asn Ala Ile Gln Lys Ser Trp
```

```
          1               5              10             15
```

(2) INFORMATION FOR SEQ ID NO:    122:

(i) SEQUENCE CHARACTERISTICS:
        (A) LENGTH:            14
        (B) TYPE:              amino acid
        (C) STRANDEDNESS:
        (D) TOPOLOGY:          linear (xi) SEQUENCE DESCRIPTION: SEQ ID NO: 122:

```
Gly Asp Thr Arg Pro Arg Phe Leu Glu Gln Val Lys His Glu
  1               5                  10
```

(2) INFORMATION FOR SEQ ID NO:    123:

(i) SEQUENCE CHARACTERISTICS:
        (A) LENGTH:            17
        (B) TYPE:              amino acid
        (C) STRANDEDNESS:
        (D) TOPOLOGY:          linear (xi) SEQUENCE DESCRIPTION: SEQ ID NO: 123:

```
Gly Val Tyr Phe Tyr Leu Gln Trp Gly Arg Ser Thr Leu Val Ser Val
  1               5                  10                  15
Ser
```

(2) INFORMATION FOR SEQ ID NO:    124:

(i) SEQUENCE CHARACTERISTICS:
        (A) LENGTH:            20
        (B) TYPE:              amino acid
        (C) STRANDEDNESS:
        (D) TOPOLOGY:          linear (xi) SEQUENCE DESCRIPTION: SEQ ID NO: 124:

```
Arg Pro Ala Gly Asp Gly Thr Phe Gln Lys Trp Ala Ser Val Val Val
  1               5                  10                  15
Pro Ser Gly Gln
             20
```

(2) INFORMATION FOR SEQ ID NO:    125:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 125:

```
Arg Pro Ala Gly Asp Gly Thr Phe Gln Lys Trp Ala Ser Val Val Val
  1               5                  10                  15
```

(2) INFORMATION FOR SEQ ID NO:    126:

(i) SEQUENCE CHARACTERISTICS:
        (A) LENGTH:            22
        (B) TYPE:              amino acid
        (C) STRANDEDNESS:
        (D) TOPOLOGY:          linear (xi) SEQUENCE DESCRIPTION: SEQ ID NO: 126:

```
Gly Asp Gly Thr Phe Gln Lys Trp Ala Ser Val Val Val Pro Ser Gly
  1               5                  10                  15
Gln Glu Gln Arg Tyr Thr
             20
```

(2) INFORMATION FOR SEQ ID NO: 127:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 127:

```
Gly Asp Gly Thr Phe Gln Lys Trp Ala Ser Val Val Val Pro Ser Gly
 1               5                  10                  15
Gln Glu
```

(2) INFORMATION FOR SEQ ID NO: 128:

(i) SEQUENCE CHARACTERISTICS:
        (A) LENGTH: 14
        (B) TYPE: amino acid
        (C) STRANDEDNESS:
        (D) TOPOLOGY: linear (xi) SEQUENCE DESCRIPTION: SEQ ID NO: 128:

```
Gly Thr Phe Gln Lys Trp Ala Ser Val Val Val Pro Ser Gly
 1               5                  10
```

(2) INFORMATION FOR SEQ ID NO: 129:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 129:

```
Gly Thr Phe Gln Lys Trp Ala Ser Val Val Val Pro Ser Gly Gln
 1               5                  10                  15
```

(2) INFORMATION FOR SEQ ID NO: 130:

(i) SEQUENCE CHARACTERISTICS:
        (A) LENGTH: 23
        (B) TYPE: amino acid
        (C) STRANDEDNESS:
        (D) TOPOLOGY: linear (xi) SEQUENCE DESCRIPTION: SEQ ID NO: 130:

```
Gly Thr Phe Gln Lys Trp Ala Ser Val Val Val Pro Ser Gly Gln Glu
 1               5                  10                  15
Gln Arg Tyr Thr Cys His Val
                 20
```

(2) INFORMATION FOR SEQ ID NO: 131:

(i) SEQUENCE CHARACTERISTICS:
        (A) LENGTH: 21
        (B) TYPE: amino acid
        (C) STRANDEDNESS:
        (D) TOPOLOGY: linear (xi) SEQUENCE DESCRIPTION: SEQ ID NO: 131:

```
Gly Ala Leu Ala Asn Ile Ala Val Asp Lys Ala Asn Leu Glu Ile Met
 1               5                  10                  15
Thr Lys Arg Ser Asn
         20
```

(2) INFORMATION FOR SEQ ID NO: 132:

(i) SEQUENCE CHARACTERISTICS:
        (A) LENGTH:        17
        (B) TYPE:          amino acid
        (C) STRANDEDNESS:
        (D) TOPOLOGY:     linear (xi) SEQUENCE DESCRIPTION: SEQ ID NO: 132:

Thr Pro Ser Tyr Val Ala Phe Thr Asp Thr Glu Arg Leu Ile Gly Asp
1             5              10            15

Ala (2) INFORMATION FOR SEQ ID NO: 133:

(i) SEQUENCE CHARACTERISTICS:
        (A) LENGTH:        15
        (B) TYPE:          amino acid
        (C) STRANDEDNESS:
        (D) TOPOLOGY:     linear (xi) SEQUENCE DESCRIPTION: SEQ ID NO: 133:

Thr Pro Ser Tyr Val Ala Phe Thr Asp Thr Glu Arg Leu Ile Gly
1             5              10            15

(2) INFORMATION FOR SEQ ID NO: 134:

(i) SEQUENCE CHARACTERISTICS:
        (A) LENGTH:        16
        (B) TYPE:          amino acid
        (C) STRANDEDNESS:
        (D) TOPOLOGY:     linear (xi) SEQUENCE DESCRIPTION: SEQ ID NO: 134:

Arg Ser Glu Glu Phe Leu Ile Ala Gly Lys Leu Gln Asp Gly Leu Leu
1             5              10            15

(2) INFORMATION FOR SEQ ID NO: 135:

(i) SEQUENCE CHARACTERISTICS:
        (A) LENGTH:        15
        (B) TYPE:          amino acid
        (C) STRANDEDNESS:
        (D) TOPOLOGY:     linear (xi) SEQUENCE DESCRIPTION: SEQ ID NO: 135:

Ser Glu Glu Phe Leu Ile Ala Gly Lys Leu Gln Asp Gly Leu Leu
1             5              10            15

(2) INFORMATION FOR SEQ ID NO: 136:

(i) SEQUENCE CHARACTERISTICS:
        (A) LENGTH:        15
        (B) TYPE:          amino acid
        (C) STRANDEDNESS:
        (D) TOPOLOGY:     linear (xi) SEQUENCE DESCRIPTION: SEQ ID NO: 136:

Asp Val Ile Trp Glu Leu Leu Asn His Ala Gln Glu His Phe Gly
1             5              10            15

(2) INFORMATION FOR SEQ ID NO: 137:

(i) SEQUENCE CHARACTERISTICS:
        (A) LENGTH:        16
        (B) TYPE:          amino acid
        (C) STRANDEDNESS:

(D) TOPOLOGY:           linear (xi) SEQUENCE DESCRIPTION: SEQ ID NO: 137:

Glu Pro Phe Leu Tyr Ile Leu Gly Lys Ser Arg Val Leu Glu Ala Gln
 1               5                  10                  15

(2) INFORMATION FOR SEQ ID NO:    138:

(i) SEQUENCE CHARACTERISTICS:
            (A) LENGTH:             15
            (B) TYPE:               amino acid
            (C) STRANDEDNESS:
            (D) TOPOLOGY:           linear (xi) SEQUENCE DESCRIPTION: SEQ ID NO: 138:

Thr Ala Phe Gln Tyr Ile Ile Asp Asn Lys Gly Ile Asp Ser Asp
 1               5                  10                  15

(2) INFORMATION FOR SEQ ID NO:    139:

(i) SEQUENCE CHARACTERISTICS:
            (A) LENGTH:             14
            (B) TYPE:               amino acid
            (C) STRANDEDNESS:
            (D) TOPOLOGY:           linear (xi) SEQUENCE DESCRIPTION: SEQ ID NO: 139:

Thr Ala Phe Gln Tyr Ile Ile Asp Asn Lys Gly Ile Asp Ser
 1               5                  10

(2) INFORMATION FOR SEQ ID NO:    140:

(i) SEQUENCE CHARACTERISTICS:
            (A) LENGTH:             24
            (B) TYPE:               amino acid
            (C) STRANDEDNESS:
            (D) TOPOLOGY:           linear (xi) SEQUENCE DESCRIPTION: SEQ ID NO: 140:

Ser Glu Thr Val Phe Leu Pro Arg Glu Asp His Leu Phe Arg Lys Phe
 1               5                  10                  15

His Tyr Leu Pro Phe Leu Pro Ser
                20

(2) INFORMATION FOR SEQ ID NO:    141:

(i) SEQUENCE CHARACTERISTICS:
            (A) LENGTH:             21
            (B) TYPE:               amino acid
            (C) STRANDEDNESS:
            (D) TOPOLOGY:           linear (xi) SEQUENCE DESCRIPTION: SEQ ID NO: 141:

Val Phe Leu Pro Arg Glu Asp His Leu Phe Arg Lys Phe His Tyr Leu
 1               5                  10                  15

Pro Phe Leu Pro Ser
                20

(2) INFORMATION FOR SEQ ID NO:    142:

(i) SEQUENCE CHARACTERISTICS:
            (A) LENGTH:             20
            (B) TYPE:               amino acid
            (C) STRANDEDNESS:
            (D) TOPOLOGY:           linear (xi) SEQUENCE DESCRIPTION: SEQ ID NO: 142:

```
Val Phe Leu Pro Arg Glu Asp His Leu Phe Arg Lys Phe His Tyr Leu
  1               5                  10                  15

Pro Phe Leu Pro
            20

(2) INFORMATION FOR SEQ ID NO:    143:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 143:

Val Phe Leu Pro Arg Glu Asp His Leu Phe Arg Lys Phe His Tyr Leu
  1               5                  10                  15

(2) INFORMATION FOR SEQ ID NO:    144:

(i) SEQUENCE CHARACTERISTICS:
        (A) LENGTH:            26
        (B) TYPE:              amino acid
        (C) STRANDEDNESS:
        (D) TOPOLOGY:          linear (xi) SEQUENCE DESCRIPTION: SEQ ID NO: 144:

Lys Leu Gly His Pro Asp Thr Leu Asn Gln Gly Glu Phe Lys Glu Leu
  1               5                  10                  15

Val Arg Lys Asp Leu Gln Asn Phe Leu Lys
            20                  25

(2) INFORMATION FOR SEQ ID NO:    145:

(i) SEQUENCE CHARACTERISTICS:
        (A) LENGTH:            24
        (B) TYPE:              amino acid
        (C) STRANDEDNESS:
        (D) TOPOLOGY:          linear (xi) SEQUENCE DESCRIPTION: SEQ ID NO: 145:

Lys Leu Gly His Pro Asp Thr Leu Asn Gln Gly Glu Phe Lys Glu Leu
  1               5                  10                  15

Val Arg Lys Asp Leu Gln Asn Phe
            20

(2) INFORMATION FOR SEQ ID NO:    146:

(i) SEQUENCE CHARACTERISTICS:
        (A) LENGTH:            14
        (B) TYPE:              amino acid
        (C) STRANDEDNESS:
        (D) TOPOLOGY:          linear (xi) SEQUENCE DESCRIPTION: SEQ ID NO: 146:

Lys Leu Gly His Pro Asp Thr Leu Asn Gln Gly Glu Phe Lys
  1               5                  10

(2) INFORMATION FOR SEQ ID NO:    147:

(i) SEQUENCE CHARACTERISTICS:
        (A) LENGTH:            123
        (B) TYPE:              nucleic acid
        (C) STRANDEDNESS:      single
        (D) TOPOLOGY:          linear (xi) SEQUENCE DESCRIPTION: SEQ ID NO: 147:
```

```
ATG GCC ATA AGT GGA GTC CCT GTG CTA GGA TTT TTC ATC ATA GCT GTG    48
Met Ala Ile Ser Gly Val Pro Val Leu Gly Phe Phe Ile Ile Ala Val
1               5                   10                  15

CTG ATG AGC GCT CAG GAA TCA TGG GCT AAG ATG CGC ATG GCC ACC CCG    96
Leu Met Ser Ala Gln Glu Ser Trp Ala Lys Met Arg Met Ala Thr Pro
            20                  25                  30

CTG CTG ATG CAG GCG CTG CCC ATG TAA                               123
Leu Leu Met Gln Ala Leu Pro Met
        35                  40
```

(2) INFORMATION FOR SEQ ID NO:   148:

(i) SEQUENCE CHARACTERISTICS:
        (A) LENGTH:              150
        (B) TYPE:                nucleic acid
        (C) STRANDEDNESS:        single
        (D) TOPOLOGY:            linear (xi) SEQUENCE DESCRIPTION: SEQ ID NO: 148:

```
ATG GCC ATA AGT GGA GTC CCT GTG CTA GGA TTT TTC ATC ATA GCT GTG    48
Met Ala Ile Ser Gly Val Pro Val Leu Gly Phe Phe Ile Ile Ala Val
1               5                   10                  15

CTG ATG AGC GCT CAG GAA TCA TGG GCT CTT CCC AAG CCT CCC AAG CCT    96
Leu Met Ser Ala Gln Glu Ser Trp Ala Leu Pro Lys Pro Pro Lys Pro
            20                  25                  30

GTG AGC AAG ATG CGC ATG GCC ACC CCG CTG CTG ATG CAG GCG CTG CCC   144
Val Ser Lys Met Arg Met Ala Thr Pro Leu Leu Met Gln Ala Leu Pro
        35                  40                  45

ATG TAA                                                           150
Met
```

(2) INFORMATION FOR SEQ ID NO:   149:

(i) SEQUENCE CHARACTERISTICS:
        (A) LENGTH:              10
        (B) TYPE:                amino acid
        (C) STRANDEDNESS:
        (D) TOPOLOGY:            linear (xi) SEQUENCE DESCRIPTION: SEQ ID NO: 149:

```
Thr Gln Phe Val Arg Phe Asp Ser Asp Ala
1               5                   10
```

(2) INFORMATION FOR SEQ ID NO:   150:

(i) SEQUENCE CHARACTERISTICS:
        (A) LENGTH:              10
        (B) TYPE:                amino acid
        (C) STRANDEDNESS:
        (D) TOPOLOGY:            linear (xi) SEQUENCE DESCRIPTION: SEQ ID NO: 150:

```
Asp Trp Arg Phe Leu Arg Gly Tyr His Gln
1               5                   10
```

(2) INFORMATION FOR SEQ ID NO:   151:

(i) SEQUENCE CHARACTERISTICS:
        (A) LENGTH:              10
        (B) TYPE:                amino acid
        (C) STRANDEDNESS:
        (D) TOPOLOGY:            linear (xi) SEQUENCE DESCRIPTION: SEQ ID NO: 151:

Arg Met Ala Thr Pro Leu Leu Met Gln Ala

```
           1               5                   10
```

(2) INFORMATION FOR SEQ ID NO:   152:

(i) SEQUENCE CHARACTERISTICS:
        (A) LENGTH:           4
        (B) TYPE:             amino acid
        (C) STRANDEDNESS:
        (D) TOPOLOGY:         linear (xi) SEQUENCE DESCRIPTION: SEQ ID NO: 152:

```
Lys Asp Glu Leu
 1
```

(2) INFORMATION FOR SEQ ID NO:   153:

(i) SEQUENCE CHARACTERISTICS:
        (A) LENGTH:           5
        (B) TYPE:             amino acid
        (C) STRANDEDNESS:
        (D) TOPOLOGY:         linear (xi) SEQUENCE DESCRIPTION: SEQ ID NO: 153:

```
Lys Phe Glu Arg Gln
 1               5
```

(2) INFORMATION FOR SEQ ID NO:   154:

(i) SEQUENCE CHARACTERISTICS:
        (A) LENGTH:           5
        (B) TYPE:             amino acid
        (C) STRANDEDNESS:
        (D) TOPOLOGY:         linear (xi) SEQUENCE DESCRIPTION: SEQ ID NO: 154:

```
Gln Arg Glu Phe Lys
 1               5
```

(2) INFORMATION FOR SEQ ID NO:   155:

(i) SEQUENCE CHARACTERISTICS:
        (A) LENGTH:           25
        (B) TYPE:             amino acid
        (C) STRANDEDNESS:
        (D) TOPOLOGY:         linear (xi) SEQUENCE DESCRIPTION: SEQ ID NO: 155:

```
Met Ala Ile Ser Gly Val Pro Val Leu Gly Phe Phe Ile Ile Ala Val
 1               5                  10                  15

Leu Met Ser Ala Gln Glu Ser Trp Ala
             20                  25
```

(2) INFORMATION FOR SEQ ID NO:   156:

(i) SEQUENCE CHARACTERISTICS:
        (A) LENGTH:           14
        (B) TYPE:             amino acid
        (C) STRANDEDNESS:
        (D) TOPOLOGY:         linear (xi) SEQUENCE DESCRIPTION: SEQ ID NO: 156:

```
Met Arg Met Ala Thr Pro Leu Leu Met Gln Ala Leu Pro Met
 1               5                  10
```

(2) INFORMATION FOR SEQ ID NO:   157:

(i) SEQUENCE CHARACTERISTICS:

(A) LENGTH:           23
            (B) TYPE:             amino acid
            (C) STRANDEDNESS:
            (D) TOPOLOGY:         linear (xi) SEQUENCE DESCRIPTION: SEQ ID NO: 157:

Met Pro Arg Ser Arg Ala Leu Ile Leu Gly Val Leu Ala Leu Thr Thr
 1               5                  10                  15

Met Leu Ser Leu Cys Gly Gly
            20

(2) INFORMATION FOR SEQ ID NO:    158:

(i) SEQUENCE CHARACTERISTICS:
            (A) LENGTH:           23
            (B) TYPE:             amino acid
            (C) STRANDEDNESS:
            (D) TOPOLOGY:         linear (xi) SEQUENCE DESCRIPTION: SEQ ID NO: 158:

Asn Ile Val Ile Lys Arg Ser Asn Ser Thr Ala Ala Thr Asn Glu Val
 1               5                  10                  15

Pro Glu Val Thr Val Phe Ser
            20

(2) INFORMATION FOR SEQ ID NO:    159:

(i) SEQUENCE CHARACTERISTICS:
            (A) LENGTH:           16
            (B) TYPE:             amino acid
            (C) STRANDEDNESS:
            (D) TOPOLOGY:         linear (xi) SEQUENCE DESCRIPTION: SEQ ID NO: 159:

Asn Ile Val Ile Lys Arg Ser Asn Ser Thr Ala Ala Thr Asn Glu Val
 1               5                  10                  15

(2) INFORMATION FOR SEQ ID NO:    160:

(i) SEQUENCE CHARACTERISTICS:
            (A) LENGTH:           18
            (B) TYPE:             amino acid
            (C) STRANDEDNESS:
            (D) TOPOLOGY:         linear (xi) SEQUENCE DESCRIPTION: SEQ ID NO: 160:

Ser Asp Val Gly Val Tyr Arg Ala Val Thr Pro Gln Gly Arg Pro Asp
 1               5                  10                  15

Ala Glu (2) INFORMATION FOR SEQ ID NO:    161:

(i) SEQUENCE CHARACTERISTICS:
            (A) LENGTH:           17
            (B) TYPE:             amino acid
            (C) STRANDEDNESS:
            (D) TOPOLOGY:         linear (xi) SEQUENCE DESCRIPTION: SEQ ID NO: 161:

Asp Val Gly Val Tyr Arg Ala Val Thr Pro Gln Gly Arg Pro Asp Ala
 1               5                  10                  15

Glu (2) INFORMATION FOR SEQ ID NO:    162:

```
        (i) SEQUENCE CHARACTERISTICS:
            (A) LENGTH:             15
            (B) TYPE:               amino acid
            (C) STRANDEDNESS:
            (D) TOPOLOGY:           linear (xi) SEQUENCE DESCRIPTION: SEQ ID NO: 162:

Asp Val Gly Val Tyr Arg Ala Val Thr Pro Gln Gly Arg Pro Asp
 1               5                  10                  15

(2) INFORMATION FOR SEQ ID NO:   163:

(i) SEQUENCE CHARACTERISTICS:
            (A) LENGTH:             13
            (B) TYPE:               amino acid
            (C) STRANDEDNESS:
            (D) TOPOLOGY:           linear (xi) SEQUENCE DESCRIPTION: SEQ ID NO: 163:

Ala Pro Ser Pro Leu Pro Glu Thr Thr Glu Asn Val Val
 1               5                  10

(2) INFORMATION FOR SEQ ID NO:   164:

(i) SEQUENCE CHARACTERISTICS:
            (A) LENGTH:             17
            (B) TYPE:               amino acid
            (C) STRANDEDNESS:
            (D) TOPOLOGY:           linear (xi) SEQUENCE DESCRIPTION: SEQ ID NO: 164:

Ala Pro Ser Pro Leu Pro Glu Thr Thr Glu Asn Val Val Cys Ala Leu
 1               5                  10                  15

Gly (2) INFORMATION FOR SEQ ID NO:   165:

(i) SEQUENCE CHARACTERISTICS:
            (A) LENGTH:             21
            (B) TYPE:               amino acid
            (C) STRANDEDNESS:
            (D) TOPOLOGY:           linear (xi) SEQUENCE DESCRIPTION: SEQ ID NO: 165:

Phe Pro Lys Ser Leu His Thr Tyr Ala Asn Ile Leu Leu Asp Arg Arg
 1               5                  10                  15

Val Pro Gln Thr Asp
            20

(2) INFORMATION FOR SEQ ID NO:   166:

(i) SEQUENCE CHARACTERISTICS:
            (A) LENGTH:             19
            (B) TYPE:               amino acid
            (C) STRANDEDNESS:
            (D) TOPOLOGY:           linear (xi) SEQUENCE DESCRIPTION: SEQ ID NO: 166:

Phe Pro Lys Ser Leu His Thr Tyr Ala Asn Ile Leu Leu Asp Arg Arg
 1               5                  10                  15

Val Pro Gln (2) INFORMATION FOR SEQ ID NO:   167:

(i) SEQUENCE CHARACTERISTICS:
            (A) LENGTH:             18
```

```
            (B) TYPE:                amino acid
            (C) STRANDEDNESS:
            (D) TOPOLOGY:            linear (xi) SEQUENCE DESCRIPTION: SEQ ID NO: 167:

Asp Gly Ile Leu Tyr Tyr Tyr Gln Ser Gly Gly Arg Leu Arg Arg Pro
1               5                   10                  15

Val Asn (2) INFORMATION FOR SEQ ID NO:   168:

(i) SEQUENCE CHARACTERISTICS:
            (A) LENGTH:              17
            (B) TYPE:                amino acid
            (C) STRANDEDNESS:
            (D) TOPOLOGY:            linear (xi) SEQUENCE DESCRIPTION: SEQ ID NO: 168:

Asp Gly Ile Leu Tyr Tyr Tyr Gln Ser Gly Gly Arg Leu Arg Arg Pro
1               5                   10                  15

Val (2) INFORMATION FOR SEQ ID NO:   169:

(i) SEQUENCE CHARACTERISTICS:
            (A) LENGTH:              30
            (B) TYPE:                amino acid
            (C) STRANDEDNESS:
            (D) TOPOLOGY:            linear (xi) SEQUENCE DESCRIPTION: SEQ ID NO: 169:

Leu Ser Pro Ile His Ile Ala Leu Asn Phe Ser Leu Asp Pro Gln Ala
1               5                   10                  15

Pro Val Asp Ser His Gly Leu Arg Pro Ala Leu His Tyr Gln
            20                  25                  30

(2) INFORMATION FOR SEQ ID NO:   170:

(i) SEQUENCE CHARACTERISTICS:
            (A) LENGTH:              16
            (B) TYPE:                amino acid
            (C) STRANDEDNESS:
            (D) TOPOLOGY:            linear (xi) SEQUENCE DESCRIPTION: SEQ ID NO: 170:

Leu Trp Asp Tyr Gly Met Ser Ser Ser Pro His Val Leu Arg Asn Arg
1               5                   10                  15

(2) INFORMATION FOR SEQ ID NO:   171:

(i) SEQUENCE CHARACTERISTICS:
            (A) LENGTH:              16
            (B) TYPE:                amino acid
            (C) STRANDEDNESS:
            (D) TOPOLOGY:            linear (xi) SEQUENCE DESCRIPTION: SEQ ID NO: 171:

Val Asp Asp Thr Gln Phe Val Arg Phe Asp Ser Asp Ala Ala Ser Gln
1               5                   10                  15

(2) INFORMATION FOR SEQ ID NO:   172:

(i) SEQUENCE CHARACTERISTICS:
            (A) LENGTH:              19
            (B) TYPE:                amino acid
            (C) STRANDEDNESS:
```

-continued

```
        (D) TOPOLOGY:          linear (xi) SEQUENCE DESCRIPTION: SEQ ID NO: 172:

Pro Pro Glu Val Thr Val Leu Thr Asn Ser Pro Val Glu Leu Arg Glu
  1               5                  10                  15

Pro Asn Val (2) INFORMATION FOR SEQ ID NO:   173:

(i) SEQUENCE CHARACTERISTICS:
         (A) LENGTH:            18
         (B) TYPE:              amino acid
         (C) STRANDEDNESS:
         (D) TOPOLOGY:          linear (xi) SEQUENCE DESCRIPTION: SEQ ID NO: 173:

Pro Pro Glu Val Thr Val Leu Thr Asn Ser Pro Val Glu Leu Arg Glu
  1               5                  10                  15

Pro Asn (2) INFORMATION FOR SEQ ID NO:   174:

(i) SEQUENCE CHARACTERISTICS:
         (A) LENGTH:            16
         (B) TYPE:              amino acid
         (C) STRANDEDNESS:
         (D) TOPOLOGY:          linear (xi) SEQUENCE DESCRIPTION: SEQ ID NO: 174:

Val Phe Leu Leu Leu Leu Ala Asp Lys Val Pro Glu Thr Ser Leu Ser
  1               5                  10                  15

(2) INFORMATION FOR SEQ ID NO:   175:

(i) SEQUENCE CHARACTERISTICS:
         (A) LENGTH:            16
         (B) TYPE:              amino acid
         (C) STRANDEDNESS:
         (D) TOPOLOGY:          linear (xi) SEQUENCE DESCRIPTION: SEQ ID NO: 175:

Thr Phe Asp Glu Ile Ala Ser Gly Phe Arg Gln Gly Gly Ala Ser Gln
  1               5                  10                  15

(2) INFORMATION FOR SEQ ID NO:   176:

(i) SEQUENCE CHARACTERISTICS:
         (A) LENGTH:            14
         (B) TYPE:              amino acid
         (C) STRANDEDNESS:
         (D) TOPOLOGY:          linear (xi) SEQUENCE DESCRIPTION: SEQ ID NO: 176:

Tyr Gly Tyr Thr Ser Tyr Asp Thr Phe Ser Trp Ala Phe Leu
  1               5                  10

(2) INFORMATION FOR SEQ ID NO:   177:

(i) SEQUENCE CHARACTERISTICS:
         (A) LENGTH:            19
         (B) TYPE:              amino acid
         (C) STRANDEDNESS:
         (D) TOPOLOGY:          linear (xi) SEQUENCE DESCRIPTION: SEQ ID NO: 177:

Ala Thr Lys Tyr Gly Asn Met Thr Glu Asp His Val Met His Leu Leu
```

```
             1               5              10              15

Gln Asn Ala (2) INFORMATION FOR SEQ ID NO:   178:

(i) SEQUENCE CHARACTERISTICS:
        (A) LENGTH:            14
        (B) TYPE:              amino acid
        (C) STRANDEDNESS:
        (D) TOPOLOGY:          linear (xi) SEQUENCE DESCRIPTION: SEQ ID NO: 178:

Gly Gln Val Lys Lys Asn Asn His Gln Glu Asp Lys Ile Glu
 1               5                  10

(2) INFORMATION FOR SEQ ID NO:   179:

(i) SEQUENCE CHARACTERISTICS:
        (A) LENGTH:            13
        (B) TYPE:              amino acid
        (C) STRANDEDNESS:
        (D) TOPOLOGY:          linear (xi) SEQUENCE DESCRIPTION: SEQ ID NO: 179:

Leu Asn Lys Ile Leu Leu Asp Glu Gln Ala Gln Trp Lys
 1               5                  10

(2) INFORMATION FOR SEQ ID NO:   180:

(i) SEQUENCE CHARACTERISTICS:
        (A) LENGTH:            20
        (B) TYPE:              amino acid
        (C) STRANDEDNESS:
        (D) TOPOLOGY:          linear (xi) SEQUENCE DESCRIPTION: SEQ ID NO: 180:

Gly Pro Pro Lys Leu Asp Ile Arg Lys Glu Glu Lys Gln Ile Met Ile
 1               5                  10                  15

Asp Ile Phe His
             20

(2) INFORMATION FOR SEQ ID NO:   181:

(i) SEQUENCE CHARACTERISTICS:
        (A) LENGTH:            21
        (B) TYPE:              amino acid
        (C) STRANDEDNESS:
        (D) TOPOLOGY:          linear (xi) SEQUENCE DESCRIPTION: SEQ ID NO: 181:

Gly Pro Pro Lys Leu Asp Ile Arg Lys Glu Glu Lys Gln Ile Met Ile
 1               5                  10                  15

Asp Ile Phe His Pro
             20

(2) INFORMATION FOR SEQ ID NO:   182:

(i) SEQUENCE CHARACTERISTICS:
        (A) LENGTH:            22
        (B) TYPE:              amino acid
        (C) STRANDEDNESS:
        (D) TOPOLOGY:          linear (xi) SEQUENCE DESCRIPTION: SEQ ID NO: 182:

Ser Pro Leu Gln Ala Leu Asp Phe Phe Gly Asn Gly Pro Pro Val Asn
 1               5                  10                  15
```

```
Tyr Lys Thr Gly Asn Leu
            20
```

(2) INFORMATION FOR SEQ ID NO: 183:

(i) SEQUENCE CHARACTERISTICS:
        (A) LENGTH:         20
        (B) TYPE:           amino acid
        (C) STRANDEDNESS:
        (D) TOPOLOGY:      linear (xi) SEQUENCE DESCRIPTION: SEQ ID NO: 183:

```
Ser Pro Leu Gln Ala Leu Asp Phe Phe Gly Asn Gly Pro Pro Val Asn
 1               5                  10                  15
Tyr Lys Thr Gly
            20
```

(2) INFORMATION FOR SEQ ID NO: 184:

(i) SEQUENCE CHARACTERISTICS:
        (A) LENGTH:         18
        (B) TYPE:           amino acid
        (C) STRANDEDNESS:
        (D) TOPOLOGY:      linear (xi) SEQUENCE DESCRIPTION: SEQ ID NO: 184:

```
Gly Lys Phe Ala Ile Arg Pro Asp Lys Lys Ser Asn Pro Ile Ile Arg
 1               5                  10                  15
Thr Val
```

(2) INFORMATION FOR SEQ ID NO: 185:

(i) SEQUENCE CHARACTERISTICS:
        (A) LENGTH:         15
        (B) TYPE:           amino acid
        (C) STRANDEDNESS:
        (D) TOPOLOGY:      linear (xi) SEQUENCE DESCRIPTION: SEQ ID NO: 185:

```
Thr Gly His Gly Ala Arg Thr Ser Thr Glu Pro Thr Thr Asp Tyr
 1               5                  10                  15
```

(2) INFORMATION FOR SEQ ID NO: 186:

(i) SEQUENCE CHARACTERISTICS:
        (A) LENGTH:         13
        (B) TYPE:           amino acid
        (C) STRANDEDNESS:
        (D) TOPOLOGY:      linear (xi) SEQUENCE DESCRIPTION: SEQ ID NO: 186:

```
Lys Glu Leu Lys Arg Gln Tyr Glu Lys Lys Leu Arg Gln
 1               5                  10
```

(2) INFORMATION FOR SEQ ID NO: 187:

(i) SEQUENCE CHARACTERISTICS:
        (A) LENGTH:         12
        (B) TYPE:           amino acid
        (C) STRANDEDNESS:
        (D) TOPOLOGY:      linear (xi) SEQUENCE DESCRIPTION: SEQ ID NO: 187:

```
Asp Asp Thr Gln Phe Val Arg Phe Asp Ser Asp Ala
 1               5                  10
```

(2) INFORMATION FOR SEQ ID NO: 188:

(i) SEQUENCE CHARACTERISTICS:
        (A) LENGTH: 16
        (B) TYPE: amino acid
        (C) STRANDEDNESS:
        (D) TOPOLOGY: linear (xi) SEQUENCE DESCRIPTION: SEQ ID NO: 188:

```
Gly Pro Asp Gly Arg Leu Leu Arg Gly His Asn Gln Tyr Asp Gly Lys
 1               5                  10                  15
```

(2) INFORMATION FOR SEQ ID NO: 189:

(i) SEQUENCE CHARACTERISTICS:
        (A) LENGTH: 14
        (B) TYPE: amino acid
        (C) STRANDEDNESS:
        (D) TOPOLOGY: linear (xi) SEQUENCE DESCRIPTION: SEQ ID NO: 189:

```
Ile Ala Leu Leu Leu Met Ala Ser Gln Glu Pro Gln Arg Met
 1               5                  10
```

(2) INFORMATION FOR SEQ ID NO: 190:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQ ID NO: 190:

```
Ile Ala Leu Leu Leu Met Ala Ser Gln Glu Pro Gln Arg Met Ser Arg
 1               5                  10                  15
Asn Phe Val Arg
            20
```

(2) INFORMATION FOR SEQ ID NO: 191:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQ ID NO: 191:

```
Ile Pro Asp Asn Leu Phe Leu Lys Ser Asp Gly Arg Ile Lys Tyr Thr
 1               5                  10                  15
Leu Asn Lys Asn
            20
```

(2) INFORMATION FOR SEQ ID NO: 192:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 192:

```
Ile Pro Asp Asn Leu Phe Leu Lys Ser Asp Gly Arg Ile Lys Tyr Thr
 1               5                  10                  15
Leu Asn
```

(2) INFORMATION FOR SEQ ID NO: 193:

(i) SEQUENCE CHARACTERISTICS:
        (A) LENGTH:         17
        (B) TYPE:           amino acid
        (C) STRANDEDNESS:
        (D) TOPOLOGY:      linear (xi) SEQUENCE DESCRIPTION: SEQ ID NO: 193:

```
Ile Pro Asp Asn Leu Phe Leu Lys Ser Asp Gly Arg Ile Lys Tyr Thr
 1               5                  10                  15
Leu
```

(2) INFORMATION FOR SEQ ID NO: 194:

(i) SEQUENCE CHARACTERISTICS:
        (A) LENGTH:         17
        (B) TYPE:           amino acid
        (C) STRANDEDNESS:
        (D) TOPOLOGY:      linear (xi) SEQUENCE DESCRIPTION: SEQ ID NO: 194:

```
Val Thr Thr Leu Asn Ser Asp Leu Lys Tyr Asn Ala Leu Asp Leu Thr
 1               5                  10                  15
Asn
```

(2) INFORMATION FOR SEQ ID NO: 195:

(i) SEQUENCE CHARACTERISTICS:
        (A) LENGTH:         23
        (B) TYPE:           amino acid
        (C) STRANDEDNESS:
        (D) TOPOLOGY:      linear (xi) SEQUENCE DESCRIPTION: SEQ ID NO: 195:

```
Val Asp Asp Thr Gln Phe Val Arg Phe Asp Ser Asp Ala Ala Ser Gln
 1               5                  10                  15
Arg Met Glu Pro Arg Ala Pro
                20
```

(2) INFORMATION FOR SEQ ID NO: 196:

(i) SEQUENCE CHARACTERISTICS:
        (A) LENGTH:         13
        (B) TYPE:           amino acid
        (C) STRANDEDNESS:
        (D) TOPOLOGY:      linear (xi) SEQUENCE DESCRIPTION: SEQ ID NO: 196:

```
Asp Val Ile Trp Glu Leu Leu Asn His Ala Gln Glu His
 1               5                  10
```

(2) INFORMATION FOR SEQ ID NO: 197:

(i) SEQUENCE CHARACTERISTICS:
        (A) LENGTH:         19
        (B) TYPE:           amino acid
        (C) STRANDEDNESS:
        (D) TOPOLOGY:      linear (xi) SEQUENCE DESCRIPTION: SEQ ID NO: 197:

```
Asp Leu Arg Ser Trp Thr Ala Ala Asp Thr Ala Ala Gln Ile Thr Gln
 1               5                  10                  15
Arg Lys Trp
```

```
(2) INFORMATION FOR SEQ ID NO:     198:

(i) SEQUENCE CHARACTERISTICS:
        (A) LENGTH:          18
        (B) TYPE:            amino acid
        (C) STRANDEDNESS:
        (D) TOPOLOGY:        linear (xi) SEQUENCE DESCRIPTION: SEQ ID NO: 198:

Leu Arg Ser Trp Thr Ala Ala Asp Thr Ala Ala Gln Ile Thr Gln Arg
 1               5                  10                  15

Lys Trp (2) INFORMATION FOR SEQ ID NO:     199:

(i) SEQUENCE CHARACTERISTICS:
        (A) LENGTH:          22
        (B) TYPE:            amino acid
        (C) STRANDEDNESS:
        (D) TOPOLOGY:        linear (xi) SEQUENCE DESCRIPTION: SEQ ID NO: 199:

Asp Leu Ser Ser Trp Thr Ala Ala Asp Thr Ala Ala Gln Ile Thr Gln
 1               5                  10                  15

Arg Lys Trp Glu Ala Ala
            20

(2) INFORMATION FOR SEQ ID NO:     200:

(i) SEQUENCE CHARACTERISTICS:
        (A) LENGTH:          18
        (B) TYPE:            amino acid
        (C) STRANDEDNESS:
        (D) TOPOLOGY:        linear (xi) SEQUENCE DESCRIPTION: SEQ ID NO: 200:

Asp Leu Ser Ser Trp Thr Ala Ala Asp Thr Ala Ala Gln Ile Thr Gln
 1               5                  10                  15

Arg Lys (2) INFORMATION FOR SEQ ID NO:     201:

(i) SEQUENCE CHARACTERISTICS:
        (A) LENGTH:          20
        (B) TYPE:            amino acid
        (C) STRANDEDNESS:
        (D) TOPOLOGY:        linear (xi) SEQUENCE DESCRIPTION: SEQ ID NO: 201:

Gly Ser Leu Phe Val Tyr Asn Ile Thr Thr Asn Lys Tyr Lys Ala Phe
 1               5                  10                  15

Leu Asp Lys Gln
            20

(2) INFORMATION FOR SEQ ID NO:     202:

(i) SEQUENCE CHARACTERISTICS:
        (A) LENGTH:          16
        (B) TYPE:            amino acid
        (C) STRANDEDNESS:
        (D) TOPOLOGY:        linear (xi) SEQUENCE DESCRIPTION: SEQ ID NO: 202:

Gly Ser Leu Phe Val Tyr Asn Ile Thr Thr Asn Lys Tyr Lys Ala Phe
 1               5                  10                  15
```

(2) INFORMATION FOR SEQ ID NO:    203:

(i) SEQUENCE CHARACTERISTICS:
        (A) LENGTH:            21
        (B) TYPE:              amino acid
        (C) STRANDEDNESS:
        (D) TOPOLOGY:          linear (xi) SEQUENCE DESCRIPTION: SEQ ID NO: 203:

```
Ala Ala Pro Tyr Glu Lys Glu Val Pro Leu Ser Ala Leu Thr Asn Ile
 1               5                  10                  15

Leu Ser Ala Gln Leu
            20
```

(2) INFORMATION FOR SEQ ID NO:    204:

(i) SEQUENCE CHARACTERISTICS:
        (A) LENGTH:            18
        (B) TYPE:              amino acid
        (C) STRANDEDNESS:
        (D) TOPOLOGY:          linear (xi) SEQUENCE DESCRIPTION: SEQ ID NO: 204:

```
Ala Ala Pro Tyr Glu Lys Glu Val Pro Leu Ser Ala Leu Thr Asn Ile
 1               5                  10                  15

Leu Ser
```

(2) INFORMATION FOR SEQ ID NO:    205:

(i) SEQUENCE CHARACTERISTICS:
        (A) LENGTH:            16
        (B) TYPE:              amino acid
        (C) STRANDEDNESS:
        (D) TOPOLOGY:          linear (xi) SEQUENCE DESCRIPTION: SEQ ID NO: 205:

```
Ala Glu Ala Leu Glu Arg Met Phe Leu Ser Phe Pro Thr Thr Lys Thr
 1               5                  10                  15
```

(2) INFORMATION FOR SEQ ID NO:    206:

(i) SEQUENCE CHARACTERISTICS:
        (A) LENGTH:            15
        (B) TYPE:              amino acid
        (C) STRANDEDNESS:
        (D) TOPOLOGY:          linear (xi) SEQUENCE DESCRIPTION: SEQ ID NO: 206:

```
Ser Pro Glu Asp Phe Val Tyr Gln Phe Lys Gly Met Cys Tyr Phe
 1               5                  10                  15
```

(2) INFORMATION FOR SEQ ID NO:    207:

(i) SEQUENCE CHARACTERISTICS:
        (A) LENGTH:            20
        (B) TYPE:              amino acid
        (C) STRANDEDNESS:
        (D) TOPOLOGY:          linear (xi) SEQUENCE DESCRIPTION: SEQ ID NO: 207:

```
Ser Asp Trp Arg Phe Leu Arg Gly Tyr His Gln Tyr Ala Tyr Asp Gly
 1               5                  10                  15

Lys Asp Tyr Ile
            20
```

(2) INFORMATION FOR SEQ ID NO: 208:

(i) SEQUENCE CHARACTERISTICS:
        (A) LENGTH:           14
        (B) TYPE:             amino acid
        (C) STRANDEDNESS:
        (D) TOPOLOGY:       linear (xi) SEQUENCE DESCRIPTION: SEQ ID NO: 208:

Gly Ser Asp Trp Arg Phe Leu Arg Gly Tyr His Gln Tyr Ala
1             5                10

(2) INFORMATION FOR SEQ ID NO: 209:

(i) SEQUENCE CHARACTERISTICS:
        (A) LENGTH:           13
        (B) TYPE:             amino acid
        (C) STRANDEDNESS:
        (D) TOPOLOGY:       linear (xi) SEQUENCE DESCRIPTION: SEQ ID NO: 209:

Gly Ser Asp Trp Arg Phe Leu Arg Gly Tyr His Gln Tyr
1             5                10

(2) INFORMATION FOR SEQ ID NO: 210:

(i) SEQUENCE CHARACTERISTICS:
        (A) LENGTH:           13
        (B) TYPE:             amino acid
        (C) STRANDEDNESS:
        (D) TOPOLOGY:       linear (xi) SEQUENCE DESCRIPTION: SEQ ID NO: 210:

Ser Asp Trp Arg Phe Leu Arg Gly Tyr His Gln Tyr Ala
1             5                10

(2) INFORMATION FOR SEQ ID NO: 211:

(i) SEQUENCE CHARACTERISTICS:
        (A) LENGTH:           17
        (B) TYPE:             amino acid
        (C) STRANDEDNESS:
        (D) TOPOLOGY:       linear (xi) SEQUENCE DESCRIPTION: SEQ ID NO: 211:

Arg Glu Thr Gln Ile Ser Lys Thr Asn Thr Gln Thr Tyr Arg Glu Asn
1             5                10              15

Leu (2) INFORMATION FOR SEQ ID NO: 212:

(i) SEQUENCE CHARACTERISTICS:
        (A) LENGTH:           16
        (B) TYPE:             amino acid
        (C) STRANDEDNESS:
        (D) TOPOLOGY:       linear (xi) SEQUENCE DESCRIPTION: SEQ ID NO: 212:

Arg Glu Thr Gln Ile Ser Lys Thr Asn Thr Gln Thr Tyr Arg Glu Asn
1             5                10              15

(2) INFORMATION FOR SEQ ID NO: 213:

(i) SEQUENCE CHARACTERISTICS:
        (A) LENGTH:           15
        (B) TYPE:             amino acid
        (C) STRANDEDNESS:
        (D) TOPOLOGY:       linear (xi) SEQUENCE DESCRIPTION: SEQ ID NO: 213:

Arg Glu Thr Gln Ile Ser Lys Thr Asn Thr Gln Thr Tyr Arg Glu
1               5                   10                  15

(2) INFORMATION FOR SEQ ID NO: 214:

(i) SEQUENCE CHARACTERISTICS:
        (A) LENGTH:           26
        (B) TYPE:             amino acid
        (C) STRANDEDNESS:
        (D) TOPOLOGY:         linear (xi) SEQUENCE DESCRIPTION: SEQ ID NO: 214:

Arg Ser Asn Tyr Thr Pro Ile Thr Asn Pro Pro Glu Val Thr Val Leu
1               5                   10                  15

Thr Asn Ser Pro Val Glu Leu Arg Glu Pro
            20                  25

(2) INFORMATION FOR SEQ ID NO: 215:

(i) SEQUENCE CHARACTERISTICS:
        (A) LENGTH:           20
        (B) TYPE:             amino acid
        (C) STRANDEDNESS:
        (D) TOPOLOGY:         linear (xi) SEQUENCE DESCRIPTION: SEQ ID NO: 215:

Ala Pro Ser Pro Leu Pro Glu Thr Thr Glu Asn Val Val Cys Ala Leu
1               5                   10                  15

Gly Leu Thr Val
            20

(2) INFORMATION FOR SEQ ID NO: 216:

(i) SEQUENCE CHARACTERISTICS:
        (A) LENGTH:           30
        (B) TYPE:             amino acid
        (C) STRANDEDNESS:
        (D) TOPOLOGY:         linear (xi) SEQUENCE DESCRIPTION: SEQ ID NO: 216:

Ser Leu Gln Ser Pro Ile Thr Val Glu Trp Arg Ala Gln Ser Glu Ser
1               5                   10                  15

Ala Gln Ser Lys Met Leu Ser Gly Ile Gly Gly Phe Val Leu
            20                  25                  30

(2) INFORMATION FOR SEQ ID NO: 217:

(i) SEQUENCE CHARACTERISTICS:
        (A) LENGTH:           21
        (B) TYPE:             amino acid
        (C) STRANDEDNESS:
        (D) TOPOLOGY:         linear (xi) SEQUENCE DESCRIPTION: SEQ ID NO: 217:

Val Thr Gln Tyr Leu Asn Ala Thr Gly Asn Arg Trp Cys Ser Trp Ser
1               5                   10                  15

Leu Ser Gln Ala Arg
            20

(2) INFORMATION FOR SEQ ID NO: 218:

(i) SEQUENCE CHARACTERISTICS:
        (A) LENGTH:           17

```
            (B) TYPE:              amino acid
            (C) STRANDEDNESS:
            (D) TOPOLOGY:          linear (xi) SEQUENCE DESCRIPTION: SEQ ID NO: 218:

Val Thr Gln Tyr Leu Asn Ala Thr Gly Asn Arg Trp Cys Ser Trp Ser
 1               5                  10                  15
Leu (2) INFORMATION FOR SEQ ID NO:   219:

(i) SEQUENCE CHARACTERISTICS:
            (A) LENGTH:            13
            (B) TYPE:              amino acid
            (C) STRANDEDNESS:
            (D) TOPOLOGY:          linear (xi) SEQUENCE DESCRIPTION: SEQ ID NO: 219:

Thr Ser Ile Leu Cys Tyr Arg Lys Arg Glu Trp Ile Lys
 1               5                  10

(2) INFORMATION FOR SEQ ID NO:   220:

(i) SEQUENCE CHARACTERISTICS:
            (A) LENGTH:            14
            (B) TYPE:              amino acid
            (C) STRANDEDNESS:
            (D) TOPOLOGY:          linear (xi) SEQUENCE DESCRIPTION: SEQ ID NO: 220:

Lys His Lys Val Tyr Ala Cys Glu Val Thr His Gln Gly Leu
 1               5                  10

(2) INFORMATION FOR SEQ ID NO:   221:

(i) SEQUENCE CHARACTERISTICS:
            (A) LENGTH:            13
            (B) TYPE:              amino acid
            (C) STRANDEDNESS:
            (D) TOPOLOGY:          linear (xi) SEQUENCE DESCRIPTION: SEQ ID NO: 221:

Lys His Lys Val Tyr Ala Cys Glu Val Thr His Gln Gly
 1               5                  10

(2) INFORMATION FOR SEQ ID NO:   222:

(i) SEQUENCE CHARACTERISTICS:
            (A) LENGTH:            25
            (B) TYPE:              amino acid
            (C) STRANDEDNESS:
            (D) TOPOLOGY:          linear (xi) SEQUENCE DESCRIPTION: SEQ ID NO: 222:

Gly Asp Met Tyr Pro Lys Thr Trp Ser Gly Met Leu Val Gly Ala Leu
 1               5                  10                  15
Cys Ala Leu Ala Gly Val Leu Thr Ile
                20                  25

(2) INFORMATION FOR SEQ ID NO:   223:

(i) SEQUENCE CHARACTERISTICS:
            (A) LENGTH:            19
            (B) TYPE:              amino acid
            (C) STRANDEDNESS:
            (D) TOPOLOGY:          linear
```

(xi) SEQUENCE DESCRIPTION: SEQ ID NO: 223:

Ala Pro Val Leu Ile Ser Gln Lys Leu Ser Pro Ile Tyr Asn Leu Val
  1               5                  10                  15
Pro Val Lys (2) INFORMATION FOR SEQ ID NO:    224:

(i) SEQUENCE CHARACTERISTICS:
            (A) LENGTH:           15
            (B) TYPE:             amino acid
            (C) STRANDEDNESS:
            (D) TOPOLOGY:         linear (xi) SEQUENCE DESCRIPTION: SEQ ID NO: 224:

Pro Ala Phe Arg Phe Thr Arg Glu Ala Ala Gln Asp Cys Glu Val
  1               5                  10                  15

(2) INFORMATION FOR SEQ ID NO:    225:

(i) SEQUENCE CHARACTERISTICS:
            (A) LENGTH:           18
            (B) TYPE:             amino acid
            (C) STRANDEDNESS:
            (D) TOPOLOGY:         linear (xi) SEQUENCE DESCRIPTION: SEQ ID NO: 225:

Val Pro Gly Leu Tyr Ser Pro Cys Arg Ala Phe Phe Asn Lys Glu Glu
  1               5                  10                  15
Leu Leu (2) INFORMATION FOR SEQ ID NO:    226:

(i) SEQUENCE CHARACTERISTICS:
            (A) LENGTH:           14
            (B) TYPE:             amino acid
            (C) STRANDEDNESS:
            (D) TOPOLOGY:         linear (xi) SEQUENCE DESCRIPTION: SEQ ID NO: 226:

Val Pro Gly Leu Tyr Ser Pro Cys Arg Ala Phe Phe Asn Lys
  1               5                  10

(2) INFORMATION FOR SEQ ID NO:    227:

(i) SEQUENCE CHARACTERISTICS:
            (A) LENGTH:           23
            (B) TYPE:             amino acid
            (C) STRANDEDNESS:
            (D) TOPOLOGY:         linear (xi) SEQUENCE DESCRIPTION: SEQ ID NO: 227:

Lys Val Asp Leu Thr Phe Ser Lys Gln His Ala Leu Leu Cys Ser Asp
  1               5                  10                  15
Tyr Gln Ala Asp Tyr Glu Ser
                 20

(2) INFORMATION FOR SEQ ID NO:    228:

(i) SEQUENCE CHARACTERISTICS:
            (A) LENGTH:           15
            (B) TYPE:             amino acid
            (C) STRANDEDNESS:
            (D) TOPOLOGY:         linear (xi) SEQUENCE DESCRIPTION: SEQ ID NO: 228:

```
Lys Val Asp Leu Thr Phe Ser Lys Gln His Ala Leu Leu Cys Ser
1               5                   10                  15

(2) INFORMATION FOR SEQ ID NO:     229:

(i) SEQUENCE CHARACTERISTICS:
        (A) LENGTH:             13
        (B) TYPE:               amino acid
        (C) STRANDEDNESS:
        (D) TOPOLOGY:           linear (xi) SEQUENCE DESCRIPTION: SEQ ID NO: 229:

Phe Ser His Asp Tyr Arg Gly Ser Thr Ser His Arg Leu
1               2                   10

(2) INFORMATION FOR SEQ ID NO:     230:

(i) SEQUENCE CHARACTERISTICS:
        (A) LENGTH:             13
        (B) TYPE:               amino acid
        (C) STRANDEDNESS:
        (D) TOPOLOGY:           linear (xi) SEQUENCE DESCRIPTION: SEQ ID NO: 230:

Leu Pro Lys Tyr Phe Glu Lys Lys Arg Asn Thr Ile Ile
1               5                   10

(2) INFORMATION FOR SEQ ID NO:     231:

(i) SEQUENCE CHARACTERISTICS:
        (A) LENGTH:             23
        (B) TYPE:               amino acid
        (C) STRANDEDNESS:
        (D) TOPOLOGY:           linear (xi) SEQUENCE DESCRIPTION: SEQ ID NO: 231:

Ser Glu Thr Val Phe Leu Pro Arg Glu Asp His Leu Phe Arg Lys Phe
1               5                   10                  15

His Tyr Leu Pro Phe Leu Pro
            20

(2) INFORMATION FOR SEQ ID NO:     232:

(i) SEQUENCE CHARACTERISTICS:
        (A) LENGTH:             18
        (B) TYPE:               amino acid
        (C) STRANDEDNESS:
        (D) TOPOLOGY:           linear (xi) SEQUENCE DESCRIPTION: SEQ ID NO: 232:

Ala Pro Ser Pro Leu Pro Glu Glu Thr Thr Glu Asn Val Val Cys Ala
1               5                   10                  15

Leu Gly (2) INFORMATION FOR SEQ ID NO:     233:

(i) SEQUENCE CHARACTERISTICS:
        (A) LENGTH:             24
        (B) TYPE:               amino acid
        (C) STRANDEDNESS:
        (D) TOPOLOGY:           linear (xi) SEQUENCE DESCRIPTION: SEQ ID NO: 233:

Gly Asp Thr Arg Pro Arg Phe Leu Glu Tyr Ser Thr Gly Glu Cys Tyr
1               5                   10                  15

Phe Phe Asn Gly Thr Glu Arg Val
```

20

(2) INFORMATION FOR SEQ ID NO: 234:

(i) SEQUENCE CHARACTERISTICS:
        (A) LENGTH:         13
        (B) TYPE:           amino acid
        (C) STRANDEDNESS:
        (D) TOPOLOGY:       linear (xi) SEQUENCE DESCRIPTION: SEQ ID NO: 234:

Arg His Asn Tyr Glu Leu Asp Glu Ala Val Thr Leu Gln
 1               5                  10

(2) INFORMATION FOR SEQ ID NO: 235:

(i) SEQUENCE CHARACTERISTICS:
        (A) LENGTH:         21
        (B) TYPE:           amino acid
        (C) STRANDEDNESS:
        (D) TOPOLOGY:       linear (xi) SEQUENCE DESCRIPTION: SEQ ID NO: 235:

Asp Pro Gln Ser Gly Ala Leu Tyr Ile Ser Lys Val Gln Lys Glu Asp
 1               5                  10                  15

Asn Ser Thr Tyr Ile
            20

(2) INFORMATION FOR SEQ ID NO: 236:

(i) SEQUENCE CHARACTERISTICS:
        (A) LENGTH:         17
        (B) TYPE:           amino acid
        (C) STRANDEDNESS:
        (D) TOPOLOGY:       linear (xi) SEQUENCE DESCRIPTION: SEQ ID NO: 236:

Gly Ala Leu Tyr Ile Ser Lys Val Gln Lys Glu Asp Asn Ser Thr Tyr
 1               5                  10                  15

Ile (2) INFORMATION FOR SEQ ID NO: 237:

(i) SEQUENCE CHARACTERISTICS:
        (A) LENGTH:         18
        (B) TYPE:           amino acid
        (C) STRANDEDNESS:
        (D) TOPOLOGY:       linear (xi) SEQUENCE DESCRIPTION: SEQ ID NO: 237:

Asp Pro Val Pro Lys Pro Val Ile Lys Ile Glu Lys Ile Glu Asp Met
 1               5                  10                  15

Asp Asp (2) INFORMATION FOR SEQ ID NO: 238:

(i) SEQUENCE CHARACTERISTICS:
        (A) LENGTH:         15
        (B) TYPE:           amino acid
        (C) STRANDEDNESS:
        (D) TOPOLOGY:       linear (xi) SEQUENCE DESCRIPTION: SEQ ID NO: 238:

Asp Pro Val Pro Lys Pro Val Ile Lys Ile Glu Lys Ile Glu Asp
 1               5                  10                  15

(2) INFORMATION FOR SEQ ID NO:   239:

(i) SEQUENCE CHARACTERISTICS:
        (A) LENGTH:           18
        (B) TYPE:             amino acid
        (C) STRANDEDNESS:
        (D) TOPOLOGY:         linear (xi) SEQUENCE DESCRIPTION: SEQ ID NO: 239:

```
Phe Thr Phe Thr Ile Ser Arg Leu Glu Pro Glu Asp Phe Ala Val Tyr
 1               5                  10                  15

Tyr Cys
```

(2) INFORMATION FOR SEQ ID NO:   240:

(i) SEQUENCE CHARACTERISTICS:
        (A) LENGTH:           15
        (B) TYPE:             amino acid
        (C) STRANDEDNESS:
        (D) TOPOLOGY:         linear (xi) SEQUENCE DESCRIPTION: SEQ ID NO: 240:

```
Phe Thr Phe Thr Ile Ser Arg Leu Glu Pro Glu Asp Phe Ala Val
 1               5                  10                  15
```

(2) INFORMATION FOR SEQ ID NO:   241:

(i) SEQUENCE CHARACTERISTICS:
        (A) LENGTH:           14
        (B) TYPE:             amino acid
        (C) STRANDEDNESS:
        (D) TOPOLOGY:         linear (xi) SEQUENCE DESCRIPTION: SEQ ID NO: 241:

```
Asp Pro Val Glu Met Arg Arg Leu Asn Tyr Gln Thr Pro Gly
 1               5                  10
```

(2) INFORMATION FOR SEQ ID NO:   242:

(i) SEQUENCE CHARACTERISTICS:
        (A) LENGTH:           18
        (B) TYPE:             amino acid
        (C) STRANDEDNESS:
        (D) TOPOLOGY:         linear (xi) SEQUENCE DESCRIPTION: SEQ ID NO: 242:

```
Tyr Gln Leu Leu Arg Ser Met Ile Gly Tyr Ile Glu Glu Leu Ala Pro
 1               5                  10                  15

Ile Val
```

(2) INFORMATION FOR SEQ ID NO:   243:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 243:

```
Gly Asn His Leu Tyr Lys Trp Lys Gln Ile Pro Asp Cys Glu Asn Val
 1               5                  10                  15

Lys
```

(2) INFORMATION FOR SEQ ID NO:   244:

```
    (i) SEQUENCE CHARACTERISTICS:
        (A) LENGTH:          20
        (B) TYPE:            amino acid
        (C) STRANDEDNESS:
        (D) TOPOLOGY:        linear (xi) SEQUENCE DESCRIPTION: SEQ ID NO: 244:

Leu Pro Phe Phe Leu Phe Arg Gln Ala Tyr His Pro Asn Asn Ser Ser
 1               5                  10                  15

Pro Val Cys Tyr
            20

(2) INFORMATION FOR SEQ ID NO:   245:

(i) SEQUENCE CHARACTERISTICS:
        (A) LENGTH:          28
        (B) TYPE:            amino acid
        (C) STRANDEDNESS:
        (D) TOPOLOGY:        linear (xi) SEQUENCE DESCRIPTION: SEQ ID NO: 245:

Gln Ala Lys Phe Phe Ala Cys Ile Lys Arg Ser Asp Gly Ser Cys Ala
 1               5                  10                  15

Trp Tyr Arg Gly Ala Ala Pro Pro Lys Gln Glu Phe
            20                  25

(2) INFORMATION FOR SEQ ID NO:   246:

(i) SEQUENCE CHARACTERISTICS:
        (A) LENGTH:          19
        (B) TYPE:            amino acid
        (C) STRANDEDNESS:
        (D) TOPOLOGY:        linear (xi) SEQUENCE DESCRIPTION: SEQ ID NO: 246:

Gln Ala Lys Phe Phe Ala Cys Ile Lys Arg Ser Asp Gly Ser Cys Ala
 1               5                  10                  15

Trp Tyr Arg (2) INFORMATION FOR SEQ ID NO:   247:

(i) SEQUENCE CHARACTERISTICS:
        (A) LENGTH:          15
        (B) TYPE:            amino acid
        (C) STRANDEDNESS:
        (D) TOPOLOGY:        linear (xi) SEQUENCE DESCRIPTION: SEQ ID NO: 247:

Ser Glu Glu Phe Leu Ile Ala Gly Lys Leu Gln Asp Gly Leu Leu
 1               5                  10                  15

(2) INFORMATION FOR SEQ ID NO:   248:

(i) SEQUENCE CHARACTERISTICS:
        (A) LENGTH:          12
        (B) TYPE:            amino acid
        (C) STRANDEDNESS:
        (D) TOPOLOGY:        linear (xi) SEQUENCE DESCRIPTION: SEQ ID NO: 248:

Asn Arg Ser Glu Glu Phe Leu Ile Ala Gly Lys Leu
 1               5                  10

(2) INFORMATION FOR SEQ ID NO:   249:

(i) SEQUENCE CHARACTERISTICS:
```

```
            (A) LENGTH:           24
            (B) TYPE:             amino acid
            (C) STRANDEDNESS:
            (D) TOPOLOGY:         linear (xi) SEQUENCE DESCRIPTION: SEQ ID NO: 249:

Gln Asn Phe Thr Val Ile Phe Asp Thr Gly Ser Ser Asn Leu Trp Val
 1               5                  10                  15
Pro Ser Val Tyr Cys Thr Ser Pro
             20

(2) INFORMATION FOR SEQ ID NO:   250:

(i) SEQUENCE CHARACTERISTICS:
            (A) LENGTH:           18
            (B) TYPE:             amino acid
            (C) STRANDEDNESS:
            (D) TOPOLOGY:         linear (xi) SEQUENCE DESCRIPTION: SEQ ID NO: 250:

Asp Glu Tyr Tyr Arg Arg Leu Leu Arg Val Leu Arg Ala Arg Glu Gln
 1               5                  10                  15
Ile Val (2) INFORMATION FOR SEQ ID NO:   251:

(i) SEQUENCE CHARACTERISTICS:
            (A) LENGTH:           17
            (B) TYPE:             amino acid
            (C) STRANDEDNESS:
            (D) TOPOLOGY:         linear (xi) SEQUENCE DESCRIPTION: SEQ ID NO: 251:

Glu Ala Ile Tyr Asp Ile Cys Arg Arg Asn Leu Asp Ile Glu Arg Pro
 1               5                  10                  15
Thr (2) INFORMATION FOR SEQ ID NO:   252:

(i) SEQUENCE CHARACTERISTICS:
            (A) LENGTH:           13
            (B) TYPE:             amino acid
            (C) STRANDEDNESS:
            (D) TOPOLOGY:         linear (xi) SEQUENCE DESCRIPTION: SEQ ID NO: 252:

Glu Ala Ile Tyr Asp Ile Cys Arg Arg Asn Leu Asp Ile
 1               5                  10

(2) INFORMATION FOR SEQ ID NO:   253:

(i) SEQUENCE CHARACTERISTICS:
            (A) LENGTH:           21
            (B) TYPE:             amino acid
            (C) STRANDEDNESS:
            (D) TOPOLOGY:         linear (xi) SEQUENCE DESCRIPTION: SEQ ID NO: 253:

His Glu Leu Glu Lys Ile Lys Lys Gln Val Glu Gln Glu Lys Cys Glu
 1               5                  10                  15
Ile Gln Ala Ala Leu
             20

(2) INFORMATION FOR SEQ ID NO:   254:
```

```
    (i) SEQUENCE CHARACTERISTICS:
         (A) LENGTH:              10
         (B) TYPE:                amino acid
         (C) STRANDEDNESS:
         (D) TOPOLOGY:            linear (xi) SEQUENCE DESCRIPTION: SEQ ID NO: 254:

Arg Pro Ser Met Leu Gln His Leu Leu Arg
 1               5                  10

(2) INFORMATION FOR SEQ ID NO:   255:

(i) SEQUENCE CHARACTERISTICS:
         (A) LENGTH:              22
         (B) TYPE:                amino acid
         (C) STRANDEDNESS:
         (D) TOPOLOGY:            linear (xi) SEQUENCE DESCRIPTION: SEQ ID NO: 255:

Asp Asp Phe Met Gly Gln Leu Leu Asn Gly Arg Val Leu Phe Pro Val
 1               5                  10                  15

Asn Leu Gln Leu Gly Ala
            20

(2) INFORMATION FOR SEQ ID NO:   256:

(i) SEQUENCE CHARACTERISTICS:
         (A) LENGTH:              17
         (B) TYPE:                amino acid
         (C) STRANDEDNESS:
         (D) TOPOLOGY:            linear (xi) SEQUENCE DESCRIPTION: SEQ ID NO: 256:

Ile Pro Arg Leu Gln Lys Ile Trp Lys Asn Tyr Leu Ser Met Asn Lys
 1               5                  10                  15

Tyr (2) INFORMATION FOR SEQ ID NO:   257:

(i) SEQUENCE CHARACTERISTICS:
         (A) LENGTH:              14
         (B) TYPE:                amino acid
         (C) STRANDEDNESS:
         (D) TOPOLOGY:            linear (xi) SEQUENCE DESCRIPTION: SEQ ID NO: 257:

Lys Arg Ser Phe Phe Ala Leu Arg Asp Gln Ile Pro Asp Leu
 1               5                  10

(2) INFORMATION FOR SEQ ID NO:   258:

(i) SEQUENCE CHARACTERISTICS:
         (A) LENGTH:              17
         (B) TYPE:                amino acid
         (C) STRANDEDNESS:
         (D) TOPOLOGY:            linear (xi) SEQUENCE DESCRIPTION: SEQ ID NO: 258:

Arg Gln Tyr Arg Leu Lys Lys Ile Ser Lys Glu Glu Lys Thr Pro Gly
 1               5                  10                  15

Cys (2) INFORMATION FOR SEQ ID NO:   259:

(i) SEQUENCE CHARACTERISTICS:
         (A) LENGTH:              13
```

```
             (B) TYPE:              amino acid
             (C) STRANDEDNESS:
             (D) TOPOLOGY:          linear (xi) SEQUENCE DESCRIPTION: SEQ ID NO: 259:

Ala Glu Val Tyr His Asp Val Ala Ala Ser Glu Phe Phe
 1               5                  10

(2) INFORMATION FOR SEQ ID NO:   260:

(i) SEQUENCE CHARACTERISTICS:
             (A) LENGTH:            19
             (B) TYPE:              amino acid
             (C) STRANDEDNESS:
             (D) TOPOLOGY:          linear (xi) SEQUENCE DESCRIPTION: SEQ ID NO: 260:

Asp Arg Pro Phe Leu Phe Val Val Arg His Asn Pro Thr Gly Thr Val
 1               5                  10                  15

Leu Phe Met (2) INFORMATION FOR SEQ ID NO:   261:

(i) SEQUENCE CHARACTERISTICS:
             (A) LENGTH:            16
             (B) TYPE:              amino acid
             (C) STRANDEDNESS:
             (D) TOPOLOGY:          linear (xi) SEQUENCE DESCRIPTION: SEQ ID NO: 261:

Met Pro His Phe Phe Arg Leu Phe Arg Ser Thr Val Lys Gln Val Asp
 1               5                  10                  15

(2) INFORMATION FOR SEQ ID NO:   262:

(i) SEQUENCE CHARACTERISTICS:
             (A) LENGTH:            20
             (B) TYPE:              amino acid
             (C) STRANDEDNESS:
             (D) TOPOLOGY:          linear (xi) SEQUENCE DESCRIPTION: SEQ ID NO: 262:

Lys Asn Ile Phe His Phe Lys Val Asn Gln Glu Gly Leu Lys Leu Ser
 1               5                  10                  15

Asn Asp Met Met
             20

(2) INFORMATION FOR SEQ ID NO:   263:

(i) SEQUENCE CHARACTERISTICS:
             (A) LENGTH:            16
             (B) TYPE:              amino acid
             (C) STRANDEDNESS:
             (D) TOPOLOGY:          linear (xi) SEQUENCE DESCRIPTION: SEQ ID NO: 263:

Lys Asn Ile Phe His Phe Lys Val Asn Gln Glu Gly Leu Lys Leu Ser
 1               5                  10                  15

(2) INFORMATION FOR SEQ ID NO:   264:

(i) SEQUENCE CHARACTERISTICS:
             (A) LENGTH:            20
             (B) TYPE:              amino acid
             (C) STRANDEDNESS:
             (D) TOPOLOGY:          linear
```

(xi) SEQUENCE DESCRIPTION: SEQ ID NO: 264:

Tyr Lys Gln Thr Val Ser Leu Asp Ile Gln Pro Tyr Ser Leu Val Thr
1               5                   10                  15

Thr Leu Asn Ser
            20

(2) INFORMATION FOR SEQ ID NO: 265:

(i) SEQUENCE CHARACTERISTICS:
        (A) LENGTH:             17
        (B) TYPE:               amino acid
        (C) STRANDEDNESS:
        (D) TOPOLOGY:           linear (xi) SEQUENCE DESCRIPTION: SEQ ID NO: 265:

Ser Thr Pro Glu Phe Thr Ile Leu Asn Thr Leu His Ile Pro Ser Phe
1               5                   10                  15

Thr (2) INFORMATION FOR SEQ ID NO: 266:

(i) SEQUENCE CHARACTERISTICS:
        (A) LENGTH:             18
        (B) TYPE:               amino acid
        (C) STRANDEDNESS:
        (D) TOPOLOGY:           linear (xi) SEQUENCE DESCRIPTION: SEQ ID NO: 266:

Thr Pro Glu Phe Thr Ile Leu Asn Thr Leu His Ile Pro Ser Phe Thr
1               5                   10                  15

Ile Asp (2) INFORMATION FOR SEQ ID NO: 267:

(i) SEQUENCE CHARACTERISTICS:
        (A) LENGTH:             16
        (B) TYPE:               amino acid
        (C) STRANDEDNESS:
        (D) TOPOLOGY:           linear (xi) SEQUENCE DESCRIPTION: SEQ ID NO: 267:

Thr Pro Glu Phe Thr Ile Leu Asn Thr Leu His Ile Pro Ser Phe Thr
1               5                   10                  15

(2) INFORMATION FOR SEQ ID NO: 268:

(i) SEQUENCE CHARACTERISTICS:
        (A) LENGTH:             16
        (B) TYPE:               amino acid
        (C) STRANDEDNESS:
        (D) TOPOLOGY:           linear (xi) SEQUENCE DESCRIPTION: SEQ ID NO: 268:

Ser Asn Thr Lys Tyr Phe His Lys Leu Asn Ile Pro Gln Leu Asp Phe
1               5                   10                  15

(2) INFORMATION FOR SEQ ID NO: 269:

(i) SEQUENCE CHARACTERISTICS:
        (A) LENGTH:             17
        (B) TYPE:               amino acid
        (C) STRANDEDNESS:
        (D) TOPOLOGY:           linear (xi) SEQUENCE DESCRIPTION: SEQ ID NO: 269:

Leu Pro Phe Phe Lys Phe Leu Pro Lys Tyr Phe Glu Lys Lys Arg Asn
 1               5                  10                  15
Thr (2) INFORMATION FOR SEQ ID NO: 270:

(i) SEQUENCE CHARACTERISTICS:
        (A) LENGTH:          15
        (B) TYPE:            amino acid
        (C) STRANDEDNESS:
        (D) TOPOLOGY:        linear (xi) SEQUENCE DESCRIPTION: SEQ ID NO: 270:

Leu Pro Phe Phe Lys Phe Leu Pro Lys Tyr Phe Glu Lys Lys Arg
 1               5                  10                  15

(2) INFORMATION FOR SEQ ID NO: 271:

(i) SEQUENCE CHARACTERISTICS:
        (A) LENGTH:          15
        (B) TYPE:            amino acid
        (C) STRANDEDNESS:
        (D) TOPOLOGY:        linear (xi) SEQUENCE DESCRIPTION: SEQ ID NO: 271:

Trp Asn Phe Tyr Tyr Ser Pro Gln Ser Ser Pro Asp Lys Lys Leu
 1               5                  10                  15

(2) INFORMATION FOR SEQ ID NO: 272:

(i) SEQUENCE CHARACTERISTICS:
        (A) LENGTH:          21
        (B) TYPE:            amino acid
        (C) STRANDEDNESS:
        (D) TOPOLOGY:        linear (xi) SEQUENCE DESCRIPTION: SEQ ID NO: 272:

Asp Val Ile Trp Glu Leu Leu Asn His Ala Gln Glu His Phe Gly Lys
 1               5                  10                  15
Asp Lys Ser Lys Glu
            20

(2) INFORMATION FOR SEQ ID NO: 273:

(i) SEQUENCE CHARACTERISTICS:
        (A) LENGTH:          16
        (B) TYPE:            amino acid
        (C) STRANDEDNESS:
        (D) TOPOLOGY:        linear (xi) SEQUENCE DESCRIPTION: SEQ ID NO: 273:

Asp Val Ile Trp Glu Leu Leu Ile Asn His Ala Gln Glu His Phe Gly
 1               5                  10                  15

(2) INFORMATION FOR SEQ ID NO: 274:

(i) SEQUENCE CHARACTERISTICS:
        (A) LENGTH:          23
        (B) TYPE:            amino acid
        (C) STRANDEDNESS:
        (D) TOPOLOGY:        linear (xi) SEQUENCE DESCRIPTION: SEQ ID NO: 274:

Met Pro Arg Ser Arg Ala Leu Ile Leu Gly Val Leu Ala Leu Thr Thr
 1               5                  10                  15
Met Leu Ser Leu Cys Gly Gly
            20